(12) United States Patent
Touaibia et al.

(10) Patent No.: US 11,760,715 B2
(45) Date of Patent: Sep. 19, 2023

(54) MODULATORS OF LIPOXYGENASE AND CYCLOOXYGENASE ENZYME ACTIVITY

(71) Applicant: Universite de Moncton, Moncton (CA)

(72) Inventors: Mohamed Touaibia, Dieppe (CA); Marc Edgar Surette, Moncton (CA)

(73) Assignee: Université de Moncton, Moncton (CA)

( * ) Notice: Subject to any disclaimer, the term of this patent is extended or adjusted under 35 U.S.C. 154(b) by 117 days.

(21) Appl. No.: 16/081,738

(22) PCT Filed: Mar. 3, 2017

(86) PCT No.: PCT/CA2017/050294
§ 371 (c)(1),
(2) Date: Aug. 31, 2018

(87) PCT Pub. No.: WO2017/147718
PCT Pub. Date: Sep. 8, 2017

(65) Prior Publication Data
US 2019/0119194 A1      Apr. 25, 2019

Related U.S. Application Data

(60) Provisional application No. 62/303,120, filed on Mar. 3, 2016.

(51) Int. Cl.
| C07C 69/732 | (2006.01) |
| C07C 69/736 | (2006.01) |
| C07C 69/65 | (2006.01) |
| C07C 69/94 | (2006.01) |
| C07D 319/18 | (2006.01) |
| C07C 235/34 | (2006.01) |
| C07C 69/618 | (2006.01) |
| C07C 69/734 | (2006.01) |

(52) U.S. Cl.
CPC .......... *C07C 69/732* (2013.01); *C07C 69/618* (2013.01); *C07C 69/65* (2013.01); *C07C 69/734* (2013.01); *C07C 69/736* (2013.01); *C07C 69/94* (2013.01); *C07C 235/34* (2013.01); *C07D 319/18* (2013.01)

(58) Field of Classification Search
None
See application file for complete search history.

(56) References Cited

U.S. PATENT DOCUMENTS

| 4,733,002 A * | 3/1988 | Yokoyama | C07C 69/732 |
| | | | 568/325 |
| 4,810,716 A * | 3/1989 | Connor | C07C 45/72 |
| | | | 514/365 |
| 4,959,503 A | 9/1990 | Connor et al. | |
| 5,191,108 A * | 3/1993 | Carson | C07C 229/64 |
| | | | 562/463 |
| 5,763,673 A * | 6/1998 | Yamazaki | A61P 29/00 |
| | | | 568/325 |
| 8,106,233 B2 | 1/2012 | Rudolph et al. | |
| 8,268,293 B2 | 9/2012 | Rudolph et al. | |
| 2003/0162789 A1 | 8/2003 | Park et al. | |

FOREIGN PATENT DOCUMENTS

| CA | 1328279 | 4/1994 |
| EP | 0 717 027 A1 | 6/1996 |
| JP | 2006273839 A | 10/2006 |
| WO | 2006111233 A1 | 10/2006 |
| WO | 2006111234 A1 | 10/2006 |
| WO | 2015/151005 A2 | 10/2015 |
| WO | 2015151005 A2 | 10/2015 |

OTHER PUBLICATIONS

Choi et al., Anti-INflammatory and Antinociceptive Effects of Sinapyl Alcohol and its Glucoside Syringin. Planta Medica, 2004, 70, 1027-1032.*
Sud'ina et al., Caffeic acid phenethyl ester as a lipoxygenase inhibitor with antioxidant properties. FEBS Letters, 1993, 329, 21-24.*
CAPLUS printout of "Qian et al., Structure-activity relationship for anti-haemolysis and cytotoxicity against HL-60 cells of caffeic acid phenethyl ester derivatives. Shengwu Wuli Xuebao, 2010, 26, 294-300".*
Ning et al., Synthesis and neuroprotective effect of E-3,4-dihydroxy styryl aralkyl ketones derivatives against oxidative stress and inflammation. Bioorgnaic & Medicinal CHemistry Letters, 2013, 23, 3700-3703.*
Iyer et al., Treating Chemical Diversity in QSAR Analysis: Modeling Diverse HIV-1 Integrase Inhibitors Using 4D Fingerprints. Journal of Chemical Information and Modeling, 2007, 47, 1945-1960.*
Wang et al., Synthesis of Caffeic Acid Phenethyl Ester Analogues and Their Cytotoxicities Against Human Cancer Cells. Asian Journal of Chemistry, 2014, 26, 2686-2690.*
Chemical Abstract Registry No. 19312-19-7, indexed in the Registry File on STN CAS Online Nov. 16, 1984.*
Zhu et al., Fungitoxic and Phytotoxic Activities of Cinnamic Acid Esters and Amides. Journal of Pesticide Science, 2000, 25, 263-266.*
Natarajan et al., "Caffeic acid phenethyl ester is a potent and specific inhibitor of activation of nuclear transcription factor NF-?B," Proc. Natl. Acad. Sci. USA, Immunology, vol. 93, pp. 9090-9095, 1996.
Extended European Search Report, EP 17759057.7, dated Aug. 1, 2019 (8 pages).
Appendino et al., "Chemoselective Esterification of Phenolic Acids and Alcohols", Organic Letters, 4(22):3839-3841, 2002.
Yamazaki et al., "Anti-inflammatory effect of YPE-01, a novel diarylheptanoid derivative, on dermal inflammation in mice", Inflammation Research, 47:182-186, 1998.
Zanarotti, "Synthesis and Reactivity of Vinyl Quinone Methides", J. Org. Chem., 50(7):941-945, 1985.

(Continued)

*Primary Examiner* — Po-Chih Chen
(74) *Attorney, Agent, or Firm* — Honigman LLP; Fernando Alberdi; Jonathan P. O'Brien

(57) ABSTRACT

The present invention relates to modulators of lipoxygenase and/or cyclooxygenase enzyme. The present invention also provides compositions comprising such modulators, and methods therewith for treating lipoxygenase receptor mediated diseases.

9 Claims, No Drawings

(56) References Cited

OTHER PUBLICATIONS

PCT International Search Report, PCT/CA2017/050294, dated Jun. 1, 2017 (9 pages).
Beauregard et al., "CAPE Analogs Induce Growth Arrest and Apoptosis in Breast Cancer Cells", Molecules, 20:12576-12589, 2015.
Boudreau et al., "Caffeic Acid Phenethyl Ester and Its Amide Analogues Are Potent inhibitors of Leukotriene Biosynthesis in Human Polymorphonuclear Leukocytes", PLOS ONE, 7(2):e31833, 2012.
Chiang et al., "Caffeic Acid Derivatives Inhibit the Growth of Colon Cancer: involvement of the PI3-K/Akt and AMPK Signaling Pathways", PLOS ONE, 9(6):e99631, 2014.
Compound with the following CAS No. 142-018-03-9, Entered STN on Jane 24, 1992.
Doiron et al., "Clicked Cinnamic/Caffeic Esters and Amides as Radical Scavengers and 5-Lipoxygenase Inhibitors", International Journal of Medicinal Chemistry, vol. 2014, Article ID 931756, 12 pages.
Doiron et al., "Structure-activity relationship of caffeic acid phenethyl ester analogs as new 5-lipoxygenase inhibitors", Chem. Biol. Drug Des., 89:514-528, 2017.
Hu et al., "Structure-activity Relationship of Sintenin and its Analogues on Six Human Tumor Cell Lines", Chinese Chemical Letters, 16(8):997-1000, 2005.
Jayaprakasam et al., "Impact of Alkyl Esters of Caffeic and Ferulic Acids on Tumor Cell Proliferation, Cyclooxygenase Enzyme, and Lipid Peroxidation", J. Agric. Food Chem., 54:5375-5381, 2006.
Morin et al., "NMR Metabolomics Analysis of the Effects of 5-Lipoxygenase Inhibitors on Metabolism in Glioblastomas", J. Proteome Res., 12:2165-2176, 2013.
Reynolds et al., "Conversion of α-Haloaldehydes into Acylating Agents by an Internal Redox Reaction Catalyzed by Nucleophilic Carbenes", J. Am. Chem. Soc. (JACS), 126:9518-9519, 2004.
Sanderson et al., "Antiproliferative, antiandrogenic and cytotoxic effects of navel caffeic acid derivatives in LNCaP human anddrogen-dependent prostate cancer cells", Bioorganic & Medicinal Chemistry, 21:7182-7193, 2013.
Zhou et al., "A CAPE analogue as novel antiplatelet agent efficiently inhibits collagen-induced platelet aggregation", Pharmazie, 69:615-620, 2014.
Compound with the following CAS Registry No. 746642-33-1, Entered STN: Sep. 17, 2004, 1 page.
Compound with the following CAS Registry No. 746642-29-5, Entered STN: Sep. 17, 2004, 1 page.
Compound with the following CAS Registry No. 502515-57-3, Entered STN: Apr. 9, 2003, 1 page.
Compound with the following CAS Registry No. 298211-94-6, Entered STN: Oct. 23, 2000, 1 page.
Compound with the following CAS Registry No. 290311-72-7, Entered STN: Sep. 22, 2000, 1 page.
Compound with the following CAS Registry No. 260437-91-0, Entered STN: Mar. 31, 2000, 1 page.
Compound with the following CAS Registry No. 260437-89-6, Entered STN: Mar. 31, 2000, 1 page.
Compound with the following CAS Registry No. 179692-04-7, Entered STN: Aug. 16, 1996, 1 page.
Compound with the following CAS Registry No. 179692-03-6, Entered STN: Aug. 16, 1996, 1 page.
Compound with the following CAS Registry No. 179692-02-5, Entered STN: Aug. 16, 1996, 1 page.
Compound with the following CAS Registry No. 179692-01-4, Entered STN: Aug. 16, 1996, 1 page.
Compound with the following CAS Registry No. 179691-99-7, Entered STN: Aug. 16, 1996, 1 page.
Compound with the following CAS Registry No. 179691-97-5, Entered STN: Aug. 16, 1996, 1 page.
Compound with the following CAS Registry No. 169232-14-8, Entered STN: Oct. 24, 1995, 1 page.
Compound with the following CAS Registry No. 169232-13-7, Entered STN: Oct. 24, 1995, 1 page.
Compound with the following CAS Registry No. 169232-12-6, Entered STN: Oct. 24, 1995, 1 page.
Compound with the following CAS Registry No. 134841-09-1, Entered STN: Jul. 12, 1991, 1 page.
Compound with the following CAS Registry No. 134841-08-0, Entered STN: Jul. 12, 1991, 1 page.
Compound with the following CAS Registry No. 118971-54-3, Entered STN: Feb. 10, 2009, 1 page.
Compound with the following CAS Registry No. 68799-44-0, Entered STN: Nov. 16, 1984, 1 page.
Compound with the following CAS Registry No. 56759-10-5, Entered STN: Nov. 16, 1984, 1 page.
Compound with the following CAS Registry No. 618455-44-0, Entered STN: Nov. 20, 2003, 1 page.
Compound with the following CAS Registry No. 618455-48-4, Entered STN: Nov. 20, 2003, 1 page.
Compound with the following CAS Registry No. 618455-52-0, Entered STN: Nov. 20, 2003, 1 page.
Compound with the following CAS Registry No. 1012309-95-3, Entered STN: Apr. 6, 2008, 1 page.
Compound with the following CAS Registry No. 193219-32-8, Entered STN: Apr. 6, 2008, 1 page.
Compound with the following CAS Registry No. 142018-03-9, Entered STN: Jun. 24, 1992, 1 page.
Berthelot et al: "vir-Gene-inducing activities of hydroxycinnamic acid amides in Agrobacterium tumefaciens", PHYTOCHEMISTRY, vol. 49, No. 6, Nov. 20, 1998 (Nov. 20, 1998), pp. 1537-1548.
Chave et al: "Amides and lignanamides from Porcelia Macrocarpa", Phytochemistry, vol. 46, No. 5, Nov. 1, 1997 (Nov. 1, 1997), pp. 879-881.
Ley, "Phenolic Acid Amides of Phenolic Benzylamines Against UVA-Induced Oxidative Stress in Skin", International Journal of Cosmetic Science, Kluwer Academic Publishers, Dordrecht, NL, vol. 23, No. 1, Jan. 1, 2001 (Jan. 1, 2001), pp. 35-48.
Teitel, "An Improved Synthesis of Various Racemic Polyphenolic Tetrahydroisoquinoline Alkaloids", Journal of Heterocyclic Chemistry, vol. 5, No. 6, Dec. 1, 1968 (Dec. 1, 1968), pp. 825-829.
Buolamwini et al., ""CoMFA and CoMSIA 3D QSAR and Docking Studies on Conformationally-Restrained Cinnamoyl HIV-1 Integrase Inhibitors: Exploration of a Binding Mode at the Active Site,"" J. Med. Chem. 2002, 45, 841-852.
Compound with the following CAS Registry Nos. 1637779-86-2, Entered STN: Dec. 4, 2014, 1 page.
Compound with the following CAS Registry Nos. 1637779-85-1, Entered STN: Dec. 4, 2014, 1 page.
Compound with the following CAS Registry Nos. 1637779-84-0, Entered STN: Dec. 4, 2014, 1 page.
Compound with the following CAS Registry Nos. 1637779-83-9, Entered STN: Dec. 4, 2014, 1 page.
Compound with the following CAS Registry No. 1627446-54-1, Entered STN: Sep. 29, 2014, 1 page.
Compound with the following CAS Registry No. 1623423-73-3, Entered STN: Sep. 18, 2014, 1 page.
Compound with the following CAS Registry No. 1623423-72-2, Entered STN: Sep. 18, 2014, 1 page.
Compound with the following CAS Registry No. 1622427-40-0, Entered STN: Sep. 11, 2014, 1 page.
Compound with the following CAS Registry No. 1620329-35-2, Entered STN: Aug. 11, 2014, 1 page.
Compound with the following CAS Registry No. 1618649-48-1, Entered STN: Jul. 31, 2014, 1 page.
Compound with the following CAS Registry No. 1473395-96-8, Entered STN: Nov. 14, 2013, 1 page.
Compound with the following CAS Registry No. 1357899-27-4, Entered STN: Feb. 28, 2012, 1 page.
Compound with the following CAS Registry No. 1357899-19-4, Entered STN: Feb. 28, 2012, 1 page.
Compound with the following CAS Registry No. 1357899-05-8, Entered STN: Feb. 28, 2012, 1 page.
Compound with the following CAS Registry No. 1357898-97-5, Entered STN: Feb. 28, 2012, 1 page.

(56) References Cited

OTHER PUBLICATIONS

Compound with the following CAS Registry No. 1357898-94-2, Entered STN: Feb. 28, 2012, 1 page.
Compound with the following CAS Registry No. 1338341-03-9, Entered STN: Oct. 25, 2011, 1 page.
Compound with the following CAS Registry No. 1303035-83-7, Entered STN: May 30, 2011, 1 page.
Compound with the following CAS Registry No. 1287382-95-9, Entered STN: Apr. 29, 2011, 1 page.
Compound with the following CAS Registry No. 1287288-47-4, Entered STN: Apr. 28, 2011, 1 page.
Compound with the following CAS Registry No. 1287244-96-5, Entered STN: Apr. 28, 2011, 1 page.
Compound with the following CAS Registry No. 1287196-60-4, Entered STN: Apr. 28, 2011, 1 page.
Compound with the following CAS Registry No. 1103519-66-9, Entered STN: Feb. 10, 2009, 1 page.
Compound with the following CAS Registry No. 1103519-64-7, Entered STN: Feb. 10, 2009, 1 page.
Compound with the following CAS Registry No. 1103519-62-5, Entered STN: Feb. 10, 2009, 1 page.
Compound with the following CAS Registry No. 1103519-59-0, Entered STN: Feb. 10, 2009, 1 page.
Compound with the following CAS Registry No. 1103519-47-6, Entered STN: Feb. 10, 2009, 1 page.
Compound with the following CAS Registry No. 1081273-75-7, Entered STN: Dec. 7, 2008, 1 page.
Compound with the following CAS Registry No. 959221-46-6, Entered STN: Dec. 21, 2007, 1 page.
Compound with the following CAS Registry No. 959059-54-2, Entered STN: Dec. 20, 2007, 1 page.
Compound with the following CAS Registry No. 950665-13-1, Entered STN: Oct. 15, 2007, 1 page.
Compound with the following CAS Registry No. 935777-52-9, Entered STN: May 24, 2007, 1 page.
Compound with the following CAS Registry No. 931620-15-4, Entered STN: Apr. 22, 2007, 1 page.
Compound with the following CAS Registry No. 905502-61-6, Entered STN: Aug. 31, 2006, 1 page.
Compound with the following CAS Registry No. 901777-04-6, Entered STN: Aug. 16, 2006, 1 page.
Compound with the following CAS Registry No. 901777-03-5, Entered STN: Aug. 16, 2006, 1 page.
Compound with the following CAS Registry No. 901777-02-4, Entered STN: Aug. 16, 2006, 1 page.
Compound with the following CAS Registry No. 901777-01-3, Entered STN: Aug. 16, 2006, 1 page.
Compound with the following CAS Registry No. 901777-00-2, Entered STN: Aug. 16, 2006, 1 page.
Compound with the following CAS Registry No. 901776-99-6, Entered STN: Aug. 16, 2006, 1 page.
Compound with the following CAS Registry No. 885058-26-4, Entered STN: May 21, 2006, 1 page.
Compound with the following CAS Registry No. 885058-25-3, Entered STN: May 21, 2006, 1 page.
Compound with the following CAS Registry No. 885058-24-2, Entered STN: May 21, 2006, 1 page.
Compound with the following CAS Registry No. 875019-21-9, Entered STN: Feb. 23, 2006, 1 page.
Compound with the following CAS Registry No. 875019-19-5, Entered STN: Feb. 23, 2006, 1 page.
Compound with the following CAS Registry No. 857397-81-0, Entered STN: Jul. 28, 2005, 1 page.
Compound with the following CAS Registry No. 746642-37-5, Entered STN: Sep. 17, 2004, 1 page.
Compound with the following CAS Registry No. 746642-36-4, Entered STN: Sep. 17, 2004, 1 page.
Compound with the following CAS Registry No. 746642-35-3, Entered STN: Sep. 17, 2004, 1 page.
Hu, L. et al., "Synthesis and Biological Evaluation of a Natural Ester Sintenin and its Synthetic Analogues," Journal of Natural Products, 2005, pp. 342-348, vol. 68, No. 3, American Chemical Society and American Society of Pharmacognosy.

* cited by examiner

MODULATORS OF LIPOXYGENASE AND CYCLOOXYGENASE ENZYME ACTIVITY

CROSS-REFERENCE TO RELATED APPLICATIONS

This application claims the benefit of and priority under 35 U.S.C. § 371 to Patent Cooperation Treaty Application PCT/CA2017/050294, filed Mar. 3, 2017, which claims the benefit of U.S. Provisional Application Ser. No. 62/303,120, filed Mar. 3, 2016. The PCT Application No. PCT/CA2017/050294 is incorporated herein by reference in its entirety.

TECHNICAL FIELD OF THE INVENTION

The present invention relates to modulators of lipoxygenase (LO) and cyclooxygenase (COX-1 & COX-2) enzyme activity. The present invention also provides compositions comprising such modulators, and methods for treating lipoxygenase and cyclooxygenase mediated diseases.

BACKGROUND OF THE INVENTION

Prostaglandins (PG) and leukotrienes (LT) play a critical role in the inflammation process. The inhibition of prostaglandin production, especially production of $PGG_2$, $PGH_2$ and $PGE_2$, has been a common target of anti-inflammatory drug discovery. However, common non-steroidal anti-inflammatory drugs (NSAIDs) that are active in reducing the prostaglandin-induced pain and swelling associated with the inflammation process are also active in affecting other prostaglandin-regulated processes not associated with the inflammation process. Thus, use of high doses of most common NSAIDs can produce severe side effects, including life threatening ulcers, and liver damage that limit their therapeutic potential. An alternative to NSAIDs is the use of corticosteroids, which have even more drastic side effects, especially when long term therapy is involved.

Previous NSAIDs have been found to prevent the production of prostaglandins by inhibiting enzymes in the human arachidonic acid/prostaglandin pathway including the enzyme cyclooxygenase (COX). The discovery of an inducible enzyme associated with inflammation (named "cyclooxygenase-2 (COX-2)" or "prostaglandin G/H synthase II") provides a viable target of inhibition which more effectively reduces inflammation and produces fewer and less drastic side effects.

In another portion of the arachidonic acid pathway, physiologically active leukotrienes, such as leukotriene $B_4$ ($LTB_4$), leukotriene $C_4$ ($LTC_4$) and leukotriene $D_4$ ($LTD_4$) and other metabolites, are produced by the 5-lipoxygenase-mediated (5-LO) oxidation of arachidonic acid. These leukotrienes have been implicated in various inflammation-related disorders and allergic diseases, and thus compounds which inhibit 5-lipoxygenase are useful in the treatment of disease states in which leukotrienes play an important role.

Cyclooxygenase-2 (COX-2) is usually undetectable in most tissues; however, its expression is increased during states of inflammation or, experimentally, in response to mitogenic stimuli. COX-2 is accordingly referred to as "inducible." It is this inducible COX-2 form that is responsible for prostaglandin overproduction through the COX pathway in response to tissue injury, and stimulation by growth factors and proinflammatory cytokines.

As the COX pathway is the rate-limiting step for prostaglandin synthesis, the COX reaction is the principal target for anti-inflammatory drug action. And it is inhibition of COX activity that accounts for the activity of the non-steroidal anti-inflammatory drugs (NSAIDs), such as aspirin, acetaminophen, ibuprofen, naproxen, indomethacin.

Selective dual inhibitors of both cyclooxygenase-2 and 5-lipoxygenase, which affect the two enzymes at low concentrations, will more completely and permanently affect the damage caused by the various diseases and disorders mediated by cyclooxygenase-2 and 5-lipoxygenase but without the gastrointestinal side effects associated with traditional NSAIDs.

Compounds which inhibit 5-lipoxygenase have been described in U.S. Pat. Nos. 5,364,877, 5,302,603, 5,234,950, 5,098,932 and 5,354,865, among others.

Compounds which inhibit both cyclooxygenase and 5-lipoxygenase have been described in U.S. Pat. Nos. 5,051,518, 5,155,110, 5,298,521, 5,242,940, 5,234,939, and 5,356,898, 6,432,999, 6,512,121, 6,515,014, 6,677,364, 6,696,477, 6,753,344, 6,875,785 and 6,998,415 among others.

The invention's compounds are found to show usefulness as dual inhibitors of cyclooxygenase and 5-lipoxygenase.

SUMMARY OF THE INVENTION

The invention includes compounds useful as modulators of lipoxygenase and/or cyclooxygenase (COX) enzyme activity, and pharmaceutical compositions comprising the compounds. The invention further includes methods of modulating lipoxygenase and/or cyclooxygenase enzyme using a compound or pharmaceutical compositions described herein. The invention also includes methods of treating diseases or conditions associated with, or mediated by in vivo lipoxygenase and/or cyclooxygenase enzyme activity.

In a first aspect, the present invention provides a compound of Formula Ia:

Formula Ia

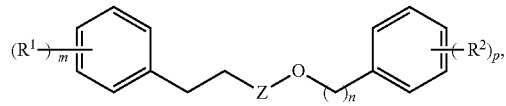

or a pharmaceutically acceptable salt thereof, wherein

Z is $CH_2$ or $C=O$;

$R^1$ and $R^2$ are each independently —OH, halo, —CN, —$NO_2$, —$CF_3$, —C(O)H, —C(O)$R^{1a}$, —C(O)OH, —C(O)O$R^{1a}$, —O$R^{1a}$, —NH$R^{1a}$, —N($R^{1a}$)$_2$, —$SO_2R^{1a}$, —$SO_2$NH$R^{1a}$, —$SO_2$N($R^{1a}$)$_2$, —NH$SO_2R^{1a}$, —NH$SO_2$NH$R^{1a}$, or —NH$SO_2$N($R^{1a}$)$_2$; or two $R^1$ substituents or two $R^2$ substituents, together with the atoms to which they are attached, form a 4-10 membered aryl, heteroaryl, cycloalkyl, or heterocycloalkyl, optionally substituted with one or more $R^{1a}$;

each $R^{1a}$ is independently —$C_{1-6}$ alkyl, cycloalkyl, heterocycloalkyl, aryl, or heteroaryl, wherein each $R^{1a}$ is optionally and independently substituted with —OH, halo, —CN, —$NO_2$, —$CF_3$, —C(O)H, —C(O)(—$C_{1-6}$ alkyl), —C(O)OH, —C(O)O(—$C_{1-6}$ alkyl), —O(—$C_{1-6}$ alkyl), —NH(—$C_{1-6}$ alkyl), —N(—$C_{1-6}$ alkyl)$_2$, —$SO_2$(—$C_{1-6}$ alkyl), —$SO_2$NH(—$C_{1-6}$ alkyl), —$SO_2$N(—$C_{1-6}$ alkyl)$_2$, —NH$SO_2$(—$C_{1-6}$ alkyl), —NH$SO_2$NH(—$C_{1-6}$ alkyl), or —NH$SO_2$N(—$C_{1-6}$ alkyl)$_2$;

m and p are each independently an integer from 0-5; and n is an integer from 4-10.

In related aspects, the present invention provides a compound of Formula Ib:

Formula Ib

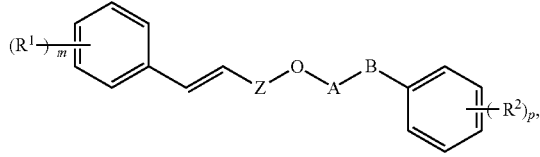

or a pharmaceutically acceptable salt thereof, wherein

Z is $CH_2$ or C=O;

$R^1$ and $R^2$ are each independently —OH, halo, —CN, —$NO_2$, —$CF_3$, —C(O)H, —C(O)$R^{1a}$, —C(O)OH, —C(O)O$R^{1a}$, —O$R^{1a}$, —NH$R^{1a}$, —N($R^{1a}$)$_2$, —$SO_2R^{1a}$, —$SO_2$NH$R^{1a}$, —$SO_2$N($R^{1a}$)$_2$, —NHSO$_2R^{1a}$, —NHSO$_2$NH$R^{1a}$, or —NHSO$_2$N($R^{1a}$)$_2$; or two $R^1$ substituents or two $R^2$ substituents, together with the atoms to which they are attached, form a 4-10 membered aryl, heteroaryl, cycloalkyl, or heterocycloalkyl, optionally substituted with one or more $R^{1a}$;

each $R^{1a}$ is independently —$C_{1-6}$ alkyl, cycloalkyl, heterocycloalkyl, aryl, or heteroaryl, wherein each $R^{1a}$ is optionally and independently substituted with —OH, halo, —CN, —$NO_2$, —$CF_3$, —$C_{1-6}$ alkyl, —C(O)H, —C(O)(—$C_{1-6}$ alkyl), —C(O)OH, —C(O)O(—$C_{1-6}$ alkyl), —O(—$C_{1-6}$ alkyl), —NH(—$C_{1-6}$ alkyl), —N(—$C_{1-6}$ alkyl)$_2$, —$SO_2$(—$C_{1-6}$ alkyl), —$SO_2$NH(—$C_{1-6}$ alkyl), —$SO_2$N(—$C_{1-6}$ alkyl)$_2$, —NHSO$_2$(—$C_{1-6}$ alkyl), —NHSO$_2$NH(—$C_{1-6}$ alkyl), or —NHSO$_2$N(—$C_{1-6}$ alkyl)$_2$;

A is a $C_{1-6}$ alkylene, optionally substituted with one to three of —OH, halo, —CN, —$NO_2$, —$CF_3$, —$C_{1-6}$ alkyl, —C(O)H, —C(O)(—$C_{1-6}$ alkyl), —C(O)OH, —C(O)O(—$C_{1-6}$ alkyl), —O(—$C_{1-6}$ alkyl), —NH(—$C_{1-6}$ alkyl), —N(—$C_{1-6}$ alkyl)$_2$, —$SO_2$(—$C_{1-6}$ alkyl), —$SO_2$NH(—$C_{1-6}$ alkyl), —$SO_2$N(—$C_{1-6}$ alkyl)$_2$, —NHSO$_2$(—$C_{1-6}$ alkyl), —NHSO$_2$NH$R^{1a}$, or —NHSO$_2$N($R^{1a}$)$_2$;

B is

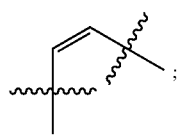 [SMILES: */C=C\*]

and m and p are each independently an integer from 0-5.

In a related aspect, the present invention provides a compound of Formula Ic:

Formula Ic

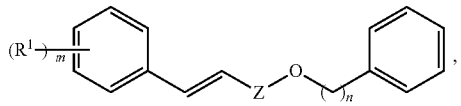

or a pharmaceutically acceptable salt thereof, wherein

Z is $CH_2$ or C=O;

each $R^1$ is independently —OH, halo, —CN, —$NO_2$, —$CF_3$, —C(O)H, —C(O)$R^{1a}$, —C(O)OH, —C(O)O$R^{1a}$, —O$R^{1a}$, —NH$R^{1a}$, —N($R^{1a}$)$_2$, —$SO_2R^{1a}$, —$SO_2$NH$R^{1a}$, —$SO_2$N($R^{1a}$)$_2$, —NHSO$_2R^{1a}$, —NHSO$_2$NH$R^{1a}$, or —NHSO$_2$N($R^{1a}$)$_2$; or two $R^1$ substituents, together with the atoms to which they are attached, form a 4-10 membered aryl, heteroaryl, or cycloalkyl, optionally substituted with one or more $R^{1a}$;

each $R^{1a}$ is independently —$C_{1-6}$ alkyl, cycloalkyl, heterocycloalkyl, aryl, or heteroaryl, wherein each $R^{1a}$ is optionally and independently substituted with —OH, halo, —CN, —$NO_2$, —$CF_3$, —$C_{1-6}$ alkyl, —C(O)H, —C(O)(—$C_{1-6}$ alkyl), —C(O)OH, —C(O)O(—$C_{1-6}$ alkyl), —O(—$C_{1-6}$ alkyl), —NH(—$C_{1-6}$ alkyl), —N(—$C_{1-6}$ alkyl)$_2$, —$SO_2$(—$C_{1-6}$ alkyl), —$SO_2$NH(—$C_{1-6}$ alkyl), —$SO_2$N(—$C_{1-6}$ alkyl)$_2$, —NHSO$_2$(—$C_{1-6}$ alkyl), —NHSO$_2$NH(—$C_{1-6}$ alkyl), —NHSO$_2$N(—$C_{1-6}$ alkyl)$_2$;

each m is independently an integer from 0-5; and n is 2 or 3, provided that when n is 2,

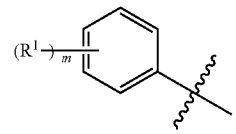

of Formula Ic is not phenyl,

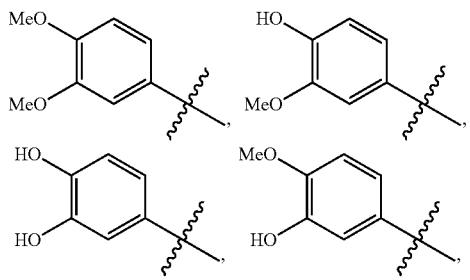

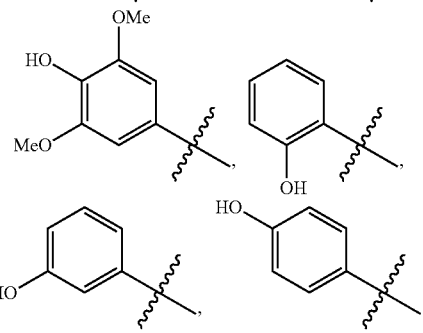

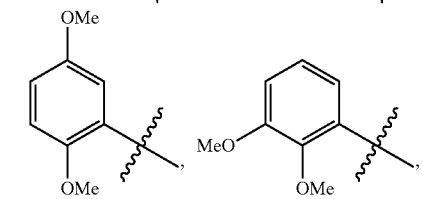

-continued

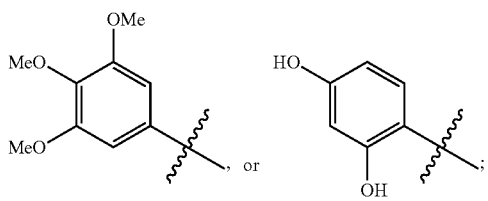, or and
when n is 3,

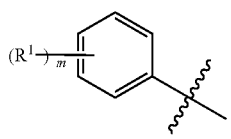

of Formula Ic is not

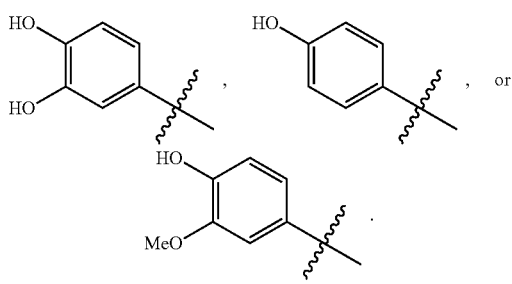.

In a related aspect, the present invention provides a compound of Formula Id,

Formula Id

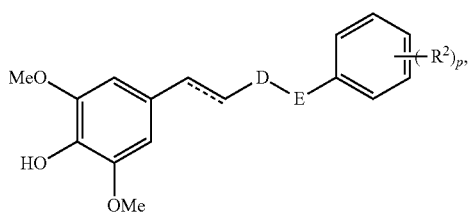

or a pharmaceutically acceptable salt thereof, each $R^2$ is each independently —OH, halo, —CN, —NO$_2$, —CF$_3$, —C(O)H, —C(O)R$^{1a}$, —C(O)OH, —C(O)OR$^{1a}$, —OR$^{1a}$, —NHR$^{1a}$, —N(R$^{1a}$)$_2$, —SO$_2$R$^{1a}$, —SO$_2$NHR$^{1a}$, —SO$_2$N(R$^{1a}$)$_2$, —NHSO$_2$R$^{1a}$, —NHSO$_2$NHR$^{1a}$, or —NHSO$_2$N(R$^{1a}$)$_2$;

each $R^{1a}$ is independently —C$_{1-6}$ alkyl, cycloalkyl, heterocycloalkyl, aryl, or heteroaryl, wherein each R$^{1a}$ is optionally and independently substituted with —OH, halo, —CN, —NO$_2$, —CF$_3$, —C(O)H, —C(O)(—C$_{1-6}$ alkyl), —C(O)OH, —C(O)O(—C$_{1-6}$ alkyl), —O(—C$_{1-6}$ alkyl), —NH(—C$_{1-6}$ alkyl), —N(—C$_{1-6}$ alkyl)$_2$, —SO$_2$(—C$_{1-6}$ alkyl), —SO$_2$NH(—C$_{1-6}$ alkyl), —SO$_2$N(—C$_{1-6}$ alkyl)$_2$, —NHSO$_2$(—C$_{1-6}$ alkyl), —NHSO$_2$NH(—C$_{1-6}$ alkyl), or —NHSO$_2$N(—C$_{1-6}$ alkyl)$_2$;

the dotted line,

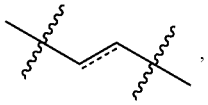, denotes a double bond or single bond;
D is a —C(R$^{1b}$)$_2$—, —C(R$^{1b}$)$_2$O—, —C(R$^{1b}$)$_2$N(R$^{1b}$)—, —C(O)—, —C(O)O—, —C(O)N(R$^{1b}$)—, —O—, or —N(R$^{1b}$)—;
E is a C$_{1-10}$ alkylene chain that is optionally substituted with one or more R$^{1b}$ substituents;
each R$^{1b}$ is independently hydrogen, halo, or R$^{1a}$; and
p is an integer from 0-5;
provided that the compound is not

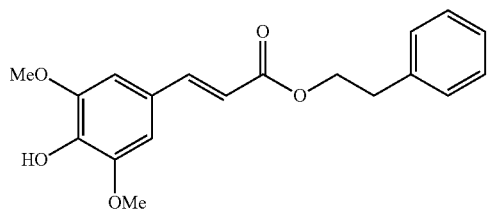 [SMILES: COc1cc(/C=C/C(=O)OCCc2ccccc2)cc(OC)c1O]

In a second aspect, the present invention provides a method of modulating lipoxygenase and/or cyclooxygenase activity, comprising contacting said lipoxygenase and/or cyclooxygenase with a compound of Formula IIa, Formula IIb, or Formula IIc Formula IIa Formula IIb Formula IIc or a pharmaceutically acceptable salt thereof, wherein
each Z is independently CH$_2$ or C=O;
each W is independently hydrogen, a C$_{1-6}$ alkyl, cycloalkyl, heterocycloalkyl, aralkyl, aryl, heteroaralkyl, or heteroaryl, wherein W is optionally and independently substituted with up to three R$^1$ substituents;
each R$^1$ is independently —OH, halo, —CN, —NO$_2$, —CF$_3$, —C(O)H, —C(O)R$^{1a}$, —C(O)OH, —C(O)OR$^{1a}$, —OR$^{1a}$, —NHR$^{1a}$, —N(R$^{1a}$)$_2$, —SO$_2$R$^{1a}$, —SO$_2$NHR$^{1a}$, —SO$_2$N(R$^{1a}$)$_2$, —NHSO$_2$R$^{1a}$, —NHSO$_2$NHR$^{1a}$, or —NHSO$_2$N(R$^{1a}$)$_2$; or
two R$^1$ substituents, together with the atoms to which they are attached, form a 4-10 membered aryl, heteroaryl, cycloalkyl, or heterocycloalkyl, optionally substituted with one or more R$^{1a}$;

each $R^{1a}$ is independently —$C_{1-6}$ alkyl, cycloalkyl, heterocycloalkyl, aryl, or heteroaryl, wherein each $R^{1a}$ is optionally and independently substituted with —OH, halo, —CN, —$NO_2$, —$CF_3$, —$C_{1-6}$ alkyl, —C(O)H, —C(O)(—$C_{1-6}$ alkyl), —C(O)OH, —C(O)O(—$C_{1-6}$ alkyl), —O(—$C_{1-6}$ alkyl), —NH(—$C_{1-6}$ alkyl), —N(—$C_{1-6}$ alkyl)$_2$, —$SO_2$(—$C_{1-6}$ alkyl), —$SO_2$NH(—$C_{1-6}$ alkyl), —$SO_2$N(—$C_{1-6}$ alkyl)$_2$, —$NHSO_2$(—$C_{1-6}$ alkyl), —$NHSO_2$NH(—$C_{1-6}$ alkyl), or —$NHSO_2$N(—$C_{1-6}$ alkyl)$_2$;

the dotted line,

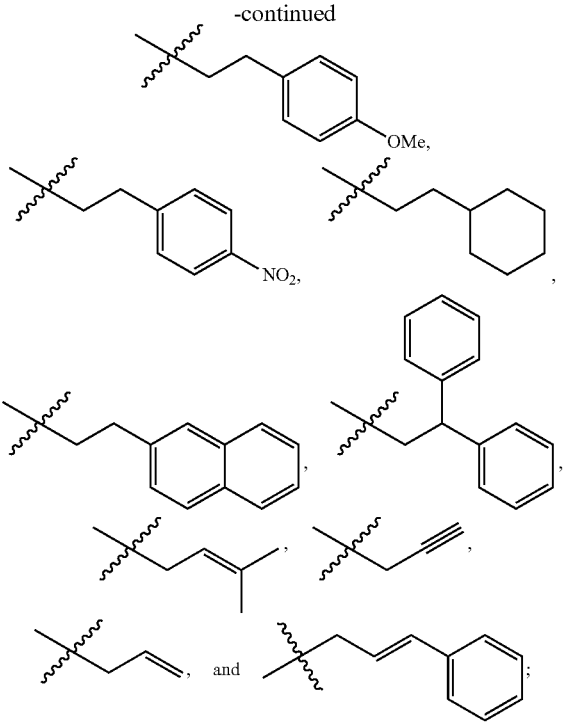

in Formula IIa denotes a double bond or single bond;
X is a bond, —O—, or —NH—;
Y is a moiety selected from the group consisting of:

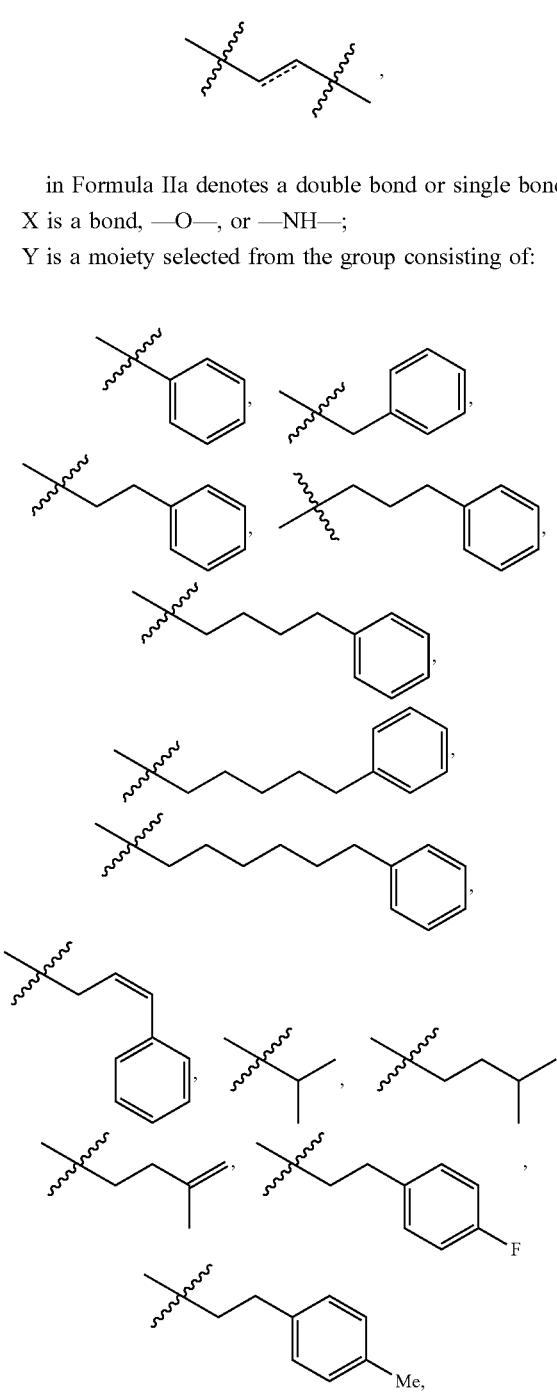

and
each m is independently an integer from 0-5;
provided that:
when X—Y is

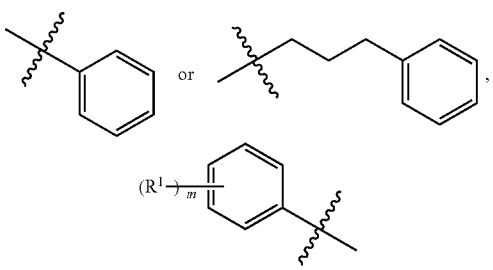

of Formula IIa is not

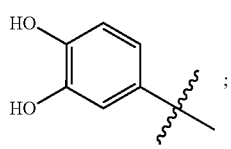 [SMILES: *c1ccc(O)c(O)c1]

when X—Y is

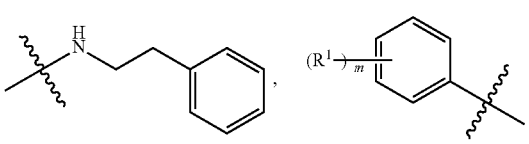

of Formula IIa is not phenyl or

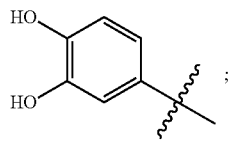

when X—Y is

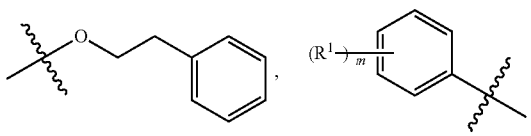

of Formula IIa is not phenyl,

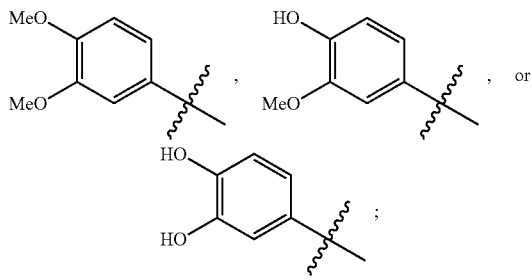

and
when m is 0, W of Formula IIc is not benzyl or

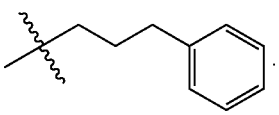 [SMILES: *CCCc1ccccc1]

In some related aspects, the present invention provides a method of modulating lipoxygenase and/or cyclooxygenase activity, comprising contacting said lipoxygenase with a compound or a pharmaceutically acceptable salt thereof of the present invention, or a pharmaceutical composition of the present invention. In some embodiments, the methods described herein prevents and/or treats conditions or disorders mediated or associated with a lipoxygenase for example, 5-lipoxygenase (5-LO). In other embodiments, the methods described herein prevents and/or treats conditions or disorders mediated or associated with a cyclooxygenase, for example, cyclooxygenase 1 (COX-1) and/or cyclooxygenase-2 (COX-2).

In various embodiments, the methods described herein are used to inhibit, or reduce the activity of the lipoxygenase and/or cyclooxygenase in the presence of a compound or pharmaceutically acceptable salt of the present invention.

In a related aspect, the present invention provides a method of treating or lessening the severity of a lipoxygenase and/or a cyclooxygenase mediated disease or condition, comprising administering to the subject in need thereof a compound or a pharmaceutically acceptable salt thereof of the present invention. In some of these embodiments, the lipoxygenase is 5-lipoxygenase (5-LO), and/or the cyclooxygenase is COX-1 and/or the cyclooxygenase is COX-2, or any combination thereof.

In related aspects, the lipoxygenase and/or the cyclooxygenase mediated disease or condition can include inflammation, chronic inflammation, inflammation-associated disorder, metabolic syndrome, pain, headache, fever, arthritis, rheumatoid arthritis, spondyloarthopathies, gouty arthritis, osteoarthritis, systemic lupus erythematosus, juvenile arthritis, asthma, bronchitis, menstrual cramps, tendinitis, bursitis, psoriasis, eczema, burns, dermatitis, inflammatory bowel disease, Crohn's disease, gastritis, irritable bowel syndrome, ulcerative colitis, colorectal cancer, prostate cancer, lung cancer, breast cancer, vascular disease, migraine headache, periarteritisnodosa, thyroiditis, aplastic anemia, Hodgkin's disease, scleredoma, rheumatic fever, type I diabetes, myasthenia gravis, sarcoidosis, nephrotic syndrome, Behcet's syndrome, polymyositis, gingivitis, hypersensitivity, conjunctivitis, swelling occurring after injury, myocardial ischemia, allergic rhinitis, respiratory distress syndrome, endotoxic shock syndrome, atherosclerosis, and stroke.

DETAILED DESCRIPTION OF THE INVENTION

As used herein, the following definitions shall apply unless otherwise indicated.

I. Definitions

For purposes of this invention, the chemical elements are identified in accordance with the Periodic Table of the Elements, CAS version, Handbook of Chemistry and Physics, 95th Ed. Additionally, general principles of organic chemistry are described in "Organic Chemistry", $2^{nd}$ Ed., Thomas Sorrell, University Science Books, Sausalito: 2006, and "March's Advanced Organic Chemistry", 7th Ed., Ed.: Smith, M. B. and March, J., John Wiley & Sons, New York: 2013, the entire contents of which are hereby incorporated by reference.

The term "modulating" as used herein means increasing or decreasing, e.g. activity, by a measurable amount. Compounds that modulate lipoxygenase and/or cyclooxygenase activity by increasing the activity of the lipoxygenase and/or cyclooxygenase enzyme are called agonists. Compounds that modulate lipoxygenase and/or cyclooxygenase activity by decreasing the activity of the lipoxygenase and/or cyclooxygenase enzyme are called antagonists. An agonist interacts with a lipoxygenase and/or cyclooxygenase enzyme to increase the activity of the enzyme. An antagonist interacts with a lipoxygenase and/or cyclooxygenase enzyme and competes with the endogenous ligand(s) or substrate(s) for binding site(s) on the enzyme to decrease the activity of the enzyme.

The phrase "treating or reducing the severity of a lipoxygenase and/or a cyclooxygenase mediated disease" refers both to treatments for diseases that are directly caused by lipoxygenase and/or cyclooxygenase enzyme activities and alleviation of symptoms of diseases not directly caused by lipoxygenase and/or cyclooxygenase enzyme activities. Examples of diseases or conditions whose symptoms may be affected by lipoxygenase and/or cyclooxygenase enzyme activity include, but are not limited to, inflammation, chronic inflammation, inflammation-associated disorder, metabolic syndrome, pain, headache, fever, arthritis, rheumatoid arthritis, spondyloarthopathies, gouty arthritis, osteoarthritis, systemic lupus erythematosus, juvenile arthritis, asthma, bronchitis, menstrual cramps, tendinitis, bursitis, psoriasis, eczema, burns, dermatitis, inflammatory bowel disease, Crohn's disease, gastritis, irritable bowel syndrome, ulcerative colitis, colorectal cancer, prostate cancer, lung cancer, breast cancer, vascular disease, migraine headache, periarteritisnodosa, thyroiditis, aplastic anemia, Hodgkin's disease, sclerodoma, rheumatic fever, type I diabetes, myasthenia gravis, sarcoidosis, nephrotic syndrome, Behcet's syndrome, polymyositis, gingivitis, hypersensitivity, conjunctivitis, swelling occurring after injury, myocardial ischemia, allergic rhinitis, respiratory distress syndrome, endotoxic shock syndrome, atherosclerosis, and stroke.

As described herein, compounds of the invention may optionally be substituted with one or more substituents, such as are illustrated or as exemplified by particular classes, subclasses, and species of the invention described herein.

As used herein the term "CAPE" refers to "caffeic acid phenethyl ester" which has the structure below:

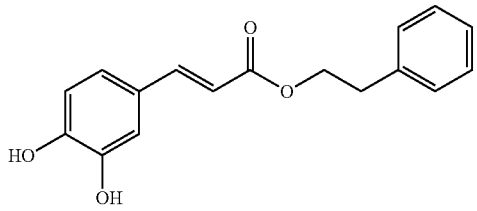 [SMILES: O=C(/C=C/c1ccc(O)c(O)c1)OCCc1ccccc1]

As used herein the term "aliphatic" encompasses the terms alkyl, alkenyl, alkynyl. An aliphatic group can be optionally substituted with one or more of halo, hydroxy, cyano, nitro, cycloaliphatic, heterocycloaliphatic, aryl, heteroaryl, alkylcarbonyl, alkoxy, alkylsulfonyl, alkylsulfanyl, alkylsulfinyl, amino, alkylamino, alkoxycarbonyl, alkylaminocarbonyl, combinations thereof, or the like.

As used herein, an "alkyl" group refers to a saturated aliphatic hydrocarbon group containing 1-8 (e.g., 1-6 or 1-4) carbon atoms. An alkyl group can be straight or branched. Examples of alkyl groups include, but are not limited to, methyl, ethyl, propyl, isopropyl, butyl, isobutyl, sec-butyl, isobutyl, n-pentyl, n-heptyl, or 2-ethylhexyl. An alkyl group can be optionally substituted with one or more substituents as described above.

As used herein, an "alkenyl" group refers to an aliphatic carbon group that contains 2-10 (e.g., 2, 3, 4, 5, 6, 7, 8, 9 or 10) carbon atoms and at least one double bond. Like an alkyl group, an alkenyl group can be straight or branched. Examples of an alkenyl group include, but are not limited to, allyl, isoprenyl, 2-butenyl, and 2-hexenyl. An alkenyl group can be optionally substituted with one or more substituents as described above.

As used herein, an "alkynyl" group refers to an aliphatic carbon group that contains 2-8 (e.g., 2-6 or 2-4) carbon atoms and at least one triple bond. Like an alkyl group, an alkynyl group can be straight or branched. An alkynyl group can be optionally substituted with one or more substituents as described above.

As used herein, the term "alkylene" refers to a bivalent (divalent) alkyl group. Examples of alkylene groups include methylene, ethylene, propylene, n-butylene, and the like. The alkylene is attached to the rest of the molecule through a single bond and to the radical group through a single bond. The points of attachment of the alkylene to the rest of the molecule and to the radical group can be through one carbon or any two carbons within the carbon chain.

As used herein, an "amino" group refers to —NR$^X$R$^Y$ wherein each of R$^X$ and R$^Y$ is independently hydrogen, alkyl, cycloalkyl, sulfonyl, (cycloalkyl)alkyl, aryl, aralkyl, heterocycloalkyl, (heterocycloalkyl)alkyl, heteroaryl, or heteroaralkyl each of which are defined herein and are optionally substituted. When the term "amino" is not the terminal group (e.g., alkylcarbonylamino), it is represented by —NR$^X$—. R$^X$ has the same meaning as defined above.

As used herein, an "aryl" group used alone or as part of a larger moiety as in "aralkyl", "aralkoxy", or "aryloxyalkyl" refers to monocyclic (e.g., phenyl); bicyclic (e.g., indenyl, naphthalenyl, tetrahydronaphthyl, tetrahydroindenyl); tricyclic (e.g., fluorenyl, tetrahydrofluorenyl, anthracenyl, or tetrahydroanthracenyl); or a benzofused group having 3 rings. For example, a benzofused group includes phenyl fused with two or more C$_{4-8}$ carbocyclic moieties. An aryl can be optionally substituted with one or more substituents. Without limitation, an aryl can be optionally substituted with halo, hydroxy, cyano, nitro, aliphatic, cycloaliphatic, aryl, heterocycloaliphatic, heteroaryl, alkylsulfonyl, aliphaticaminocarbonyl, alkoxy, aminocarbonyl, alkoxycarbonyl, heteroarylcarbonyl, (heterocycloaliphatic)carbonyl, (heteroarylamino)carbonyl, cycloalkylcarbonyl, alkylcarbonylamino, cycloaliphaticsulfonyl, heterocycloaliphaticsulfonyl, alkylsulfanyl, alkylsulfonyl, (alkoxyalkyl)aminocarbony, combinations thereof, or the like.

As used herein, an "araliphatic" group refers to an aliphatic group (e.g., a C$_{1-4}$ alkyl group, a C$_{1-4}$ alkenyl group, or a C$_{1-4}$ alkynyl group) that is substituted with an aryl group. Both "aliphatic" and "aryl" have been defined above.

As used herein, an "aralkyl" group refers to an alkyl group (e.g., a C$_{1-4}$ alkyl group) that is substituted with an aryl group. Both "alkyl" and "aryl" are defined herein. An example of an aralkyl group is benzyl.

As used herein, a "bicyclic ring system" includes 5-12 (e.g., 7, 8, 9, 10, or 11) membered structures that form two rings, wherein the two rings have at least one atom in common (e.g., 2 atoms in common). Bicyclic ring structures include bicycloaliphatics (e.g., bicycloalkyl or bicycloalkenyl), bicycloheteroaliphatics (e.g., bicycloheteroalkyl or bicycloheteroalkenyl), bicyclic aryls, and bicyclic heteroaryls. Bicyclic ring systems also include bridged bicyclic rings and fused bicyclic rings (e.g., benzo fused).

The term "cycloaliphatic" means a saturated or partially unsaturated monocyclic, bicyclic, or tricyclic hydrocarbon ring that has a single point of attachment to the rest of the molecule. Cycloaliphatic rings are 3-8 membered monocyclic rings (e.g., 3-6 membered rings). Cycloaliphatic rings also include 5-12 membered bicyclic rings. Bicyclic cycloaliphatic (i.e., bicycloaliphatic rings) include bridged bicyclic cycloaliphatic rings and cycloaliphatic fused bicyclic rings. A cycloaliphatic group also encompasses a "cycloalkyl" group and a "cycloalkenyl" group.

Examples of substituents on a cycloaliphatic group include, without limitation, halo, hydroxy, cyano, nitro, aliphatic, alkoxy, alkoxyimino, alkoxyamino, oxo, aryloxyimmino, As used herein, a "cycloalkyl" group refers to a saturated carbocyclic mono-, bi-, or tri-, or multicyclic (fused or bridged) ring of 3-10 (e.g., 5-10) carbon atoms. Without limitation, examples of monocyclic cycloalkyl groups include cyclopropyl, cyclobutyl, cyclopentyl, cyclohexyl, cycloheptyl, or the like. Examples of bicyclic cycloalkyl groups include bridged bicyclic cycloalkyls and fused bicyclic cycloalkyls. Without limitation, bicyclic cycloalkyls include octahydro-indenyl, decahydro-naphthyl, bicyclo[3.2.1]octyl, bicyclo[2.2.2]octyl, bicyclo[3.3.1]nonyl, bicyclo[3.3.2.]decyl, bicyclo[2.2.2]octyl, bicycle[2.2.1]heptanyl, bicycle[3.1.1]heptanyl, or the like. Without limitation, multicyclic groups include adamantyl, cubyl, norbornyl, or the like. Cycloalkyl rings can be optionally substituted at any chemically viable ring position.

As used herein, a "cycloalkenyl" group refers to a partially unsaturated carbocyclic mono-, bi-, or tri-, or multicyclic (fused or bridged) ring of 3-10 (e.g., 5-10) carbon atoms. Without limitation, examples of monocyclic cycloalkenyl groups include cyclopropenyl, cyclobutenyl, cyclopentenyl, cyclohexenyl, cycloheptenyl, or the like. Without limitation, bicyclic cycloalkenyl groups include, for example, bicyclo[3.2.1]octenyl, bicyclo[2.2.2]octenyl, bicyclo[3.3.1]nonenyl, bicyclo[3.3.2.]decenyl, bicycle[2.2.1]heptenyl, or bicycle[3.1.1]heptenyl.

As used herein, the term "heterocycloaliphatic" and "heterocyclic" encompasses a heterocycloalkyl group and a heterocycloalkenyl group. Heterocycloaliphatic groups include 3-10 membered monocyclic ring structures having 1-3 heteroatoms. Heterocycloaliphatic groups also include 5-10 membered bicyclic heterocycloaliphatics (i.e., bicycloheterocycloaliphatics). Bicycloheteroaliphatic groups include bridged bicyclic structures, and fused bicyclic structures. Fused bicyclic structures can include a monocyclic heterocycloaliphatic fused to a monocyclic cycloaliphatic ring or a monocyclic heterocycloaliphatic ring.

As used herein, a "heterocycloalkyl" group refers to a 3-10 membered mono or bicyclic (fused or bridged) (e.g., 5 to 10 membered mono or bicyclic) saturated ring structure, in which one or more of the ring atoms is a heteroatom (e.g., N, O, S, or combinations thereof). Bicyclic heterocycloalkyls include bridged and fused bicyclic heterocycloalkyls. Non-limiting examples of heterocycloalkyls include optionally substituted piperidinyl, piperazinyl, tetrahydropyranyl, tetrahydrofuranyl, 1,4-dioxolanyl, 1,4-dithianyl, 1,3-dioxolanyl, oxazolidyl, isoxazolidyl, morpholinyl, thiomorpholinyl, octahydro-benzofuranyl, octahydro-chromenyl, octahydro-thiochromenyl, octahydro-indolyl, octahydropyrindinyl, decahydro-quinolinyl, octahydro-benzo[b]thiopheneyl, 2-oxa-bicyclo[2.2.2]octyl, 1-aza-bicyclo[2.2.2]octyl, 3-aza-bicyclo[3.2.1]octanyl, 2,6-dioxa-tricyclo[3.3.1.0$^{3.7}$]nonyl, or tropane. A monocyclic heterocycloalkyl group may be fused with a phenyl moiety such as tetrahydroisoquinoline. Heterocycloalkyl ring structures can be optionally substituted at any chemically viable position on the ring or rings.

A heterocycloalkyl group can be substituted at any chemically feasible position. Heterocycloalkyl substituents, without limitation, include halo, hydroxy, cyano, alkoxy, alkoxycarbonyl, aliphatic (e.g., alkyl, alkenyl, or alkynyl), cycloaliphatic, heterocycloaliphatic, aryl, heteroaryl, heterocycloaliphatic, arylcarbonyl, combinations thereof, or the like.

A "heterocycloalkenyl" group, as used herein, refers to a mono- or bicyclic (e.g., 5- to 10-membered mono- or bicyclic) non-aromatic ring structure having one or more double bonds, and wherein one or more of the ring atoms is a heteroatom (e.g., N, O, or S). Bicyclic heterocycloalkenyls include bridged and fused bicyclic heterocycloalkenyls. Examples of heterocycloalkenyls include 2-pyrrolyl, 3-pyrrolyl, 2-imidazolyl, or 2-pyrazolyl. Monocyclic heterocycloaliphatics are numbered according to standard chemical nomenclature. Heterocycloalkenyl substituents, without limitation, include halo, hydroxy, cyano, alkoxy, alkoxycarbonyl, aliphatic (e.g., alkyl, alkenyl, or alkynyl), cycloaliphatic, heterocycloaliphatic, aryl, heteroaryl, heterocycloaliphatic, arylcarbonyl, combinations thereof, or the like.

A "heteroaryl" group, as used herein, refers to a monocyclic, bicyclic, or tricyclic ring systems having 4 to 15 ring atoms wherein one or more of the ring atoms is a heteroatom (e.g., N, O, S, or combinations thereof) and wherein one or more rings of the bicyclic or tricyclic ring structure is aromatic. A heteroaryl group includes a benzofused ring system having 2 to 3 rings. For example, a benzofused group includes benzo fused with one or two $C_{4-8}$ heterocyclic moieties (e.g., indolizyl, indolyl, isoindolyl, 3H-indolyl, indolinyl, benzo[b]furyl, benzo[b]thiopheneyl, quinolinyl, or isoquinolinyl). Some examples of heteroaryl are azetidinyl, pyridinyl, 1H-indazolyl, furyl, pyrrolyl, thienyl, thiazolyl, oxazolyl, imidazolyl, triazolyl, tetrazolyl, benzofuryl, isoquinolinyl, benzthiazolyl, xanthene, thioxanthene, phenothiazine, dihydroindole, benzo[1,3]dioxole, benzo [b]furyl, benzo[b]thiopheneyl, indazolyl, benzimidazolyl, benzthiazolyl, puryl, cinnolinyl, quinolinyl, cinnolinyl, phthalazyl, quinazolinyl, quinoxalinyl, isoquinolinyl, 4H-quinolizyl, benzo-1,2,5-thiadiazolyl, or 1,8-naphthyridyl. A heteroaryl can be optionally substituted at any chemically feasible position.

Without limitation, monocyclic heteroaryls include furyl, thiopheneyl, 2H-pyrrolyl, pyrrolyl, oxazolyl, thiazolyl, imidazolyl, pyrazolyl, isoxazolyl, isothiazolyl, 1,3,4-thiadiazolyl, 2H-pyranyl, 4-H-pyranyl, pyridinyl, pyridazinyl, pyrimidyl, pyrazolyl, pyrazyl, or 1,3,5-triazyl.

Without limitation, bicyclic heteroaryls include indolizyl, indolyl, isoindolyl, 3H-indolyl, indolinyl, benzo[b]furyl, benzo[b]thiopheneyl, quinolinyl, isoquinolinyl, indolizyl, isoindolyl, indazolyl, benzimidazolyl, benzthiazolyl, purinyl, 4H-quinolizyl, quinolinyl, isoquinolinyl, cinnolinyl, phthalazyl, quinazolinyl, quinoxalinyl, 1,8-naphthyridyl, or pteridyl.

Without limitation, a heteroaryl can be substituted with halo, hydroxy, cyano, aliphatic, cycloaliphatic, heterocycloaliphatic, aryl, heteroaryl, arylcarbonyl, arylcarbonylamino, aliphaticaminocarbonyl, alkoxy, combinations thereof, or the like.

A "heteroaraliphatic" group, as used herein, refers to an aliphatic group (e.g., $C_{1-4}$ alkyl group, $C_{1-4}$ alkenyl group, or $C_{1-4}$ alkynyl group) that is substituted with a heteroaryl group. Both "aliphatic" and "heteroaryl" have been defined above.

A "heteroaralkyl" group, as used herein, refers to an alkyl group (e.g., a $C_{1-4}$ alkyl group) that is substituted with a heteroaryl group. Both "alkyl" and "heteroaryl" have been defined above.

As used herein, "cyclic group" includes mono-, bi-, and tri-cyclic structures including cycloaliphatic, heterocycloaliphatic, aryl, or heteroaryl, each of which has been previously defined.

As used herein, an "acyl" group refers to a formyl group or alkyl-C(=O)— (also referred to as "alkylcarbonyl") where "alkyl" has been defined previously. Acetyl and pivaloyl are examples of acyl groups.

As used herein, a "carbonyl" group, when used alone or as part of another structure refers to the structure —C(O)—.

As used herein, a "carbamoyl" group refers to a group having the structure —O—CO—NR$^X$R$^Y$ or —NR$^X$—CO—O—R$^Z$ where in R$^X$ and R$^Y$ have been defined above and R$^Z$ can be alkyl, aryl, aralkyl, cycloalkyl, heterocycloalkyl, heteroaryl, or heteroaralkyl.

As used herein, a "carboxy" and a "sulfo" group refer to —C(O)OH or —C(O)OR$^X$ and —SO$_3$H or —SO$_3$R$^X$, respectively.

As used herein, an "alkoxy" group refers to an alkyl-O- group where "alkyl" has been defined previously. Moreover an alkoxy group includes structures comprising two alkoxy groups on the same atom or adjacent atoms that form a ring together with the atom(s) to which they are bound.

As used herein, an "alkoxycarbonyl" group refers to the structure —C(O)O-alkyl.

As used herein, a "nitro" group refers to —N⁺(O)O⁻.

As used herein, a "sulfoxy" group refers to —O—SO—$R^X$ or —SO—O—$R^X$, where $R^X$ has been defined above.

As used herein, a "mercapto" group refers to —SH.

As used herein, a "sulfonyl" group refers to —S(O)$_2$—.

As used herein a "sulfinyl" group refers to —S(O)—.

As used herein a "sulfanyl" group refers to —S—.

As used herein, a "halogen" or "halo" group refers to fluorine, chlorine, bromine or iodine.

As used herein, a "haloaliphatic" group refers to an aliphatic group substituted with 1-3 halogen. For instance, the term haloalkyl includes the group —CF$_3$.

As used herein, a "sulfamoyl" group refers to the structure —S(O)$_2$—NR$^X$R$^Y$ or —NR$^X$—S(O)$_2$—R$^Z$ where in R$^X$, R$^Y$, and R$^Z$ have been defined above.

As used herein, a "sulfamide" group refers to the structure —NR$^X$—S(O)$_2$—NR$^Y$R$^Z$ wherein R$^X$, R$^Y$, and R$^Z$ have been defined above.

As used herein, a "carbonylamino" group used alone or in connection with another group refers to an amido group such as R$^X$—C(O)—NR$^X$—. For instance an alkylcarbonylamino includes alkyl-C(O)—NR$^X$—, wherein R$^X$ has been defined above.

As used herein, a "aminocarbonyl" group used alone or in connection with another group refers to an amido group such as N(R$^X$)$_2$—C(O)—.

As used herein, an "alkoxycarbonyl" used alone or in connection with another group refers to a carbonyl group such as alkyl-O—C(O)—.

As used herein, an "alkoxyalkyl" refers to an alkyl group such as alkyl-O-alkyl-, wherein alkyl has been defined above.

As used herein, an "aminocarbonyl" refers to an amido group such as —NR$^X$—C(O)—, wherein R$^X$ has been defined above.

As used herein, an "aminosulfonyl" refers to the structure —N(R$^X$)$_2$—S(O)$_2$—, wherein R$^X$ has been defined above.

As used herein, an "oxo" refers to =O.

As used herein, an "aminoalkyl" refers to the structure N(R$^X$)$_2$-alkyl-.

As used herein, a "cyanoalkyl" refers to the structure (CN)-alkyl-.

As used herein, an "alkylsulfonyl" group refers to the structure alkyl-S(O)$_2$—.

As used herein, a "sulfonylamino" group refers to the structure R$^X$—S(O)$_2$—N(R$^X$)$_2$—, wherein R$^X$ has been defined above.

As used herein, an "imino" group refers to the functional group =N— and covers the structure =N—R$^X$ and oximes having the structure =N—OR$^X$ wherein R$^X$ is defined above.

As used herein, a "hydroxy" group refers to the structure —OH.

As used herein, a "guanidinyl" group refers to the structure NH$_2$C(NH)NH—.

As used herein, an "aliphatic chain" refers to a branched or straight aliphatic group (e.g., alkyl groups, alkenyl groups, or alkynyl groups). A straight aliphatic chain has the structure —[CH$_2$]$_v$—, where v is 1-6. A branched aliphatic chain is a straight aliphatic chain that is substituted with one or more aliphatic groups. A branched aliphatic chain has the structure —[CHQ]$_v$— where Q is hydrogen or an aliphatic group; however, Q shall be an aliphatic group in at least one instance. The term aliphatic chain includes alkyl chains, alkenyl chains, and alkynyl chains, where alkyl, alkenyl, and alkynyl are defined above.

As used herein, a "urea" group refers to the structure —NR$^X$—CO—NR$^Y$R$^Z$ and a "thiourea" group refers to the structure —NR$^X$—CS—NR$^Y$R$^Z$, R$^X$, R$^Y$, and R$^Z$ have been defined above.

As used herein the term "Me" means "methyl" and is used interchangeably with "—CH$_3$."

As used herein the term "Et" means "ethyl" and is used interchangeably with "—CH$_2$CH$_3$."

As used herein the term "Pr" means "propyl" and "i-Pr" means "isopropyl" and are used interchangeably with "—CH$_2$CH$_2$CH$_3$" and "—CHCH$_3$(CH$_3$)", respectively.

As used herein the term "Ph" means "phenyl" and is used interchangeably with

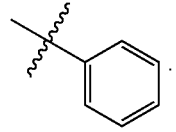 [SMILES: *c1ccccc1]

In general, the term "vicinal" refers to the placement of substituents on a group that includes two or more carbon atoms, wherein the substituents are attached to adjacent carbon atoms.

In general, the term "geminal" refers to the placement of substituents on a group that includes two or more carbon atoms, wherein the substituents are attached to the same carbon atom.

In general, the term "substituted," whether preceded by the term "optionally" or not, refers to the replacement of hydrogen radicals in a given structure with the radical of a specified substituent. Specific substituents are described above in the definitions and below in the description of compounds and examples thereof. Unless otherwise indicated, an optionally substituted group may have a substituent at each substitutable position of the group, and when more than one position in any given structure may be substituted with more than one substituent selected from a specified group, the substituent may be either the same or different at every position. A ring substituent, such as a heterocycloalkyl, may be bound to another ring, such as a cycloalkyl, to form a spiro-bicyclic ring system, e.g., both rings share one common atom. As one of ordinary skill in the art will recognize, combinations of substituents envisioned by this invention are those combinations that result in the formation of stable or chemically feasible compounds.

The phrase: "stable or chemically feasible," as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

As used herein, an "effective amount" is defined as the amount required to confer a therapeutic effect on the treated patient, and is typically determined based on age, surface area, weight, and condition of the patient. The interrelationship of dosages for animals and humans (based on milligrams per meter squared of body surface) is described by Freireich et al., Cancer Chemother. Rep., 50: 219 (1966). Body surface area may be approximately determined from height and weight of the patient. See, e.g., Scientific Tables, Geigy Pharmaceuticals, Ardsley, New York, 537 (1970). As used herein, "patient" refers to a mammal, including a human.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays.

II. Embodiments

The invention also includes specific compounds, which are provided in Table 1 and Table 2 below.

TABLE 1

| Cmp # | Name | Structure |
|---|---|---|
| 1 | 4-phenylbutyl 3-(3,4-dihydroxyphenyl)propanoate | 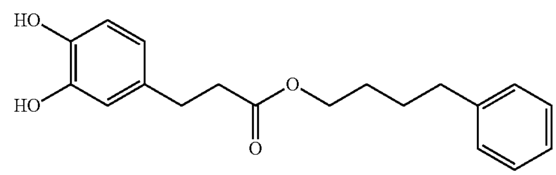 [SMILES: O=C(CCc1ccc(O)c(O)c1)OCCCCc1ccccc1] |
| 2 | 5-phenylpentyl 3-(3,4-dihydroxyphenyl)propanoate | 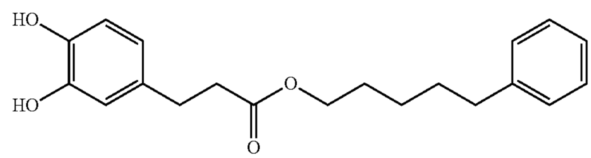 [SMILES: O=C(CCc1ccc(O)c(O)c1)OCCCCCc1ccccc1] |
| 3 | 6-phenylhexyl 3-(3,4-dihydroxyphenyl)propanoate | 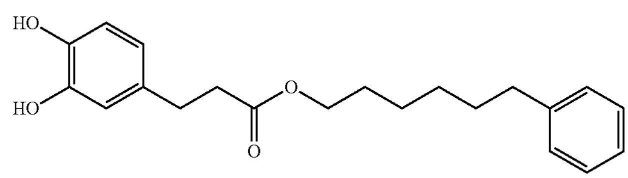 [SMILES: O=C(CCc1ccc(O)c(O)c1)OCCCCCCc1ccccc1] |
| 4 | (E)-(Z)-3-phenylallyl 3-(3,4-dihydroxyphenyl)acrylate | 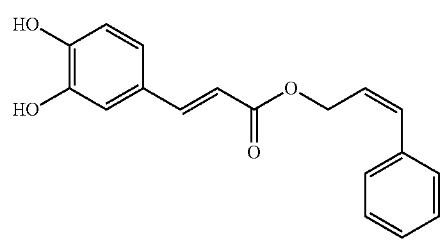 [SMILES: O=C(/C=C/c1ccc(O)c(O)c1)OC/C=C\c1ccccc1] |
| 5 | (E)-3-phenylpropyl 3-(2-hydroxyphenyl)acrylate | 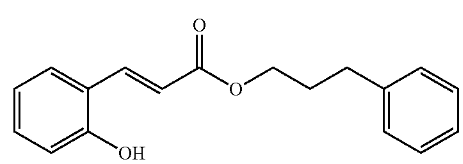 |
| 6 | (E)-3-phenylpropyl 3-(4-hydroxy-3,5-dimethoxyphenyl)acrylate | 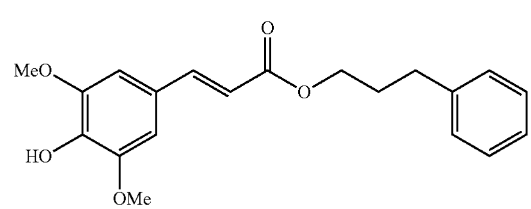 [SMILES: COc1cc(/C=C/C(=O)OCCCc2ccccc2)cc(OC)c1O] |

TABLE 1-continued

| Cmp # | Name | Structure |
|---|---|---|
| 7 | (E)-phenethyl 3-(3,4-dichlorophenyl)acrylate | 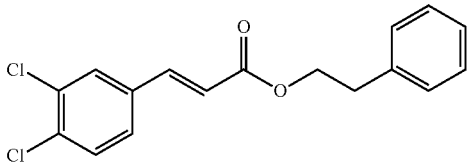 [SMILES: O=C(/C=C/c1ccc(Cl)c(Cl)c1)OCCc1ccccc1] |
| 8 | (E)-phenethyl 3-(naphthalen-2-yl)acrylate | 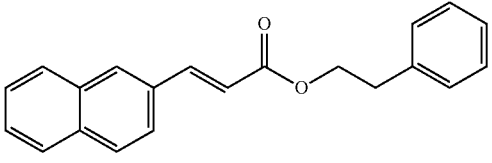 [SMILES: O=C(/C=C/c1ccc2ccccc2c1)OCCc1ccccc1] |
| 9 | (E)-phenethyl 3-(3,5-dimethoxyphenyl)acrylate | 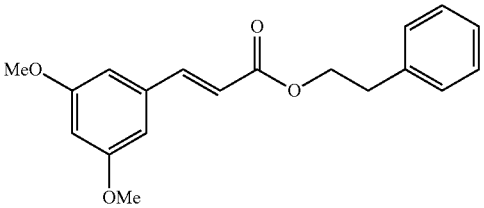 [SMILES: COc1cc(/C=C/C(=O)OCCc2ccccc2)cc(OC)c1] |
| 10 | (E)-3-phenylpropyl 3-(3,5-dimethoxyphenyl)acrylate | 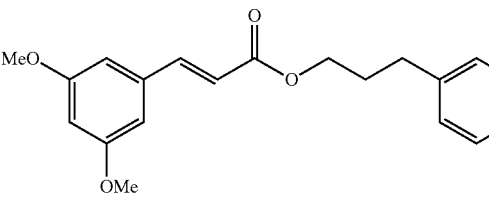 |
| 11 | (E)-3-phenylpropyl 3-(2,5-dimethoxyphenyl)acrylate | 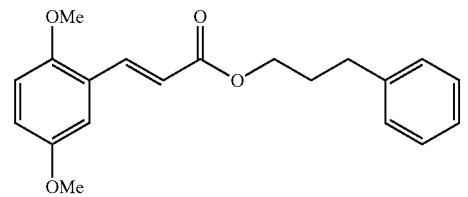 [SMILES: COc1ccc(OC)c(/C=C/C(=O)OCCCc2ccccc2)c1] |
| 12 | (E)-3-phenylpropyl 3-(2,3-dimethoxyphenyl)acrylate | 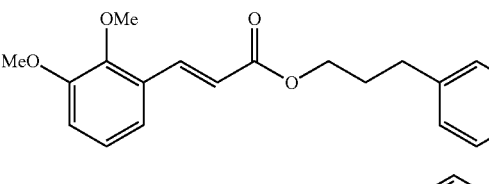 |
| 13 | (E)-phenethyl 3-(3,5-bis(trifluoromethyl)phenyl)acrylate | 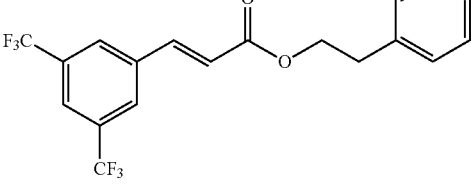 |
| 14 | (E)-3-phenylpropyl 3-(2,4-dihydroxyphenyl)acrylate | 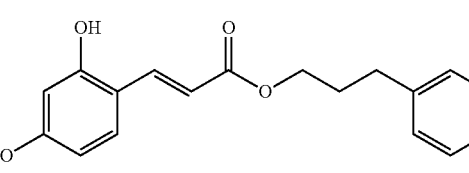 | or a pharmaceutically acceptable salt thereof.

TABLE 2

| Cmp # | Name | Structure |
|---|---|---|
| 15 | (E)-isopropyl 3-(3,4-dihydroxyphenyl)acrylate | 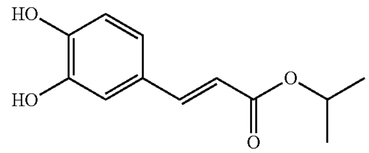 [SMILES: CC(C)OC(=O)/C=C/c1ccc(O)c(O)c1] |
| 16 | (E)-isopropyl 3-(3,4-dihydroxyphenyl)acrylate | 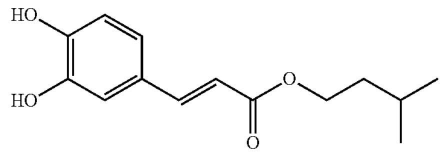 |
| 17 | (E)-3-methylbut-3-en-1-yl 3-(3,4-dihydroxyphenyl)acrylate | 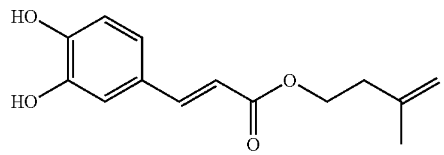 [SMILES: C=C(C)CCOC(=O)/C=C/c1ccc(O)c(O)c1] |
| 18 | (E)-phenyl 3-(3,4-dihydroxyphenyl)acrylate | 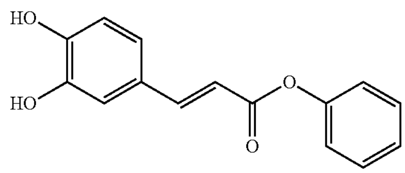 [SMILES: O=C(/C=C/c1ccc(O)c(O)c1)Oc1ccccc1] |
| 19 | (E)-benzyl 3-(3,4-dihydroxyphenyl)acrylate | 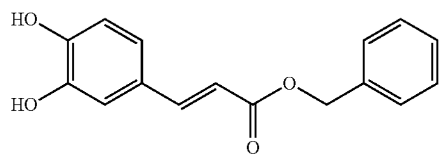 [SMILES: O=C(/C=C/c1ccc(O)c(O)c1)OCc1ccccc1] |
| 20 | (E)-4-fluorophenethyl 3-(3,4-dihydroxyphenyl)acrylate | 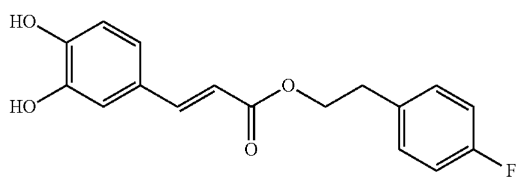 [SMILES: O=C(/C=C/c1ccc(O)c(O)c1)OCCc1ccc(F)cc1] |
| 21 | (E)-4-methylphenethyl 3-(3,4-dihydroxyphenyl)acrylate | 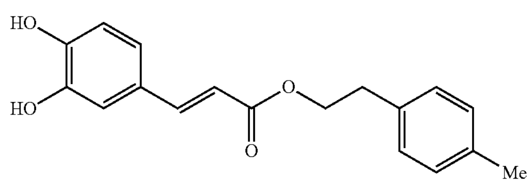 [SMILES: Cc1ccc(CCOC(=O)/C=C/c2ccc(O)c(O)c2)cc1] |
| 22 | (E)-4-methoxyphenethyl 3-(3,4-dihydroxyphenyl)acrylate | 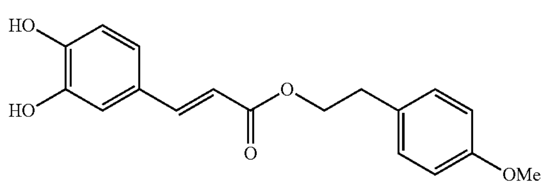 [SMILES: COc1ccc(CCOC(=O)/C=C/c2ccc(O)c(O)c2)cc1] |
| 23 | (E)-4-nitrophenethyl 3-(3,4-dihydroxyphenyl)acrylate | 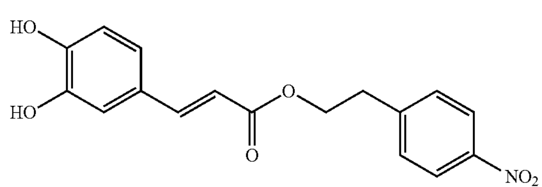 [SMILES: O=C(/C=C/c1ccc(O)c(O)c1)OCCc1ccc([N+](=O)[O-])cc1] |

TABLE 2-continued

| Cmp # | Name | Structure |
|---|---|---|
| 24 | (E)-2-cyclohexylethyl 3-(3,4-dihydroxyphenyl)acrylate | 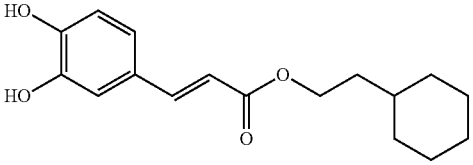 [SMILES: O=C(/C=C/c1ccc(O)c(O)c1)OCCC1CCCCC1] |
| 25 | (E)-3-phenylpropyl 3-(3,4-dihydroxyphenyl)acrylate | 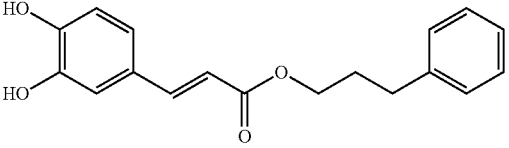 [SMILES: O=C(/C=C/c1ccc(O)c(O)c1)OCCCc1ccccc1] |
| 26 | (E)-2-(naphthalen-2-yl)ethyl 3-(3,4-dihydroxyphenyl)acrylate | 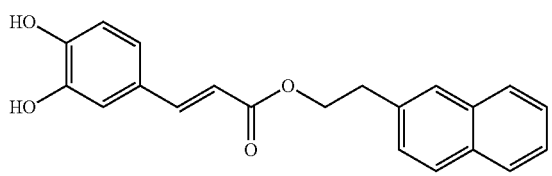 [SMILES: O=C(/C=C/c1ccc(O)c(O)c1)OCCc1ccc2ccccc2c1] |
| 27 | (E)-2,2-diphenylethyl 3-(3,4-dihydroxyphenyl)acrylate | 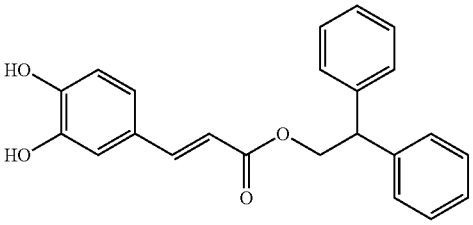 [SMILES: O=C(/C=C/c1ccc(O)c(O)c1)OCC(c1ccccc1)c1ccccc1] |
| 28 | (E)-3-methylbut-2-en-1-yl 3-(3,4-dihydroxyphenyl)acrylate | 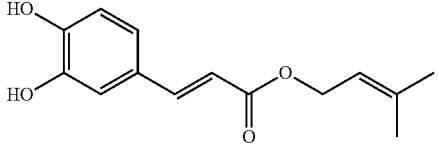 [SMILES: CC(C)=CCOC(=O)/C=C/c1ccc(O)c(O)c1] |
| 29 | (E)-prop-2-yn-1-yl 3-(3,4-dihydroxyphenyl)acrylate | 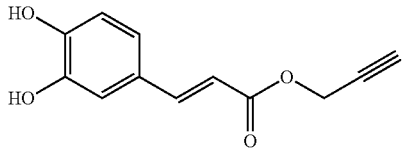 [SMILES: C#CCOC(=O)/C=C/c1ccc(O)c(O)c1] |
| 30 | (E)-allyl 3-(3,4-dihydroxyphenyl)acrylate | 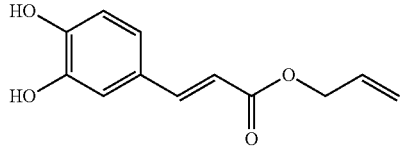 [SMILES: C=CCOC(=O)/C=C/c1ccc(O)c(O)c1] |
| 31 | (E)-cinnamyl 3-(3,4-dihydroxyphenyl)acrylate | 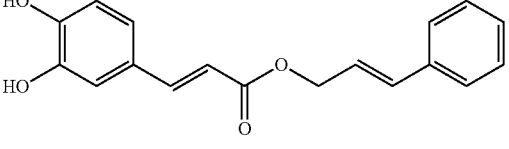 |
| 32 | phenethyl 3-(3,4-dihydroxyphenyl)propanoate | 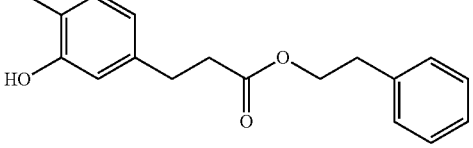 |

TABLE 2-continued

| Cmp # | Name | Structure |
|---|---|---|
| 33 | 3-phenylpropyl 3-(3,4-dihydroxyphenyl)propanoate | 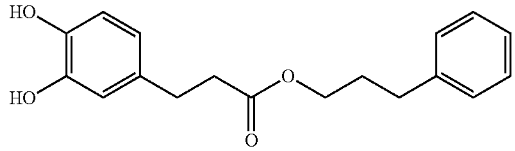 [SMILES: O=C(CCc1ccc(O)c(O)c1)OCCCc1ccccc1] |
| 34 | phenethyl 2-(3,4-dihydroxyphenyl)acetate | 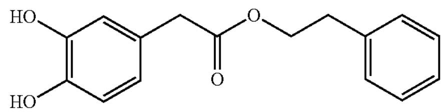 [SMILES: O=C(Cc1ccc(O)c(O)c1)OCCc1ccccc1] |
| 35 | 3-phenylpropyl 2-(3,4-dihydroxyphenyl)acetate | 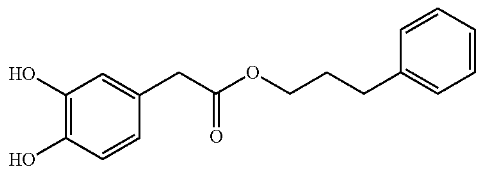 [SMILES: O=C(Cc1ccc(O)c(O)c1)OCCCc1ccccc1] |
| 36 | phenethyl 3,4-dihydroxybenzoate | 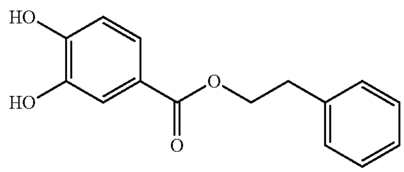 [SMILES: O=C(OCCc1ccccc1)c1ccc(O)c(O)c1] |
| 37 | 3-phenylpropyl 3,4-dihydroxybenzoate | 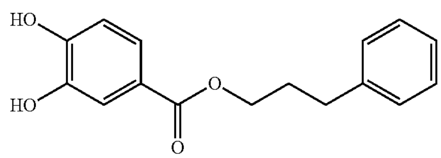 [SMILES: O=C(OCCCc1ccccc1)c1ccc(O)c(O)c1] |
| 38 | phenethyl 3,4,5-trihydroxybenzoate | 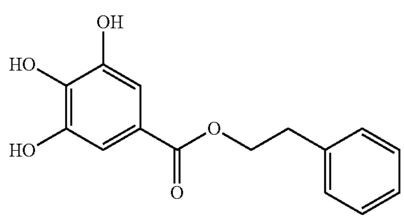 [SMILES: O=C(OCCc1ccccc1)c1cc(O)c(O)c(O)c1] |
| 39 | (E)-4-phenylbutyl 3-(3,4-dihydroxyphenyl)acrylate | 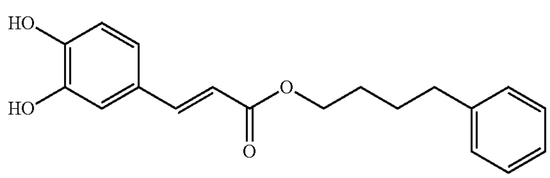 [SMILES: O=C(/C=C/c1ccc(O)c(O)c1)OCCCCc1ccccc1] |
| 40 | (E)-5-phenylpentyl 3-(3,4-dihydroxyphenyl)acrylate | 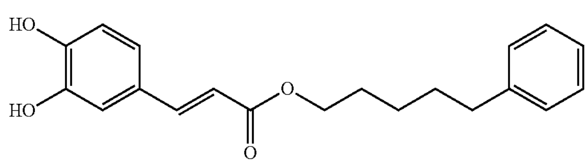 [SMILES: O=C(/C=C/c1ccc(O)c(O)c1)OCCCCCc1ccccc1] |
| 41 | (E)-6-phenylhexyl 3-(3,4-dihydroxyphenyl)acrylate | 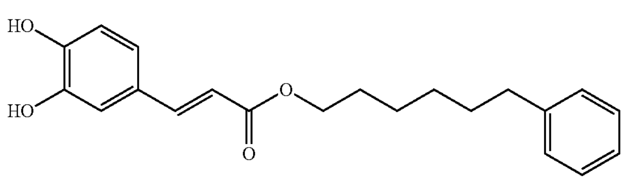 [SMILES: O=C(/C=C/c1ccc(O)c(O)c1)OCCCCCCc1ccccc1] |

TABLE 2-continued

| Cmp # | Name | Structure |
|---|---|---|
| 42 | (E)-phenethyl 3-(3-hydroxy-4-methoxyphenyl)acrylate | 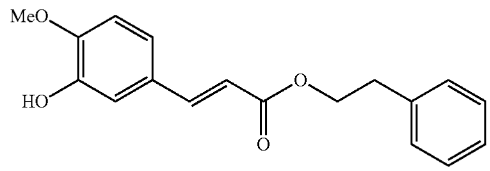 [SMILES: COc1ccc(/C=C/C(=O)OCCc2ccccc2)cc1O] |
| 43 | (E)-3-phenylpropyl 3-(3-hydroxy-4-methoxyphenyl)acrylate | 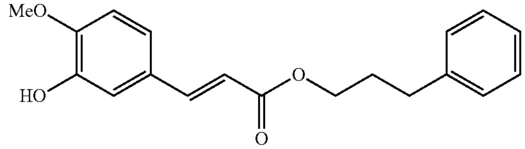 [SMILES: COc1ccc(/C=C/C(=O)OCCCc2ccccc2)cc1O] |
| 44 | (E)-phenethyl 3-(2,3-dihydrobenzo[b][1,4]dioxin-6-yl)acrylate | 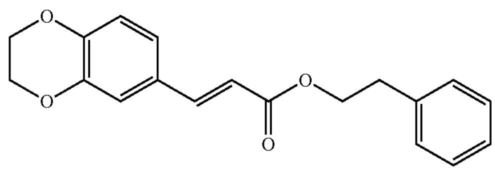 [SMILES: O=C(/C=C/c1ccc2c(c1)OCCO2)OCCc1ccccc1] |
| 45 | (E)-phenethyl 3-(4-hydroxy-3,5-dimethoxyphenyl)acrylate | 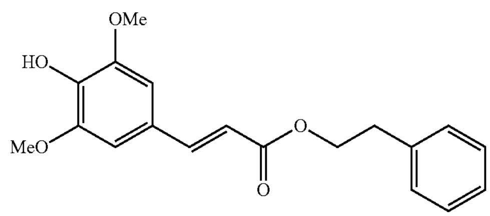 [SMILES: COc1cc(/C=C/C(=O)OCCc2ccccc2)cc(OC)c1O] |
| 46 | (E)-phenethyl 3-(2-hydroxyphenyl)acrylate | 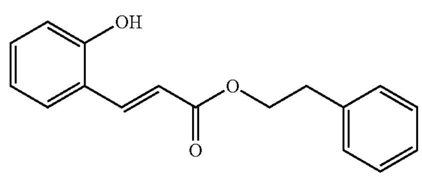 [SMILES: O=C(/C=C/c1ccccc1O)OCCc1ccccc1] |
| 47 | (E)-phenethyl 3-(3-hydroxyphenyl)acrylate | 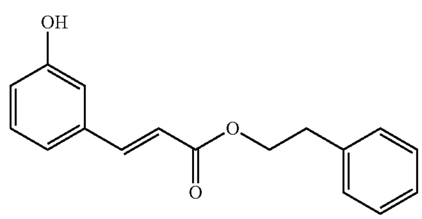 [SMILES: O=C(/C=C/c1cccc(O)c1)OCCc1ccccc1] |
| 48 | (E)-phenethyl 3-(4-hydroxyphenyl)acrylate | 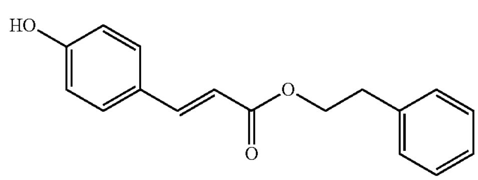 [SMILES: O=C(/C=C/c1ccc(O)cc1)OCCc1ccccc1] |
| 49 | (E)-3-phenylpropyl 3-(4-hydroxyphenyl)acrylate | 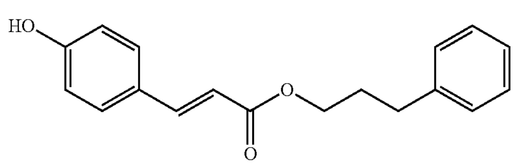 [SMILES: O=C(/C=C/c1ccc(O)cc1)OCCCc1ccccc1] |

TABLE 2-continued

| Cmp # | Name | Structure |
|---|---|---|
| 50 | (E)-3-phenylpropyl 3-(4-hydroxy-3-methoxyphenyl)acrylate | 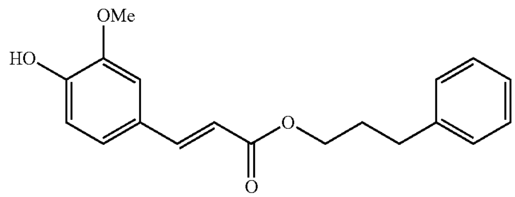 [SMILES: COc1cc(/C=C/C(=O)OCCCc2ccccc2)ccc1O] |
| 51 | (E)-phenethyl 3-(2,5-dimethoxyphenyl)acrylate | 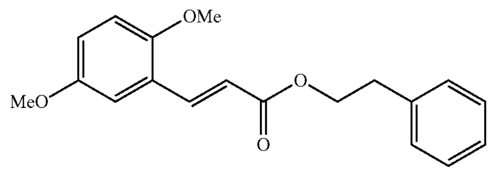 [SMILES: COc1ccc(OC)c(/C=C/C(=O)OCCc2ccccc2)c1] |
| 52 | (E)-phenethyl 3-(2,3-dimethoxyphenyl)acrylate | 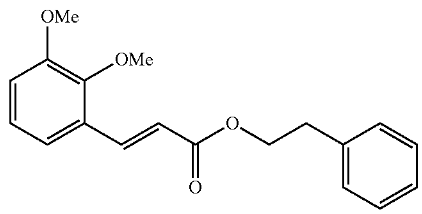 [SMILES: COc1cccc(/C=C/C(=O)OCCc2ccccc2)c1OC] |
| 53 | (E)-phenethyl 3-(3,4,5-trimethoxyphenyl)acrylate | 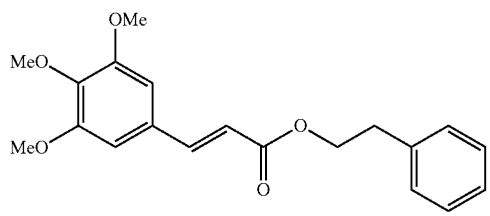 [SMILES: COc1cc(/C=C/C(=O)OCCc2ccccc2)cc(OC)c1OC] |
| 54 | (E)-phenethyl 3-(2,4-dihydroxyphenyl)acrylate | 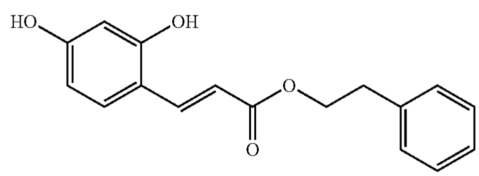 [SMILES: O=C(/C=C/c1ccc(O)cc1O)OCCc1ccccc1] |
| 55 | (E)-3-(3,4-dihydroxyphenyl)-N-(3-phenylpropyl)acrylamide | 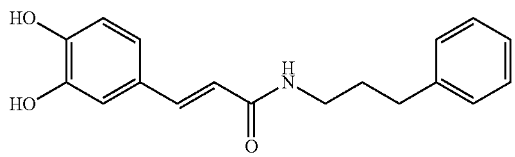 [SMILES: O=C(/C=C/c1ccc(O)c(O)c1)NCCCc1ccccc1] |
| 56 | (E)-3-(3,4-dihydroxyphenyl)-N-(4-phenylbutyl)acrylamide | 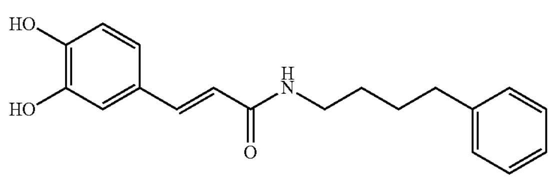 [SMILES: O=C(/C=C/c1ccc(O)c(O)c1)NCCCCc1ccccc1] |
| 57 | (E)-3-(3,4-dihydroxyphenyl)acrylaldehyde | 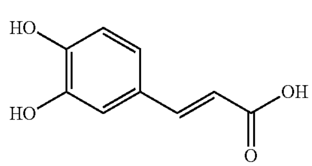 [SMILES: O=C(O)/C=C/c1ccc(O)c(O)c1] |

TABLE 2-continued

| Cmp # | Name | Structure |
|---|---|---|
| 58 | (E)-4-(3-hydroxyprop-1-en-1-yl)benzene-1,2-diol | 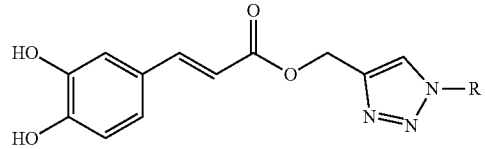 |
| 59 | (E)-1-(3,4-dihydroxyphenyl)-5-phenylpent-1-en-3-one | 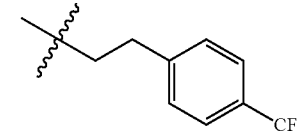 | or a pharmaceutically acceptable salt thereof.

In one aspect, the invention includes a compound having the formula IIIa:

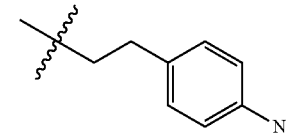

Formula IIIa or a pharmaceutically acceptable salt thereof,
wherein R is X—Y;
X is a bivalent $C_{1-6}$ alkyl group; and
Y is H, —COOH, or a 5-6 membered aryl group optionally substituted with one or more substituents selected from the group consisting of halo, nitro, cyano, $CF_3$, $C_{1-6}$ alkoxy, and hydroxyl.

In one embodiment, X is selected from the group consisting of methylene, ethylene, propylene, isopropylene, butylene, isobutylene, and n-hexylene.

In another embodiment, Y is phenyl, optionally substituted with the group consisting of halo, nitro, cyano, $CF_3$, $C_{1-6}$ alkoxy, and hydroxyl.

In some embodiments, the compound of formula IIIa is selected from the compounds listed in Table 3.

TABLE 3

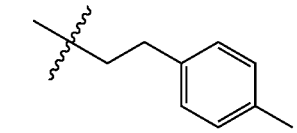 [SMILES: *CCc1ccc(C)cc1]

| Compound | R |
|---|---|
| 60 | $CH_2Ph$ |
| 61 | $CH_2CH_2Ph$ |
| 62 | $CH_2CH_2CH_2Ph$ |
| 63 | 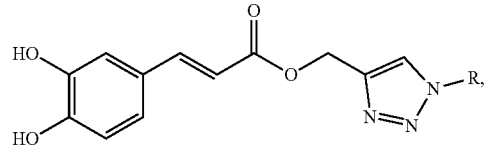 |

TABLE 3-continued

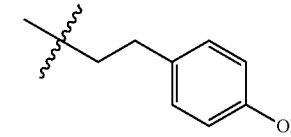

| Compound | R |
|---|---|
| 64 | 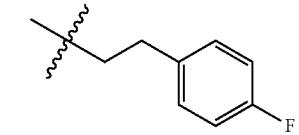 [SMILES: *CCc1ccc(F)cc1] |
| 65 | 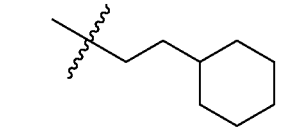 [SMILES: *CCC1CCCCC1] |
| 66 | |
| 67 | |
| 68 | |
| 69 | |
| 70 | n-hexyl |
| 71 | $CH_2COOH$ |
| 72 | Ethyl |

TABLE 3-continued

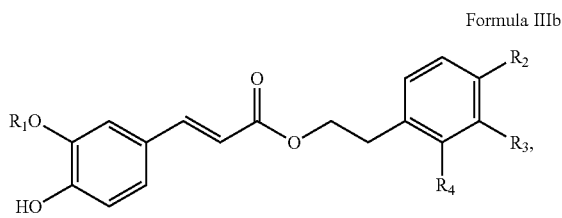

| Compound | R |
|---|---|
| 73 | n-propyl |
| 74 | isopropyl |
| 75 | isobutyl | or a pharmaceutically acceptable salt thereof.

In one aspect, the invention includes a compound of formula IIIb:

Formula IIIb or a pharmaceutically acceptable salt thereof, wherein $R_1$, $R_2$, $R_3$, and $R_4$ are selected from the group consisting of H, —OH, halo, $C_{1-6}$ alkyl, $C_{1-6}$ haloalkyl, and $C_{1-6}$ alkoxy.

In one embodiment, $R_1$, $R_2$, $R_3$, and $R_4$ are selected from the group consisting of H, —OH, methyl, and methoxy.

In still another embodiment, the compound of formula IIIb is selected from the list of compounds in Table 4.

TABLE 4

| Compound | $R_1$ | $R_2$ | $R_3$ | $R_4$ |
|---|---|---|---|---|
| 76 | H | OH | H | H |
| 77 | CH₃ | OH | H | H |
| 78 | H | H | OH | H |
| 79 | CH₃ | H | OH | H |
| 80 | H | H | H | OH |
| 81 | CH₃ | H | H | OH |
| 82 | H | OH | OH | H |
| 83 | CH₃ | OH | OH | H |
| 84 | CH₃ | OCH₃ | H | H |
| 85 | H | H | OCH₃ | H |
| 86 | H | OCH₃ | OCH₃ | H |
| 87 | CH₃ | OCH₃ | OCH₃ | H | or a pharmaceutically acceptable salt thereof.

In one aspect, the invention includes a compound of formula IIIc

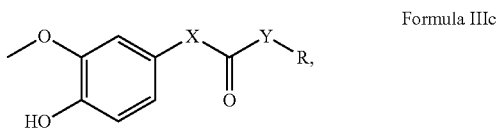

Formula IIIc or a pharmaceutically acceptable salt thereof,
wherein, X is a bond, or a bivalent $C_{1-6}$ alkyl group or $C_{1-6}$ alkenyl group;
Y is —O— or —NH—; and
R is A-B, wherein A is a bivalent $C_{1-6}$ alkyl or $C_{1-6}$ alkenyl group, and B is H or a 5-6 membered aryl group, or 5-6 membered cycloalkyl group, optionally substituted with one or more substituents selected from the group consisting of halo, nitro, cyano, —CF₃, $C_{1-6}$ alkyl, $C_{1-6}$ alkoxy, and hydroxyl.

In one embodiment, X is a bond, methylene, ethylene, propylene, or —CH═CH—. In a further embodiment, X is a bond, methylene or —CH═CH—.

In one embodiment, A is selected from the group consisting of methylene, ethylene, propylene, isopropylene, 2-methylbut-2-enylene, and butylene. In a further embodiment, A is ethylene.

In another embodiment, B is phenyl, optionally substituted with halo, nitro, cyano, —CF₃, $C_{1-6}$ alkyl, $C_{1-6}$ alkoxy, or hydroxyl. In a further embodiment, B is phenyl optionally substituted with fluoro, methyl, —CF₃, or methoxy.

In another embodiment, B is cyclohexyl. In a further embodiment, B is unsubstituted cyclohexyl.

In some embodiments, the compound of formula IIIc is selected from the compounds listed in Table 5.

TABLE 5

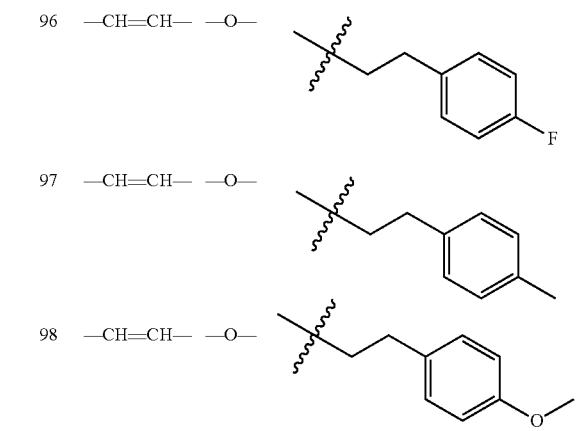

| Compound | X | Y | R |
|---|---|---|---|
| 88 | —CH═CH— | —O— | Methyl |
| 89 | —CH═CH— | —O— | Ethyl |
| 90 | —CH═CH— | —O— | n-propyl |
| 91 | —CH═CH— | —O— | Isopropyl |
| 92 | —CH═CH— | —O— | n-butyl |
| 93 | —CH═CH— | —O— | 2-methylbut-2-enyl |
| 94 | —CH═CH— | —O— | —CH₂Ph |
| 95 | —CH═CH— | —O— | —CH₂CH₂Ph |
| 96 | —CH═CH— | —O— | (4-fluorophenethyl) |
| 97 | —CH═CH— | —O— | (4-methylphenethyl) |
| 98 | —CH═CH— | —O— | (4-methoxyphenethyl) |

TABLE 5-continued

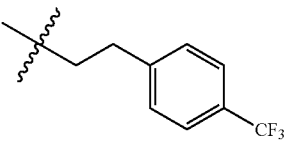

| Compound | X | Y | R |
|---|---|---|---|
| 99 | —CH=CH— | —O— | 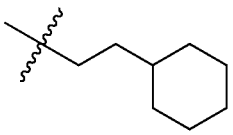 [SMILES: *CCC1CCCCC1] |
| 100 | —CH=CH— | —NH— | —CH$_2$CH$_2$Ph |
| 101 | —CH=CH— | —O— | 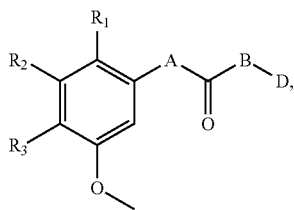 |
| 102 | —CH$_2$— | —O— | —CH$_2$CH$_2$Ph |
| 103 | —CH$_2$CH$_2$— | —O— | —CH$_2$CH$_2$Ph |
| 104 | —CH$_2$CH$_2$— | —O— | —CH$_2$CH$_2$CH$_2$Ph |
| 105 | bond | —O— | —CH$_2$CH$_2$Ph | or a pharmaceutically acceptable salt thereof.

In one aspect, the invention includes a compound of formula IIId

Formula IIId or a pharmaceutically acceptable salt thereof, wherein, R$_1$, R$_2$, and R$_3$ are each independently selected from the group consisting of H, —OH, C$_{1-6}$ alkoxy, and —OC(O)(C$_{1-6}$ alkyl);

A is a bond or a bivalent C$_{1-6}$ alkyl group or a C$_{1-6}$ alkenyl group;

B is —O— or —NH—; and

D is X—Y, wherein X is a bivalent C$_{1-6}$ alkyl group, C$_{1-6}$ alkenyl group, C$_{1-6}$ alkynyl group, and Y is H, —COOH, or a 5-6 membered aryl group, or 5-6 membered cycloalkyl group, optionally substituted with one or more substituents selected from the group consisting of halo, nitro, cyano, —CF$_3$, C$_{1-6}$ alkyl, C$_{1-6}$ alkoxy, and hydroxyl.

In a further embodiment, R$_1$, R$_2$, and R$_3$ are each independently selected from the group consisting of H, —OH, —OCH$_3$, and —OC(O)CH$_3$;

In one embodiment, A is a bond, methylene, ethylene, propylene, or —CH=CH—. In a further embodiment, A is a bond, methylene, ethylene, or —CH=CH—. In still a further embodiment, A is —CH=CH—.

In one embodiment, X is selected from the group consisting of methylene, ethylene, propylene, isopropylene, 2-methylbut-2-enylene, —CH$_2$CC—, and butylene. In a further embodiment, X is ethylene.

In another embodiment, Y is phenyl, optionally substituted with halo, nitro, cyano, —CF$_3$, C$_{1-6}$ alkyl, C$_{1-6}$ alkoxy, or hydroxyl. In a further embodiment, Y is phenyl optionally substituted with methyl, fluoro, —CF$_3$, or methoxy.

In another embodiment, Y is cyclohexyl. In a further embodiment, Y is unsubstituted cyclohexyl.

In another embodiment, Y is H.

In some embodiments, the compound of formula Hid is selected from the compounds listed in Table 6.

TABLE 6

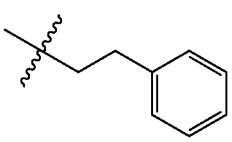 [SMILES: *CCc1ccccc1]

| Compound | R$_1$ | R$_2$ | R$_3$ | A | B | D |
|---|---|---|---|---|---|---|
| 106 | H | —OCH$_3$ | —OC(O)CH$_3$ | —CH=CH— | —O— | |

TABLE 6-continued

| Compound | R₁ | R₂ | R₃ | A | B | D |
|---|---|---|---|---|---|---|
| 107 | H | —OCH₃ | —OH | —CH=CH— | —O— | 4-F-phenylpropyl |
| 108 | H | —OCH₃ | —OH | —CH=CH— | —O— | 3-F-phenylpropyl |
| 109 | H | —OCH₃ | —OH | —CH=CH— | —O— | 2-F-phenylpropyl |
| 110 | H | —OCH₃ | —OH | —CH=CH— | —O— | 4-CF₃-phenylpropyl |
| 111 | H | —OCH₃ | —OH | —CH=CH— | —O— | 3-CF₃-phenylpropyl |
| 112 | H | —OCH₃ | —OH | —CH=CH— | —O— | 2-CF₃-phenylpropyl |
| 113 | H | —OCH₃ | —OH | —CH=CH— | —O— | 4-CH₃-phenylpropyl |
| 114 | H | —OCH₃ | —OH | —CH=CH— | —O— | 3-CH₃-phenylpropyl |

TABLE 6-continued

| Compound | R₁ | R₂ | R₃ | A | B | D |
|---|---|---|---|---|---|---|
| 115 | H | —OCH₃ | —OH | —CH=CH— | —O— | (2-methylphenyl)ethyl |
| 116 | H | —OCH₃ | —OH | —CH=CH— | —O— | (4-methoxyphenyl)ethyl |
| 117 | H | —OCH₃ | —OH | —CH=CH— | —O— | (3-methoxyphenyl)ethyl |
| 118 | H | —OCH₃ | —OH | —CH=CH— | —O— | (2-methoxyphenyl)ethyl |
| 119 | H | —OCH₃ | —OH | —CH=CH— | —NH— | phenethyl |
| 120 | H | —OCH₃ | —OH | —CH₂— | —O— | phenethyl |
| 121 | H | —OCH₃ | —OH | —CH=CH— | —O— | Ethyl |
| 122 | H | —OCH₃ | —OH | —CH=CH— | —O— | n-propyl |
| 123 | H | —OCH₃ | —OH | —CH=CH— | —O— | CH₂CCH |
| 124 | H | —OCH₃ | —OH | —CH=CH— | —O— | Isopropyl |
| 125 | —OCH₃ | H | H | —CH=CH— | —O— | CH₂CH=C(CH₃)₂ |
| 126 | —OCH₃ | H | H | —CH=CH— | —O— | cyclohexylethyl |
| 127 | H | —OCH₃ | —OH | —CH₂CH₂— | —O— | phenethyl |

TABLE 6-continued
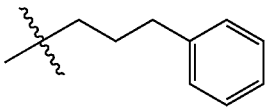 [SMILES: *CCCc1ccccc1]
| Compound | R₁ | R₂ | R₃ | A | B | D |
|---|---|---|---|---|---|---|
| 128 | H | —OCH₃ | —OH | —CH₂CH₂— | —O— | 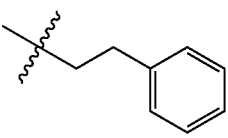 [SMILES: *CCc1ccccc1] |
| 129 | H | —OCH₃ | —OH | Bond | —O— | 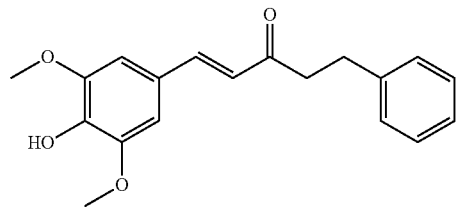 |
or a pharmaceutically acceptable salt thereof.
In some embodiments, the invention includes the compounds listed in Table 7.
TABLE 7
| Compound | Structure |
|---|---|
| 130 | 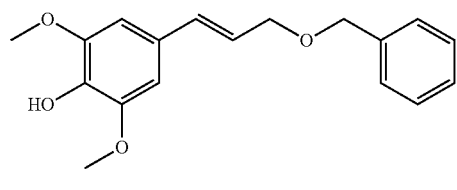 [SMILES: COc1cc(/C=C/COCc2ccccc2)cc(OC)c1O] |
| 131 | 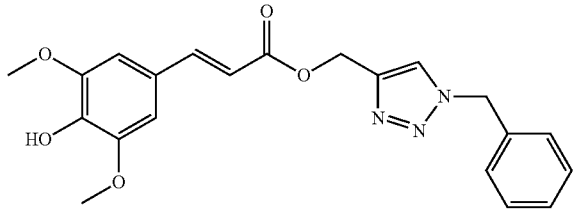 [SMILES: COc1cc(/C=C/C(=O)OCc2cn(Cc3ccccc3)nn2)cc(OC)c1O] |
| 132 | 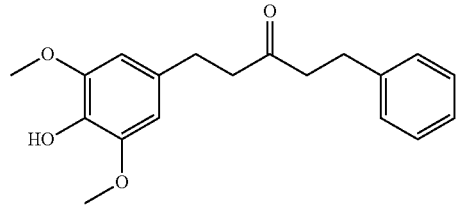 |
| 133 | 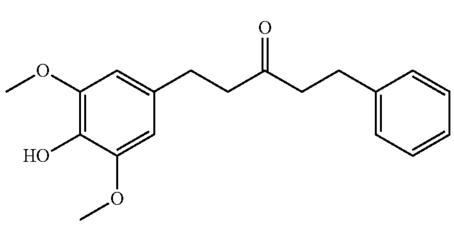 [SMILES: COc1cc(CCC(=O)CCc2ccccc2)cc(OC)c1O] |

TABLE 7-continued

| Compound | Structure |
|---|---|
| 134 | 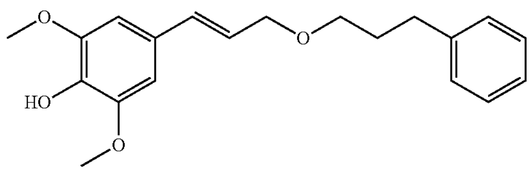 [SMILES: COc1cc(/C=C/COCCCc2ccccc2)cc(OC)c1O] |
| 135 | 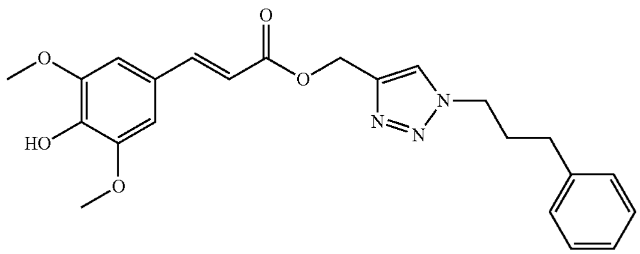 [SMILES: COc1cc(/C=C/C(=O)OCc2cn(CCCc3ccccc3)nn2)cc(OC)c1O] |
| 136 | 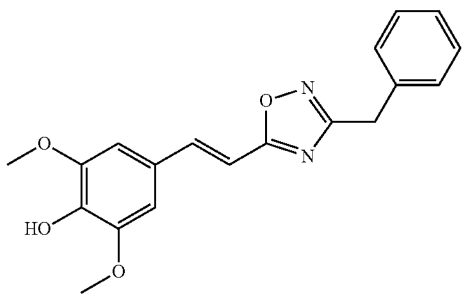 [SMILES: COc1cc(/C=C/c2nc(Cc3ccccc3)no2)cc(OC)c1O] |
| 137 | | or a pharmaceutically acceptable salt thereof.

In one aspect, the invention includes compounds of formula IIIe

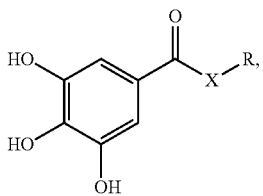

Formula IIIe or a pharmaceutically acceptable salt thereof, wherein X is —O— or —NH—; and R is selected from the group consisting of $C_{1-6}$ alkyl, $C_{1-6}$ alkenyl, and $C_{1-6}$ alkynyl, wherein R is substituted by a 5-6 membered aryl group, which is further optionally substituted with halo, cyano, hydroxyl, nitro, $C_{1-6}$ alkyl, or $C_{1-6}$ alkoxy.

In a further embodiment, R is $C_{1-6}$ alkyl substituted by a phenyl, wherein the phenyl is optionally substituted with halo, cyano, hydroxyl, nitro, $C_{1-6}$ alkyl, or $C_{1-6}$ alkoxy. In a further embodiment, R is $C_{1-6}$ alkyl substituted by an unsubstituted phenyl. In still a further embodiment, R is benzyl, —CH$_2$CH$_2$Ph, or —CH$_2$CH$_2$CH$_2$Ph.

In another embodiment, R is an unsubstituted $C_{1-6}$ alkyl, $C_{1-6}$ alkenyl, or $C_{1-6}$ alkynyl. In a further embodiment, R is selected from the group consisting of methy, ethyl, n-propyl, isopropyl, allyl, and —CH$_2$CCH.

In one embodiment, the compound of formula IIIe is selected from the group consisting of the compounds listed in Table 8.

TABLE 8

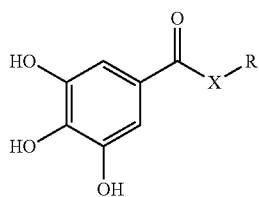

| Compound | X | R |
|---|---|---|
| 138 | —O— | Methyl |
| 139 | —O— | Ethyl |
| 140 | —O— | n-propyl |
| 141 | —O— | Isopropyl |
| 142 | —O— | Allyl |
| 143 | —O— | —CH$_2$CCH |
| 144 | —O— | Benzyl |
| 145 | —O— | —CH$_2$CH$_2$CH$_2$Ph |
| 146 | —NH— | —CH$_2$CH$_2$Ph | or a pharmaceutically acceptable salt thereof.

In one aspect, the invention includes a compound of formula IIIf

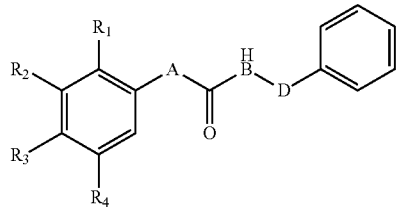

Formula IIIf or a pharmaceutically acceptable salt thereof, wherein, R$_1$, R$_2$, R$_3$, and R$_4$ are each independently selected from the group consisting of H or —OH;

A is a bond or a bivalent C$_{1-6}$ alkyl group or a C$_{1-6}$ alkenyl group;

B is a bond, —O—, or —NH—; and

D is a bivalent C$_{1-6}$ alkyl or C$_{1-6}$ alkenyl group.

In one embodiment, A is a bond, methylene, ethylene, propylene, or —CH=CH—. In a further embodiment, A is a bond or —CH=CH—. In still a further embodiment, A is —CH=CH—.

In one embodiment, B is a bond or —O—.

In one embodiment, D is selected from the group consisting of methylene, ethylene, propylene, isopropylene, and butylene. In a further embodiment, D is ethylene or propylene. In still a further embodiment, D is ethylene. In another further embodiment, D is propylene.

In some embodiments, the compound of formula IIIf is selected from the compounds listed in Table 9.

TABLE 9

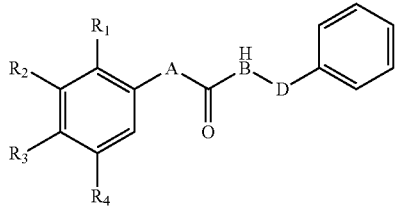

| Compound | R$_1$ | R$_2$ | R$_3$ | R$_4$ | A | B | D |
|---|---|---|---|---|---|---|---|
| 147 | —OH | —OH | H | H | —CH=CH— | —O— | —CH$_2$CH$_2$— |
| 148 | —OH | —OH | H | H | —CH=CH— | —O— | —CH$_2$CH$_2$CH$_2$— |
| 149 | H | —OH | H | —OH | —CH=CH— | —O— | —CH$_2$CH$_2$— |
| 150 | H | —OH | H | —OH | —CH=CH— | —O— | —CH$_2$CH$_2$CH$_2$— |
| 151 | —OH | H | H | —OH | —CH=CH— | —O— | —CH$_2$CH$_2$— |
| 152 | —OH | H | H | —OH | —CH=CH— | —O— | —CH$_2$CH$_2$CH$_2$— |
| 153 | —OH | H | H | —OH | —CH=CH— | Bond | —CH$_2$CH$_2$— |
| 154 | —OH | H | H | —OH | Bond | —O— | —CH$_2$CH$_2$— | or a pharmaceutically acceptable salt thereof.

Clauses of the Invention:

A compound of Formula Ia:

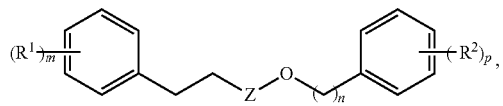

Formula Ia or a pharmaceutically acceptable salt thereof, wherein

Z is CH$_2$ or C=O;

R$^1$ and R$^2$ are each independently —OH, halo, —CN, —NO$_2$, —CF$_3$, —C(O)H, —C(O)R$^{1a}$, —C(O)OH, —C(O)OR$^{1a}$, —OR$^{1a}$, —NHR$^{1a}$, —N(R$^{1a}$)$_2$, —SO$_2$R$^{1a}$, —SO$_2$NHR$^{1a}$, —SO$_2$N(R$^{1a}$)$_2$, —NHSO$_2$R$^{1a}$, —NHSO$_2$NHR$^{1a}$, or —NHSO$_2$N(R$^{1a}$)$_2$; or two R$^1$ substituents or two R$^2$ substituents, together with the atoms to which they are attached, form a 4-10 membered aryl, heteroaryl, cycloalkyl, or heterocycloalkyl, optionally substituted with one or more R$^{1a}$;

each R$^{1a}$ is independently —C$_{1-6}$ alkyl, cycloalkyl, heterocycloalkyl, aryl, or heteroaryl, wherein each R$^{1a}$ is optionally and independently substituted with —OH, halo, —CN, —NO$_2$, —CF$_3$, —C(O)H, —C(O)(—C$_{1-6}$ alkyl), —C(O)OH, —C(O)O(—C$_{1-6}$ alkyl), —O(—C$_{1-6}$ alkyl), —NH(—C$_{1-6}$ alkyl), —N(—C$_{1-6}$ alkyl)$_2$, —SO$_2$(—C$_{1-6}$ alkyl), —SO$_2$NH(—C$_{1-6}$ alkyl), —SO$_2$N(—C$_{1-6}$ alkyl)$_2$, —NHSO$_2$(—C$_{1-6}$ alkyl), —NHSO$_2$NH(—C$_{1-6}$ alkyl), or —NHSO$_2$N(—C$_{1-6}$ alkyl)$_2$;

m and p are each independently an integer from 0-5; and n is an integer from 4-10.

The compound according to clause 1, wherein p is zero.

The compound according to clause 1 or clause 2, wherein each R$^1$ is independently halo, —OH, —CN, —NO$_2$, —CF$_3$, —O(—C$_{1-6}$ alkyl), —NH(—C$_{1-6}$ alkyl), or —N(—C$_{1-6}$ alkyl)$_2$.

The compound according to any one of clauses 1-3, wherein each $R^1$ is independently —OH, —OCH$_3$, —CN, or —CF$_3$.

The compound according to any one of clauses 1-4, wherein each $R^1$ is —OH.

The compound according to any one of clauses 1-5, wherein m is an integer from 1-3.

The compound according to any one of clauses 1-6, wherein m is 2.

The compound according to any one of clauses 1-7, wherein

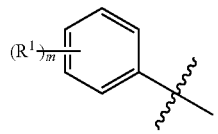

of Formula Ia is

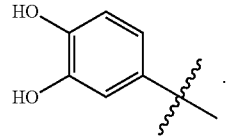

The compound according to any one of clauses 1-8, wherein Z is CH$_2$.

The compound according to any one of clauses 1-8, wherein Z is C=O.

The compound according to clause 1, wherein the compound is selected from:

A compound of Formula Ib:

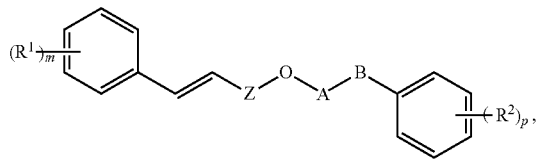

Formula Ib or a pharmaceutically acceptable salt thereof, wherein

Z is CH$_2$ or C=O;

$R^1$ and $R^2$ are each independently —OH, halo, —CN, —NO$_2$, —CF$_3$, —C(O)H, —C(O)R$^{1a}$, —C(O)OH, —C(O)OR$^{1a}$, —OR$^{1a}$, —NHR$^{1a}$, —N(R$^{1a}$)$_2$, —SO$_2$R$^{1a}$, —SO$_2$NHR$^{1a}$, —SO$_2$N(R$^{1a}$)$_2$, —NHSO$_2$R$^{1a}$, —NHSO$_2$NHR$^{1a}$, or —NHSO$_2$N(R$^{1a}$)$_2$; or two $R^1$ substituents or two $R^2$ substituents, together with the atoms to which they are attached, form a 4-10 membered aryl, heteroaryl, cycloalkyl, or heterocycloalkyl, optionally substituted with one or more $R^{1a}$;

each $R^{1a}$ is independently —C$_{1-6}$ alkyl, cycloalkyl, heterocycloalkyl, aryl, or heteroaryl, wherein each $R^{1a}$ is optionally and independently substituted with —OH, halo, —CN, —NO$_2$, —CF$_3$, —C$_{1-6}$ alkyl, —C(O)H, —C(O)(—C$_{1-6}$ alkyl), —C(O)OH, —C(O)O(—C$_{1-6}$ alkyl), —O(—C$_{1-6}$ alkyl), —NH(—C$_{1-6}$ alkyl), —N(—C$_{1-6}$ alkyl)$_2$, —SO$_2$(—C$_{1-6}$ alkyl), —SO$_2$NH(—C$_{1-6}$ alkyl), —SO$_2$N(—C$_{1-6}$ alkyl)$_2$, —NHSO$_2$(—C$_{1-6}$ alkyl), —NHSO$_2$NH(—C$_{1-6}$ alkyl), or —NHSO$_2$N(—C$_{1-6}$ alkyl)$_2$;

| Cmp # | Name | Structure |
|---|---|---|
| 1 | 4-phenylbutyl 3-(3,4-dihydroxyphenyl)propanoate | 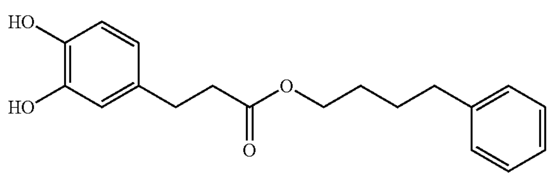 [SMILES: O=C(CCc1ccc(O)c(O)c1)OCCCCc1ccccc1] |
| 2 | 5-phenylpentyl 3-(3,4-dihydroxyphenyl)propanoate | 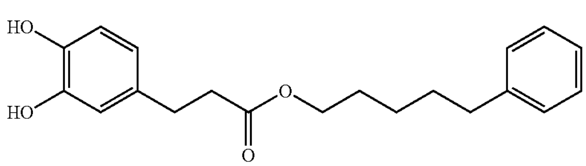 [SMILES: O=C(CCc1ccc(O)c(O)c1)OCCCCCc1ccccc1] |
| 3 | 6-phenylhexyl 3-(3,4-dihydroxyphenyl)propanoate |  | or a pharmaceutically acceptable salt thereof.

A is a $C_{1-6}$ alkylene, optionally substituted with one to three of —OH, halo, —CN, —NO$_2$, —CF$_3$, —$C_{1-6}$ alkyl, —C(O)H, —C(O)(—$C_{1-6}$ alkyl), —C(O)OH, —C(O)O(—$C_{1-6}$ alkyl), —O(—$C_{1-6}$ alkyl), —NH(—$C_{1-6}$ alkyl), —N(—$C_{1-6}$ alkyl)$_2$, —SO$_2$(—$C_{1-6}$ alkyl), —SO$_2$NH(—$C_{1-6}$ alkyl), —SO$_2$N(—$C_{1-6}$ alkyl)$_2$, —NHSO$_2$(—$C_{1-6}$ alkyl), —NHSO$_2$NHR$^{1a}$, or —NHSO$_2$N(R$^{1a}$)$_2$;

B is

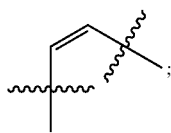 [SMILES: */C=C\*]

and m and p are each independently an integer from 0-5.

The compound according to clause 12, wherein p is zero.

The compound according to clause 12 or clause 13, wherein each R$^1$ is independently halo, —OH, —CN, —NO$_2$, —CF$_3$, —O(—$C_{1-6}$ alkyl), —NH(—$C_{1-6}$ alkyl), or —N(—$C_{1-6}$ alkyl)$_2$.

The compound according to any one of clauses 12-14, wherein each R$^1$ is independently —OH, —CN, or —CF$_3$.

The compound according to any one of clauses 12-15, wherein each R$^1$ is —OH.

The compound according to any one of clauses 12-16, wherein m is an integer from 1-3.

The compound according to any one of clauses 12-17, wherein m is 2.

The compound according to any one of clauses 12-18, wherein

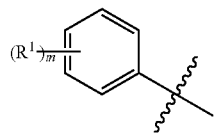

of Formula Ib is

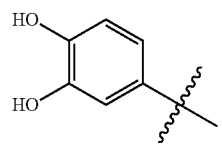

The compound according to any one of clauses 12-19, wherein Z is CH$_2$.

The compound according to any one of clauses 12-19, wherein Z is C═O.

The compound according to clause 12, wherein the compound is:

| Cmp # | Name | Structure |
|---|---|---|
| 4 | (E)-(Z)-3-phenylallyl 3-(3,4-dihydroxyphenyl)acrylate | 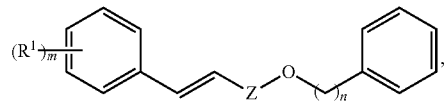 | or a pharmaceutically acceptable salt thereof.

A compound of Formula Ic:

Formula Ic $(R^1)_m$—⌬—Z—O—$(⌬)_n$ or a pharmaceutically acceptable salt thereof, wherein Z is CH$_2$ or C═O;

each R$^1$ is independently —OH, halo, —CN, —NO$_2$, —CF$_3$, —C(O)H, —C(O)R$^{1a}$, —C(O)OH, —C(O)OR$^{1a}$, —OR$^{1a}$, —NHR$^{1a}$, —N(R$^{1a}$)$_2$, —SO$_2$R$^{1a}$, —SO$_2$NHR$^{1a}$, —SO$_2$N(R$^{1a}$)$_2$, —NHSO$_2$R$^{1a}$, —NHSO$_2$NHR$^{1a}$, or —NHSO$_2$N(R$^{1a}$)$_2$; or two R$^1$ substituents, together with the atoms to which they are attached, form a 4-10 membered aryl, heteroaryl, or cycloalkyl, optionally substituted with one or more R$^{1a}$;

each R$^{1a}$ is independently —$C_{1-6}$ alkyl, cycloalkyl, heterocycloalkyl, aryl, or heteroaryl, wherein each R$^{1a}$ is optionally and independently substituted with —OH, halo, —CN, —NO$_2$, —CF$_3$, —$C_{1-6}$ alkyl, —C(O)H, —C(O)(—$C_{1-6}$ alkyl), —C(O)OH, —C(O)O(—$C_{1-6}$ alkyl), —O(—$C_{1-6}$ alkyl), —NH(—$C_{1-6}$ alkyl), —N(—$C_{1-6}$ alkyl)$_2$, —SO$_2$(—$C_{1-6}$ alkyl), —SO$_2$NH(—$C_{1-6}$ alkyl), —SO$_2$N(—$C_{1-6}$ alkyl)$_2$, —NHSO$_2$(—$C_{1-6}$ alkyl), —NHSO$_2$NH(—$C_{1-6}$ alkyl), —NHSO$_2$N(—$C_{1-6}$ alkyl)$_2$;

each m is independently an integer from 0-5; and n is 2 or 3;

provided that when n is 2,

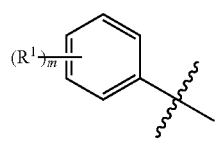

of Formula Ic is not phenyl,

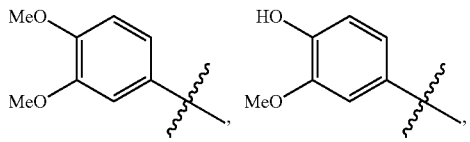

-continued

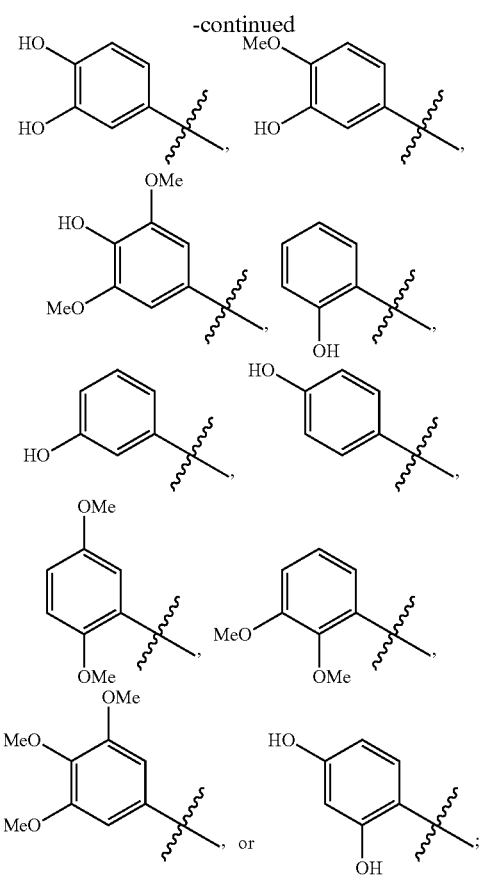

and
when n is 3,

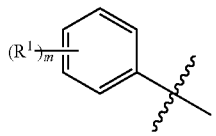

of Formula Ic is not

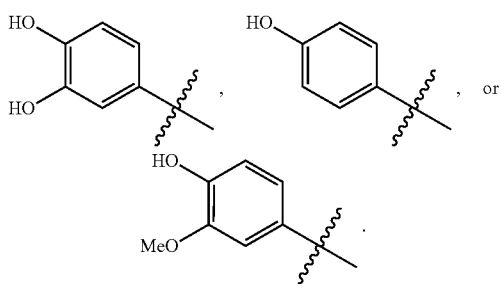

The compound according to clause 23, wherein each $R^1$ is independently halo, OH, —CN, —NO$_2$, —CF$_3$, —O(—C$_{1-6}$ alkyl), —NH(—C$_{1-6}$ alkyl), or —N(—C$_{1-6}$ alkyl)$_2$.

The compound according to clause 23 or clause 24, wherein each $R^1$ is independently halo, —OH, —OCH$_3$, —CN, or —CF$_3$.

The compound according to any one of clauses 23-25, wherein m is 3 and each $R^1$ is independently —OH or OCH$_3$.

The compound according to any one of clauses 23-25, wherein m is 2 and each $R^1$ is independently —OH, OCH$_3$, Cl, or CF$_3$.

The compound according to any one of clauses 23-25, wherein m is 1 and $R^1$ is —OH.

The compound according to any one of clauses 23-28, wherein

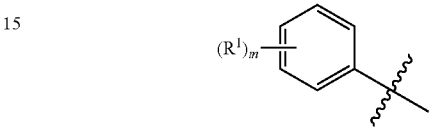

of Formula Ic

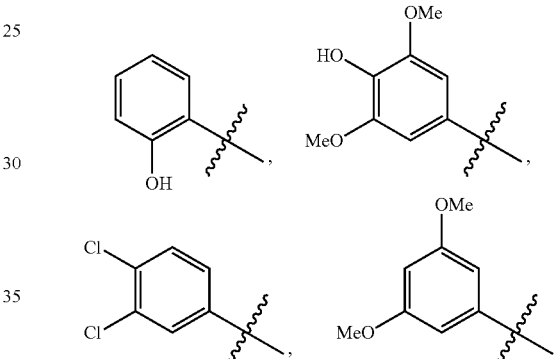

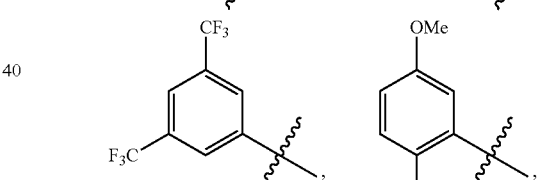

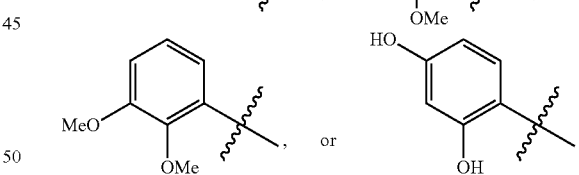

The compound according to clause 23, wherein two $R^1$ substituents, together with the atoms to which they are attached, form a 4-10 membered aryl, optionally substituted with one or more $R^{1a}$.

The compound according to clause 30, wherein

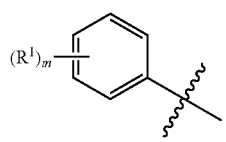

of Formula Ic is

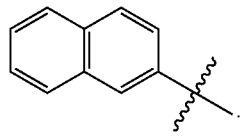

The compound according to any one of clauses 23-31, wherein Z is $CH_2$.

The compound according to any one of clauses 23-31, wherein Z is C=O.

The compound according to clause 23, wherein the compound is selected from:

| Cmp # | Name | Structure |
|---|---|---|
| 5 | (E)-3-phenylpropyl 3-(2-hydroxyphenyl) acrylate | 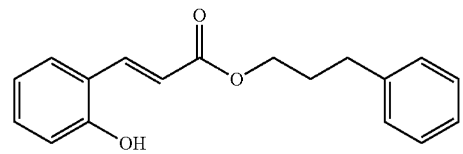 [SMILES: O=C(/C=C/c1ccccc1O)OCCCc1ccccc1] |
| 6 | (E)-3-phenylpropyl 3-(4-hydroxy-3,5-dimethoxyphenyl)acrylate | 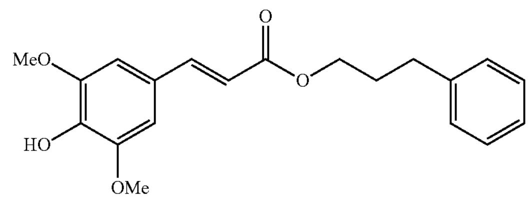 [SMILES: COc1cc(/C=C/C(=O)OCCCc2ccccc2)cc(OC)c1O] |
| 7 | (E)-phenethyl 3-(3,4-dichlorophenyl)acrylate | 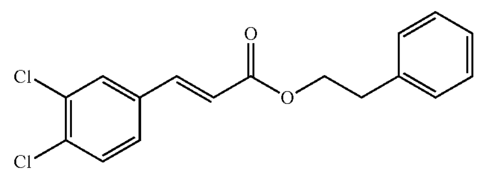 [SMILES: O=C(/C=C/c1ccc(Cl)c(Cl)c1)OCCc1ccccc1] |
| 8 | (E)-phenethyl 3-(naphthalen-2-yl)acrylate | 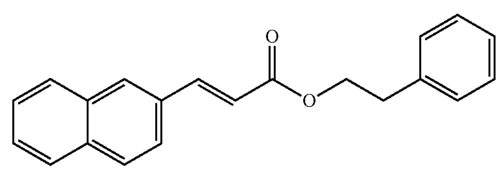 [SMILES: O=C(/C=C/c1ccc2ccccc2c1)OCCc1ccccc1] |
| 9 | (E)-phenethyl 3-(3,5-dimethoxyphenyl)acrylate | 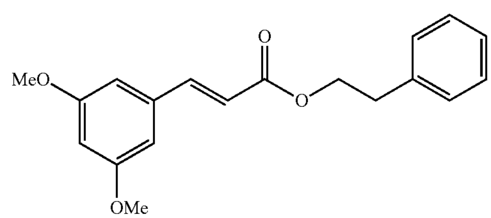 [SMILES: COc1cc(/C=C/C(=O)OCCc2ccccc2)cc(OC)c1] |
| 10 | (E)-3-phenylpropyl 3-(3,5-dimethoxyphenyl)acrylate | 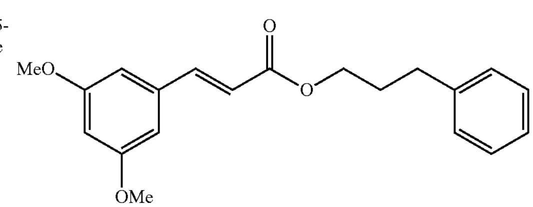 |
| 11 | (E)-3-phenylpropyl 3-(2,5-dimethoxyphenyl)acrylate | 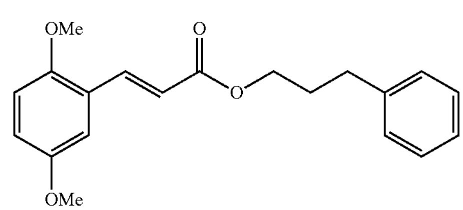 [SMILES: COc1ccc(OC)c(/C=C/C(=O)OCCCc2ccccc2)c1] |

-continued

| Cmp # | Name | Structure |
|---|---|---|
| 12 | (E)-3-phenylpropyl 3-(2,3-dimethoxyphenyl)acrylate | 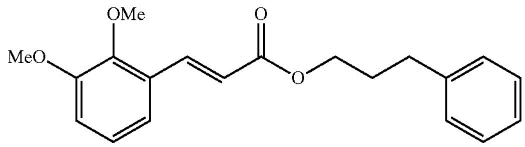 [SMILES: COc1cccc(/C=C/C(=O)OCCCc2ccccc2)c1OC] |
| 13 | (E)-phenethyl 3-(3,5-bis(trifluoromethyl)phenyl)acrylate | 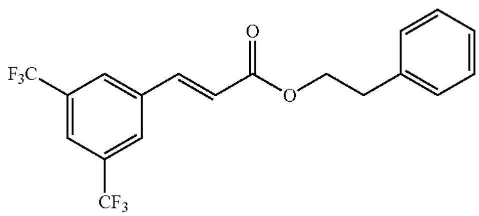 [SMILES: O=C(/C=C/c1cc(C(F)(F)F)cc(C(F)(F)F)c1)OCCc1ccccc1] |
| 14 | (E)-3-phenylpropyl 3-(2,4-dihydroxyphenyl)acrylate | | or a pharmaceutically acceptable salt thereof.

The compound according to clause 34, wherein the compound is:

| Cmp # | Name | Structure |
|---|---|---|
| 6 | (E)-3-phenylpropyl 3-(4-hydroxy-3,5-dimethoxyphenyl)acrylate | | or a pharmaceutically acceptable salt thereof.

A compound of Formula Id,

Formula Id

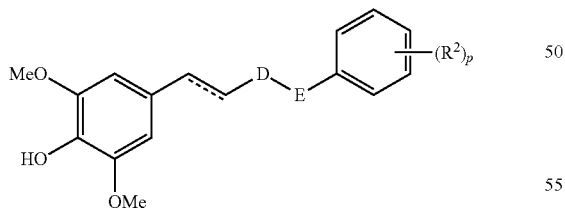

or a pharmaceutically acceptable salt thereof, wherein each $R^2$ is each independently —OH, halo, —CN, —NO$_2$, —CF$_3$, —C(O)H, —C(O)R$^{1a}$, —C(O)OH, —C(O)OR$^{1a}$, —OR$^{1a}$, —NHR$^{1a}$, —N(R$^{1a}$)$_2$, —SO$_2$R$^{1a}$, —SO$_2$NHR$^{1a}$, —SO$_2$N(R$^{1a}$)$_2$, —NHSO$_2$R$^{1a}$, —NHSO$_2$NHR$^{1a}$, or —NHSO$_2$N(R$^{1a}$)$_2$;

each $R^{1a}$ is independently —C$_{1-6}$ alkyl, cycloalkyl, heterocycloalkyl, aryl, or heteroaryl, wherein each $R^{1a}$ is optionally and independently substituted with —OH, halo, —CN, —NO$_2$, —CF$_3$, —C(O)H, —C(O)(—C$_{1-6}$ alkyl), —C(O)OH, —C(O)O(—C$_{1-6}$ alkyl), —O(—C$_{1-6}$ alkyl), —NH(—C$_{1-6}$ alkyl), —N(—C$_{1-6}$ alkyl)$_2$, —SO$_2$(—C$_{1-6}$ alkyl), —SO$_2$NH(—C$_{1-6}$ alkyl), —SO$_2$N(—C$_{1-6}$ alkyl)$_2$, —NHSO$_2$(—C$_{1-6}$ alkyl), —NHSO$_2$NH(—C$_{1-6}$ alkyl), or —NHSO$_2$N(—C$_{1-6}$ alkyl)$_2$;

the dotted line,

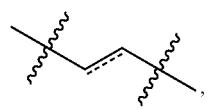

denotes a double bond or single bond;

D is a —C(R$^{1b}$)$_2$—, —C(R$^{1b}$)$_2$O—, —C(R$^{1b}$)$_2$N(R$^{1b}$)—, —C(O)—, —C(O)O—, —C(O)N(R$^{1b}$)—, —O—, or —N(R$^{1b}$)—;

E is a C$_{1-10}$ alkylene chain that is optionally substituted with one or more $R^{1b}$ substituents;

each $R^{1b}$ is independently hydrogen, halo, or $R^{1a}$; and p is an integer from 0-5;

provided that the compound is not

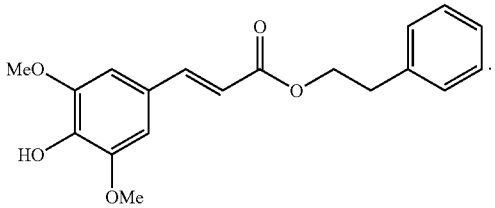 [SMILES: COc1cc(/C=C/C(=O)OCCc2ccccc2)cc(OC)c1O]

The compound according to clause 36, wherein the dotted line,

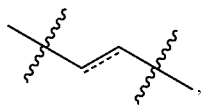

denotes a single bond.

The compound according to clause 36, wherein the dotted line,

denotes a double bond.

The compound according to any one of clauses 36-38, wherein E is a $C_{1-10}$ alkylene chain that is optionally substituted with halo, —$C_{1-6}$ alkyl, or phenyl.

The compound according to any one of clauses 36-39, wherein E is an unsubstituted $C_{1-10}$ alkylene chain.

The compound according to any one of clauses 36-40, wherein D is —$C(R^{1b})_2O$—, —C(O)—, —C(O)O—.

The compound according to clause 41, wherein D is —C(O)—.

The compound according to clause 41, wherein D is —C(O)O—.

The compound according to clause 41, wherein D is —$C(R^{1b})_2O$—, and each $R^{1b}$ is independently hydrogen, halo, —$C_{1-6}$ alkyl, or phenyl.

The compound according to clause 41, wherein D is —$C(R^{1b})_2O$—, and each $R^{1b}$ is hydrogen.

The compound according to clause 36, wherein each $R^2$ is independently —OH, halo, —CN, —$NO_2$, —$CF_3$, —C(O)OH, —C(O)O($C_{1-6}$ alkyl), —O($C_{1-6}$ alkyl), —NH($C_{1-6}$ alkyl), —N($C_{1-6}$ alkyl)$_2$, —$SO_2$($C_{1-6}$ alkyl), —$SO_2$NH($C_{1-6}$ alkyl), —$SO_2$N($C_{1-6}$ alkyl)$_2$, —$NHSO_2$($C_{1-6}$ alkyl), —$NHSO_2$NH($C_{1-6}$ alkyl), or —$NHSO_2$N($C_{1-6}$ alkyl)$_2$.

The compound according to clause 46, wherein each $R^2$ is independently —OH, halo, —$CF_3$, —C(O)OH, —C(O)O($C_{1-6}$ alkyl), or —O($C_{1-6}$ alkyl).

The compound according to clause 36, wherein p is 0.

A method of modulating lipoxygenase and/or cyclooxygenase activity, comprising contacting said lipoxygenase and/or cyclooxygenase with a compound of Formula IIa, Formula IIb, or Formula IIc Formula IIa

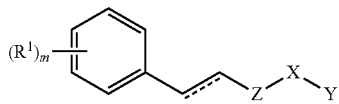

Formula IIb

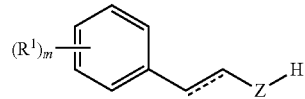

Formula IIc

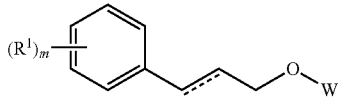

or a pharmaceutically acceptable salt thereof, wherein
each Z is independently $CH_2$ or C=O;
each W is independently hydrogen, a $C_{1-6}$ alkyl, cycloalkyl, heterocycloalkyl, aralkyl, aryl, heteroaralkyl, or heteroaryl, wherein W is optionally and independently substituted with up to three $R^1$ substituents;
each $R^1$ is independently —OH, halo, —CN, —$NO_2$, —$CF_3$, —C(O)H, —C(O)$R^{1a}$, —C(O)OH, —C(O)O$R^{1a}$, —O$R^{1a}$, —NH$R^{1a}$, —N($R^{1a}$)$_2$, —$SO_2R^{1a}$, —$SO_2$NH$R^{1a}$, —$SO_2$N($R^{1a}$)$_2$, —$NHSO_2R^{1a}$, —$NHSO_2$NH$R^{1a}$, or —$NHSO_2$N($R^{1a}$)$_2$; or
two $R^1$ substituents, together with the atoms to which they are attached, form a 4-10 membered aryl, heteroaryl, cycloalkyl, or heterocycloalkyl, optionally substituted with one or more $R^{1a}$;
each $R^{1a}$ is independently —$C_{1-6}$ alkyl, cycloalkyl, heterocycloalkyl, aryl, or heteroaryl, wherein each $R^{1a}$ is optionally and independently substituted with —OH, halo, —CN, —$NO_2$, —$CF_3$, —$C_{1-6}$ alkyl, —C(O)H, —C(O)(—$C_{1-6}$ alkyl), —C(O)OH, —C(O)O(—$C_{1-6}$ alkyl), —O(—$C_{1-6}$ alkyl), —NH(—$C_{1-6}$ alkyl), —N(—$C_{1-6}$ alkyl)$_2$, —$SO_2$(—$C_{1-6}$ alkyl), —$SO_2$NH(—$C_{1-6}$ alkyl), —$SO_2$N(—$C_{1-6}$ alkyl)$_2$, —$NHSO_2$(—$C_{1-6}$ alkyl), —$NHSO_2$NH(—$C_{1-6}$ alkyl), or —$NHSO_2$N(—$C_{1-6}$ alkyl)$_2$;
the dotted line,

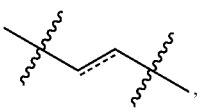

in Formula IIa denotes a double bond or single bond;
X is a bond, —O—, or —NH—;
Y is a moiety selected from the group consisting of:

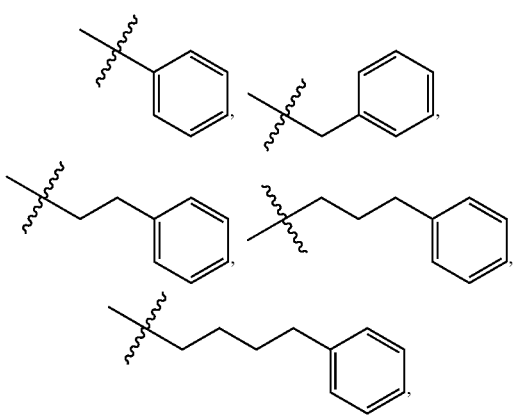

-continued
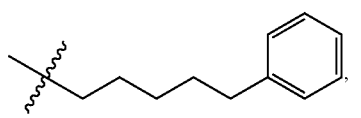
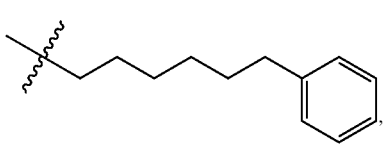
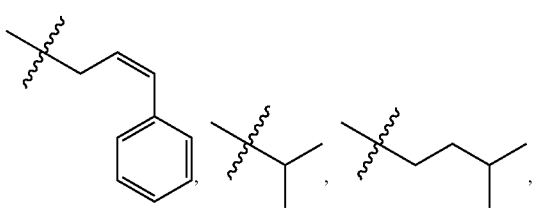
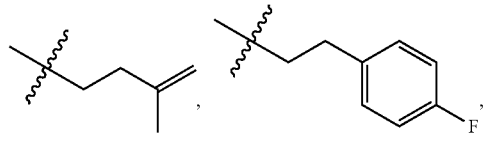
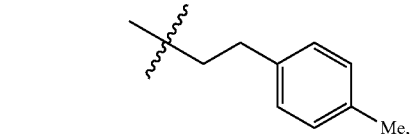
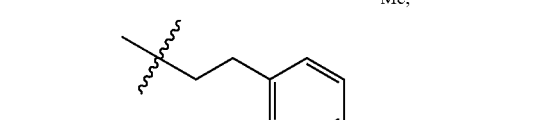
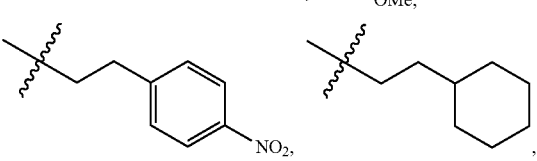
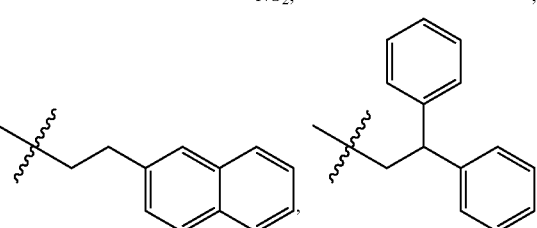
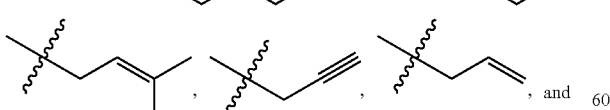
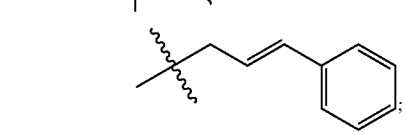
and
each m is independently an integer from 0-5;
provided that:
when X—Y is
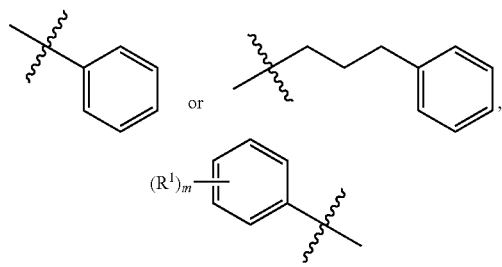
of Formula IIa is not
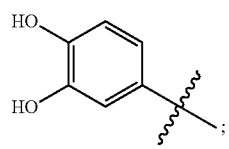 [SMILES: *c1ccc(O)c(O)c1]
when X—Y is
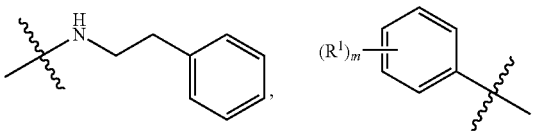
of Formula IIa is not phenyl or
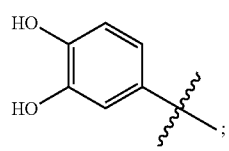 [SMILES: *c1ccc(O)c(O)c1]
when X—Y is
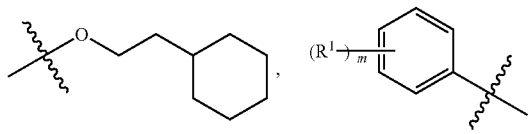
of Formula IIa is not
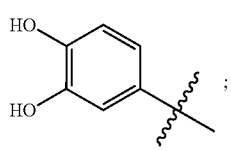 [SMILES: *c1ccc(O)c(O)c1]

when X—Y is

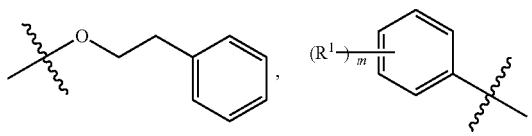

of Formula IIa is not phenyl,

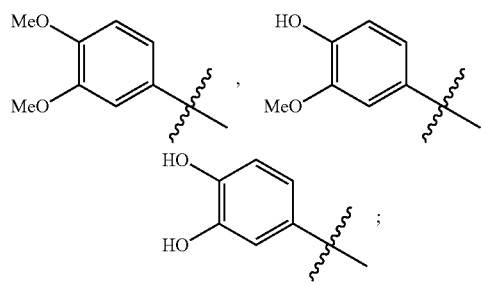

and
when m is 0, W of Formula IIc is not benzyl or

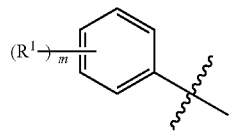

The method of clause 49, wherein the compound is a compound of Formula IIa.

The method according to clause 50, wherein each $R^1$ is independently halo, —OH, —CN, —NO$_2$, —CF$_3$, —O(—C$_{1-6}$ alkyl), —NH(—C$_{1-6}$ alkyl), or —N(—C$_{1-6}$ alkyl)$_2$.

The method according to clause 50 or clause 51, wherein each $R^1$ is independently halo, —OH, —OCH$_3$, —CN, or —CF$_3$.

The method according to any one of clauses 50-52, wherein m is 3 and each $R^1$ is independently —OH or OCH$_3$.

The method according to any one of clauses 50-53, wherein m is 2 and each $R^1$ is independently —OH, OCH$_3$, Cl, or CF$_3$.

The method according to any one of clauses 50-54, wherein m is 1 and $R^1$ is —OH.

The method according to any one of clauses 50-55, wherein

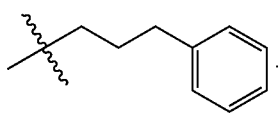 [SMILES: *CCCc1ccccc1]

of Formula IIa is

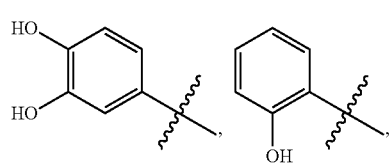

-continued

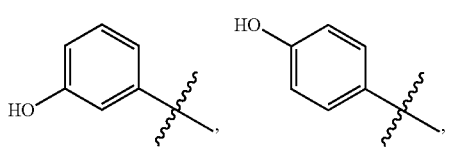

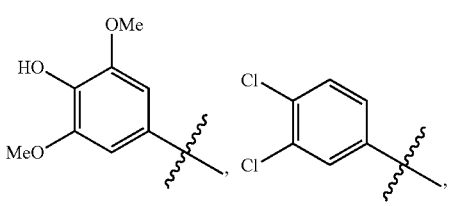

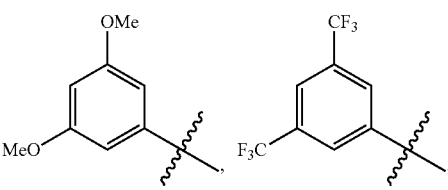

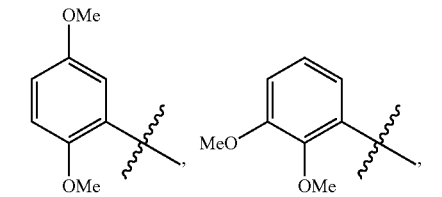

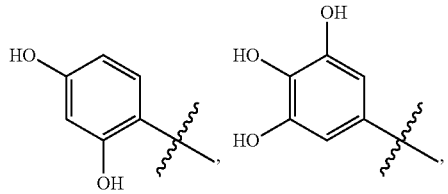

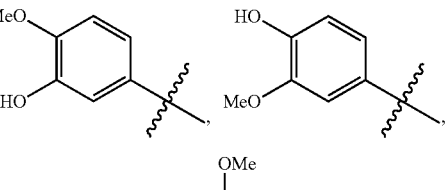

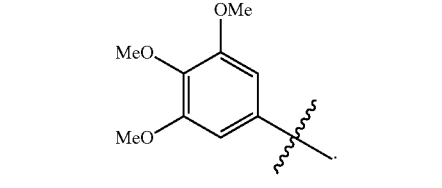

The method according to any one of clauses 50-56, wherein

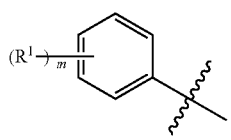

of Formula IIa is

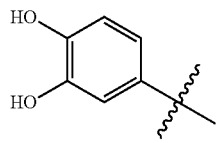

The method according to clause 50, wherein two $R^1$ substituents, together with the atoms to which they are attached, form a 4-10 membered aryl or heterocycloalkyl, optionally substituted with one or more $R^{1a}$.

The method according to clause 58, wherein

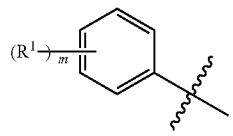

of Formula IIa is

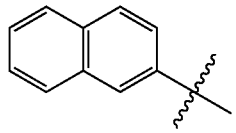 or 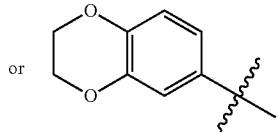.

The method according to any one of clauses 50-59, wherein the dotted line,

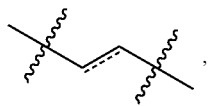

in Formula IIa denotes a double bond.

The method according to any one of clauses 50-60, wherein the dotted line,

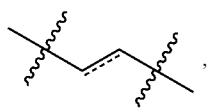

in Formula IIa denotes a single bond.

The method according to any one of clauses 50-61, wherein X is a bond.

The method according to any one of clauses 50-61, wherein X is —O—.

The method according to any one of clauses 50-61, wherein X is —NH—.

The compound according to any one of clauses 50-64, wherein Z is $CH_2$.

The compound according to any one of clauses 50-64, wherein Z is C=O.

The method of clause 49, wherein the compound is a compound of Formula IIb.

The method of clause 67, wherein each $R^1$ is independently halo, —OH, —$OCH_3$, —CN, or —$CF_3$.

The method according to clause 67 or clause 68, wherein m is 2 and each $R^1$ is independently —OH or $OCH_3$.

The method according to any one of clauses 67-69, wherein

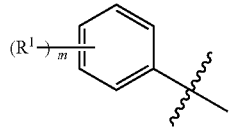

of Formula IIb is

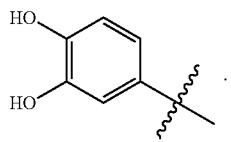

The method according to any one of clauses 67-70, wherein the dotted line,

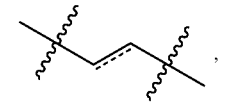

in Formula IIb denotes a double bond.

The method according to any one of clauses 67-71, wherein the dotted line,

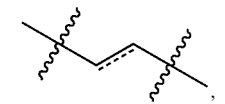

in Formula IIb denotes a single bond.

The compound according to any one of clauses 67-72, wherein Z is $CH_2$.

The compound according to any one of clauses 67-72, wherein Z is C=O.

The method of clause 49, wherein the compound is a compound of Formula IIc.

The method of clause 75, wherein each $R^1$ is independently halo, —OH, —$OCH_3$, —CN, or —$CF_3$.

The method according to clause 75 or clause 76, wherein m is 2 and each $R^1$ is independently —OH or $OCH_3$.

The method according to any one of clauses 75-77, wherein

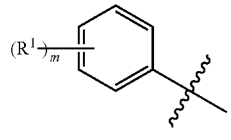

of Formula IIc is

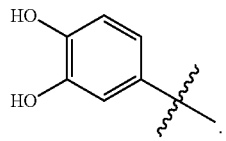

The method according to any one of clauses 75-78, wherein the dotted line,

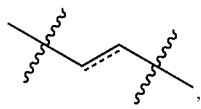

in Formula IIc denotes a double bond.

The method according to any one of clauses 75-78, wherein the dotted line,

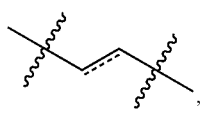

in Formula IIc denotes a single bond.

The method according to any one of clauses 75-80, wherein W is hydrogen, a $C_{1-6}$ alkyl, aralkyl, or aryl, and wherein W is optionally and independently substituted with up to three $R^1$ substituents.

The method according to any one of clauses 75-81, wherein W is aralkyl, and wherein W is optionally and independently substituted with up to three $R^1$ substituents.

The method according to any one of clauses 75-82, wherein W is

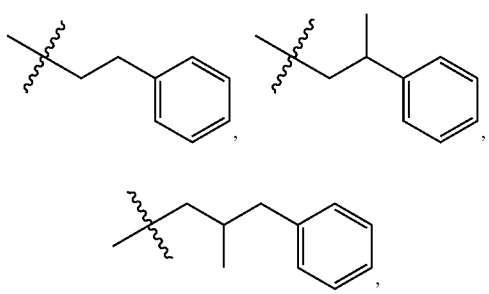

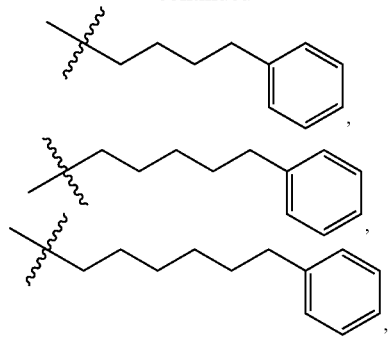

and wherein the phenyl group of W is optionally and independently substituted with up to three $R^1$ substituents.

The method according to clause 83, wherein W is unsubstituted.

The method according to any one of clauses 75-81, wherein W is a $C_{1-6}$ alkyl, optionally and independently substituted with up to three $R^1$ substituents.

The method according to any one of clauses 75-81, wherein W is an unsubstituted $C_{1-6}$ alkyl.

The method according to any one of clauses 75-81, wherein W is hydrogen.

The method according to clause 49, wherein the compound is selected from the compounds listed in Tables 1-9, or a pharmaceutically acceptable salt thereof.

The method of clause 88, wherein the compound is

| Cmp # | Name | Structure |
|---|---|---|
| 45 | (E)-phenethyl 3-(4-hydroxy-3,5-dimethoxyphenyl) acrylate | ![structure] | or a pharmaceutically acceptable salt thereof.

A pharmaceutical composition comprising a compound according to any one of clauses 1-48, and a pharmaceutically acceptable excipient.

A method of modulating lipoxygenase and/or cyclooxygenase activity, comprising contacting said lipoxygenase and/or cyclooxygenase with a compound according to any one of clauses 1-48, or a pharmaceutical composition according to clause 90.

The method according to any one of clauses 49-89 and 91, wherein the lipoxygenase is 5-lipoxygenase (5-LO).

The method according to any one of clauses 49-89 and 91, wherein the cyclooxygenase is cyclooxygenase-1, cyclooxygenase-2, or a combination thereof.

The method according to any one of clauses 49-89 and 91, wherein the activity of the lipoxygenase and/or cyclooxygenase is inhibited in the presence of the compound.

A method of treating or lessening the severity of a lipoxygenase and/or a cyclooxygenase mediated disease or condition, comprising administering to the subject in need thereof a compound according to any one of clauses 1-89.

The method according to clause 94, wherein the lipoxygenase is 5-lipoxygenase (5-LO).

The method according to clause 94, wherein the cyclooxygenase is cyclooxygenase-1, cyclooxygenase-2, or a combination thereof.

The method according to clause 95, wherein the disease or condition is selected from the group consisting of inflammation, chronic inflammation, inflammation-associated disorder, metabolic syndrome, pain, headache, fever, arthritis, rheumatoid arthritis, spondyloarthopathies, gouty arthritis, osteoarthritis, systemic lupus erythematosus, juvenile arthritis, asthma, bronchitis, menstrual cramps, tendinitis, bursitis, psoriasis, eczema, burns, dermatitis, inflammatory bowel disease, Crohn's disease, gastritis, irritable bowel syndrome, ulcerative colitis, colorectal cancer, prostate cancer, lung cancer, breast cancer, vascular disease, migraine headache, periarteritisnodosa, thyroiditis, aplastic anemia, Hodgkin's disease, sclerodoma, rheumatic fever, type I diabetes, myasthenia gravis, sarcoidosis, nephrotic syndrome, Behcet's syndrome, polymyositis, gingivitis, hypersensitivity, conjunctivitis, swelling occurring after injury, myocardial ischemia, allergic rhinitis, respiratory distress syndrome, endotoxic shock syndrome, atherosclerosis, and stroke.

III. Formulations, Administrations, and Uses

Pharmaceutically Acceptable Compositions

In one aspect of the present invention, pharmaceutically acceptable compositions are provided, wherein these compositions comprise any of the compounds or a pharmaceutically acceptable salt thereof, as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative or a prodrug thereof. According to the present invention, a pharmaceutically acceptable derivative or a prodrug includes, but is not limited to, pharmaceutically acceptable salts, esters, salts of such esters, or any other adduct or derivative which upon administration to a patient in need thereof is capable of providing, directly or indirectly, a compound as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof.

Pharmaceutically acceptable salts are well known in the art. For example, S. M. Berge, et al. describes pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange.

Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, edisylate (ethanedisulfonate), ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersible products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses of the Compounds and Pharmaceutically Acceptable Compositions Described Herein In yet another aspect, the present invention provides a method of treating or lessening the severity of a condition, disease, or disorder modulated by lipoxygenase and/or a cyclooxygenase, for example COX-1 and/or COX-2. In certain embodiments, the present invention provides a method of treating a condition, disease, or disorder modulated by 5-lipoxygenase, and/or a cyclooxygenase, for example COX-2, the method comprising administering to the patient an effective amount of a composition comprising a compound or composition described herein that effectively and therapeutically inhibits the activity of a lipoxygenase (e.g. 5-LO) and/or a cyclooxygenase, for example COX-1 and/or COX-2.

In certain embodiments, the present invention provides a method of treating a disease or condition mediated by lipoxygenase, and/or a cyclooxygenase, for example, COX-1 and/or COX-2. These diseases include, inflammation, chronic inflammation, inflammation-associated disorder, metabolic syndrome, pain, headache, fever, arthritis, rheumatoid arthritis, spondyloarthopathies, gouty arthritis, osteoarthritis, systemic lupus erythematosus, juvenile arthritis, asthma, bronchitis, menstrual cramps, tendinitis, bursitis, psoriasis, eczema, burns, dermatitis, inflammatory bowel disease, Crohn's disease, gastritis, irritable bowel syndrome, ulcerative colitis, colorectal cancer, prostate cancer, lung cancer, breast cancer, vascular disease, migraine headache, periarteritisnodosa, thyroiditis, aplastic anemia, Hodgkin's disease, scleredoma, rheumatic fever, type I diabetes, myasthenia gravis, sarcoidosis, nephrotic syndrome, Behcet's syndrome, polymyositis, gingivitis, hypersensitivity, conjunctivitis, swelling occurring after injury, myocardial ischemia, allergic rhinitis, respiratory distress syndrome, endotoxic shock syndrome, atherosclerosis, and stroke.

According to the invention an "effective amount" of the compound or pharmaceutically acceptable composition is that amount effective for treating or lessening the severity of one or more of the diseases, disorders or conditions as recited above.

The compounds and compositions, according to the method of the present invention, may be administered using any amount and any route of administration effective for treating or lessening the severity of one or more of the diseases, disorders or conditions as recited above.

The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, drops or patch), bucally, as an oral or nasal spray, or the like, depending on the severity of the infection being treated. In certain embodiments, the compounds of the invention, and pharmaceutically acceptable salts thereof, may be administered orally or parenterally at dosage levels of about 0.01 mg/kg to about 100 mg/kg and preferably from about 0.5 mg/kg to about 50 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms are prepared by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The activity of a compound utilized in this invention as a modulator of lipoxygenase and/or a cyclooxygenase, for example, COX-1 and/or COX-2, may be assayed according to methods described generally in the art and in the examples herein.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that is normally administered to treat or prevent a particular disease, or condition, are known as "appropriate for the disease, or condition, being treated."

In one embodiment, the additional agent is selected from an anti-inflammatory agent, an immunosuppressing agent and/or an anti-allergy agent. In some embodiments, exemplary additional agents can include, but not limited to: analgesics such as acetaminophen, naproxen sodium, ibuprofen, tramadol, aspirin, celecoxib, valdecoxib, indomethacin, and other NSAIDs; COX-2 inhibitors; anti-inflammatory drugs; sulfasalazine, mesalamine, balsalazide, and olsalazine; and corticosteroids such as prednisone and budesonide; immunosuppressant drugs such as, azathioprine, mercaptopurine, TNF blockers such as influximab and adalimumab, methotrexate, and cyclosporine; antibiotics such as metronidazole and ciprofloxacin; antidiarrheals such as loperamide; immunosuppressant drugs such as azathioprine, mercaptopurine, corticosteroids; immunosuppressants; Janus kinase-3 (Jak-3) inhibitors; and laxatives; antihistamines such as chlorpheniramine, desloratadine, levocetirizine, diphenhydramine, doxylamine succinate, triprolidine, clemastine, pheniramine, brompheniramine, dexbrompheniramine, loratadine, cetirizine and fexofenadine, amlexanox, alkylamine derivatives, cromolyn, acrivastine, ibudilast, bamipine, ketotifen, nedocromil, omalizumab, dimethindene, oxatomide, pemirolast, pyrrobutamine, pen-tigetide, thenaldine, picumast, tolpropamine, ramatroban, repirinast, suplatast tosylate aminoalkylethers, tazanolast, bromodiphenhydramine, tranilast, carbinoxamine, traxanox, chlorphenoxamine, diphenylpyaline, embramine, p-methyl-diphenhydramine, moxastine, orphenadrine, phenyltoloxamine, setastine, ethylenediamine derivatives, chloropyramine, chlorothen, methapyrilene, pyrilamine, talastine, thenyldiamine, thonzylamine hydrochloride, tripelennamine, piperazines, chlorcyclizine, clocinizine, homochlorcyclizine, hydroxyzine, tricyclics, phenothiazines, mequitazine, promethazine, thiazinamium methylsulfate, azatadine, cyproheptadine, deptropine, desloratadine, isothipendyl, olopatadine, rupatadine, antazoline, astemizole, azelastine, bepotastine, clemizole, ebastine, emedastine, epinastine, levocabastine, mebhydroline, mizolastine, phenindamine, terfenadine, and tritoqualine.

The compounds of this invention or pharmaceutically acceptable compositions thereof may also be incorporated into compositions for coating an implantable medical device, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccarides, polyethylene glycol, phospholipids or combinations thereof to impart controlled release characteristics in the composition.

Another aspect of the invention relates to modulating lipoxygenase and/or cyclooxygenase activity in a biological sample or a patient (e.g., in vitro or in vivo), which method comprises administering to the patient, or contacting said biological sample with a compound or composition described herein. The term "biological sample", as used herein, includes, without limitation, cell cultures or extracts thereof; biopsied material obtained from a mammal or extracts thereof; and blood, serum, plasma, saliva, urine, feces, semen, tears, or other body fluids or extracts thereof.

Modulation of lipoxygenase and/or cyclooxygenase in a biological sample is useful for a variety of purposes that are known to one of skill in the art. Examples of such purposes include, but are not limited to, the study of lipoxygenase and/or cyclooxygenase in biological and pathological phenomena; and the comparative evaluation of new modulators of lipoxygenase and/or cyclooxygenase, for example, modulators that inhibit the enzymatic activity of lipoxygenase and/or cyclooxygenase, for example, 5-LO and/or COX-1 and/or COX-2.

In order that the invention described herein may be more fully understood, the following examples are set forth. It should be understood that these examples are for illustrative purposes only and are not to be construed as limiting this invention in any manner.

III. Synthetic Schemes

All chemicals used were purchased from Aldrich or Alfaeaser. Purification of compounds was carried out by silica gel circular chromatography (Chromatotron®, model 7924, Harrison Research) or by flash chromatography (CombiFlash®, Separation System SG 100C, ISCO). TLC was run on silica gel coated aluminum sheets (SiliaPlate TLC, Silicycle) with detection by UV light (254 nm, UVS-11, Mineralight® shortwave UV lamp). Melting points were obtained using a MELTEMP® (model 1001D) melting point apparatus. FTIR spectra were recorded on a Nicolet® Impact 400 spectrometer. NMR spectra were recorded on a Bruker® Avance III 400 MHz spectrometer. High-resolution mass measurements were performed on a Bruker® Doltonics' micrOTOF instrument in positive or negative electrospray.

General Schemes for the Synthesis of Esters, Amides, Ethers, and Ketones

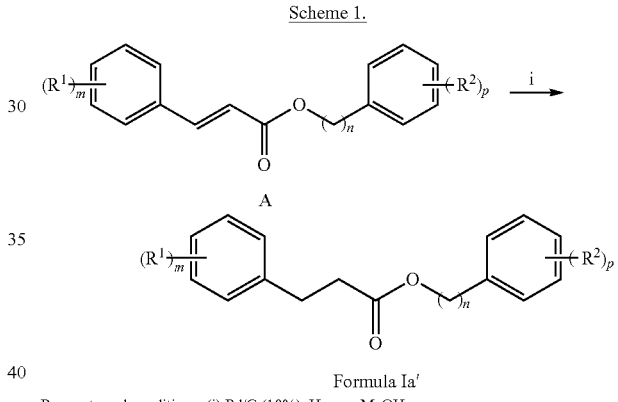

Reagents and conditions: (i) Pd/C (10%), H₂ gas, MeOH.

Compounds of Formula Ia' can be synthesized under hydrogenation conditions, such as hydrogen gas and 10% Pd/C in methanol. For example, the reaction can be performed with intermediate A in a sealed flask under a positive pressure of H₂ gas maintained by a balloon attached via a syringe needle. To work up, the reaction mixture can be filtered through celite and the solvent removed under reduced pressure to provide the product.

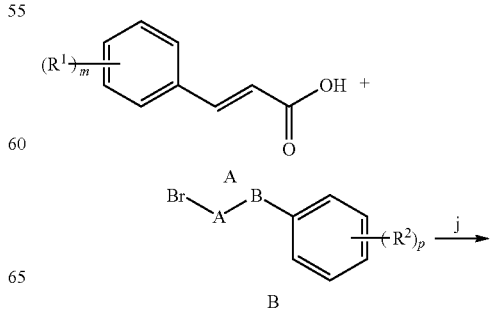

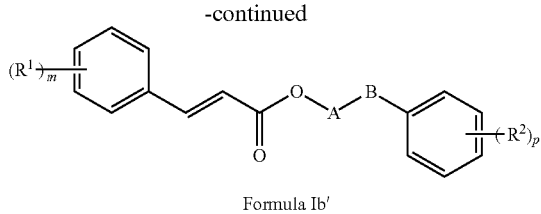

Formula Ib'

Reagents and conditions: (j), Na$_2$CO$_3$, KI, HMPA.

Compounds of Formula Ib', wherein R$^1$, R$^2$, m, p, A, and B are described herein, can be synthesized under esterification conditions, such as nucleophilic substitution of an alkyl bromide by the appropriate carboxylate. For example, alkyl bromide, B, can be contacted with carboxylic acid, C, in a polar solvent in the presence of a catalyst, such as KI, and a base. Nucleophilic substitution of the bromide by the carboxylate provides the compound of Formula Ib'. The product can be worked up by extraction from water by an organic solvent such as ethyl acetate.

Esters and Amides

Scheme 3.

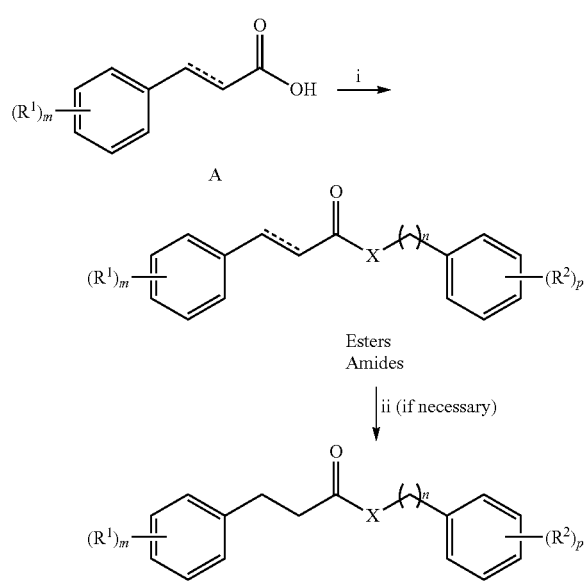

Reagents and conditions: i) when X is O: Base, (R$^2$)$_p$Ph(CH$_2$)nBr, KI, HMPA, or when X is NH: coupling agent (DCC, BOP, etc.), base (R$^2$)$_p$Ph(CH$_2$)nNH$_2$; ii) H$_2$, Pd/C.

Ester and amide compounds of the invention can be synthesized from the corresponding cinnamic or dihydrocinnamic acid derivatives of formula A according to Scheme 3 above, wherein R$^1$, R$^2$, X, m, n, and p are defined herein. Ester compounds can be synthesized via treatment of the acid with an alkyl bromide of the formula (R$^2$)$_p$Ph(CH$_2$)nBr, a base, an iodide source, such as potassium iodide, and a polar solvent, such as HMPA. Amide compounds can be synthesized via treatment of the acid with a coupling agent, such as DCC, EDC, BOP, or any other common coupling reagent know to those having skill in the art, in the presence of a solvent and, optionally, a base, and an amine of the formula (R$^2$)$_p$Ph(CH$_2$)nNH$_2$. Cinnamic acid derivatives can further be converted to the corresponding dihydrocinnamic acid derivative via hydrogenation with a palladium catalyst using common procedures known to those having skill in the art. It will also be understood that active R$^1$ and R$^2$ substituents, such as OH, NH$_2$, COOH, etc., can be protected using common methods known in the art.

Scheme 4.

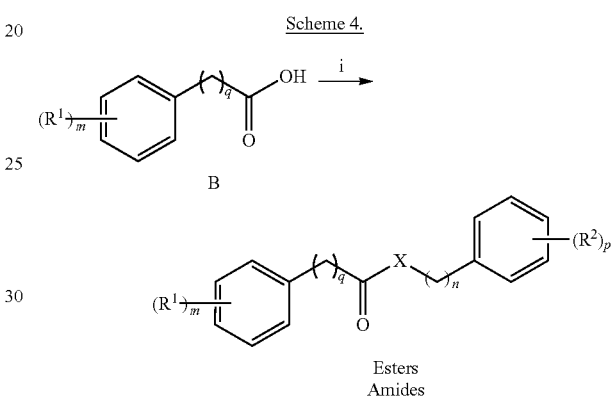

Esters
Amides

Reagents and conditions: i) when X is O: Base, (R$^2$)$_p$Ph(CH$_2$)nBr, KI, HMPA, or when X is NH: coupling agent (DCC, BOP, etc.), base (R$^2$)$_p$Ph(CH$_2$)nNH$_2$.

Ester and amide compounds of the invention can also be synthesized from the corresponding phenylalkyl carboxylic acid derivatives of formula B, wherein q is an integer from 1 to 10 and R$^1$, R$^2$, X, m and p are defined herein, according to Scheme 4 above. Ester compounds can be synthesized via treatment of the acid with an alkyl bromide of the formula (R$^2$)$_p$Ph(CH$_2$)nBr, a base, an iodide source, such as potassium iodide, and a polar solvent, such as HMPA. Amide compounds can be synthesized via treatment of the acid with a coupling agent, such as DCC, EDC, BOP, or any other common coupling reagent know to those having skill in the art, in the presence of a solvent and, optionally, a base, and an amine of the formula (R$^2$)$_p$Ph(CH$_2$)nNH$_2$. It will also be understood that active R$^1$ and R$^2$ substituents, such as OH, NH$_2$, COOH, etc., can be protected using common methods known in the art.

Ethers and Ketones

Scheme 5.

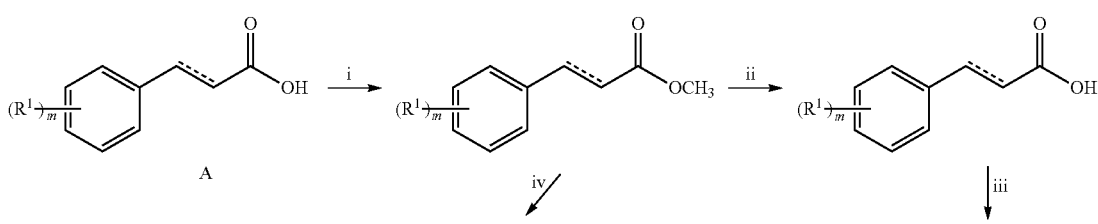

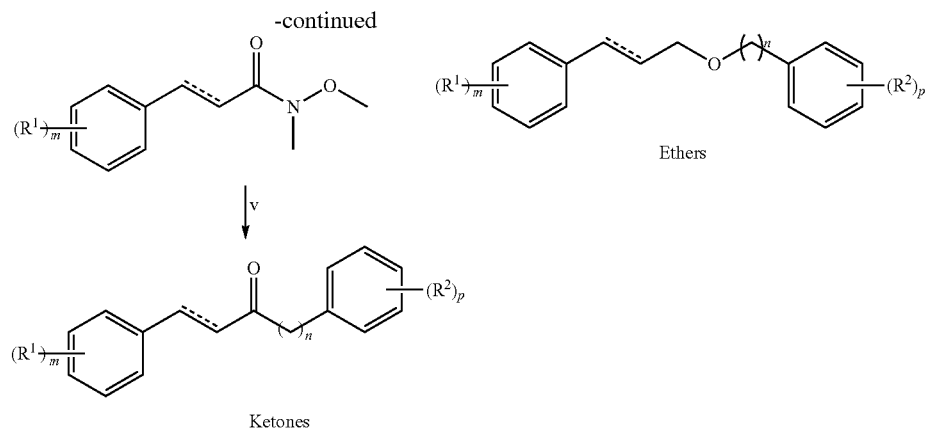

Ethers

Ketones

Reagents and conditions: i) MeOH, acid; ii) DIBAL; iii) base, $(R^2)_p Ph(CH_2)nBr$; iv) $CH_3NHOCH_3$—HCl, i-PrMgCl,; v) $(R^2)_p Ph(CH_2)nMgBr$.

Ketones and ethers of the invention can be synthesized according to the methods provided in Scheme 5, wherein $R^1$, $R^2$, m, n, and p are defined herein. Ketones of the invention can be synthesized by esterification of a carboxylic acid of formula A in acidic methanol followed by formation of the Weinreb Amide using —N,O-dimethylhydroxylamine hydrochloride and isopropyl magnesium chloride. The Weinreb Amide can then be converted to a ketone using a Grignard reagent of the formula $(R^2)_p Ph(CH_2)nMgBr$. Ethers of the invention can by synthesized by esterification of a carboxylic acid of formula A in acidic methanol, followed by reduction with DIBAL to provide the primary alcohol. The alcohol is then alkylated to provide an ether using a base and an alkyl bromide of the formula $(R^2)pPh(CH_2)nBr$. It will also be understood that active $R^1$ and $R^2$ substituents, such as OH, $NH_2$, COOH, etc., can be protected using common methods known in the art.

Ketones and ethers of the invention can also be synthesized according to the methods provided in Scheme 6, wherein q is an integer from 1 to 10 and $R^1$, $R^2$, m, n, and p are defined herein. Ketones of the invention can be synthesized by esterification of a carboxylic acid of formula A in acidic methanol followed by formation of the Weinreb Amide using N,O-dimethylhydroxylamine hydrochloride and isopropyl magnesium chloride. The Weinreb Amide can then be converted to a ketone using a Grignard reagent of the formula $(R^2)_p Ph(CH_2)nMgBr$. Ethers of the invention can by synthesized by esterification of a carboxylic acid of formula A in acidic methanol, followed by reduction with DIBAL to provide the primary alcohol. The alcohol is then alkylated to provide an ether using a base and an alkyl bromide of the formula $(R^2)pPh(CH_2)nBr$. It will also be Scheme 6.

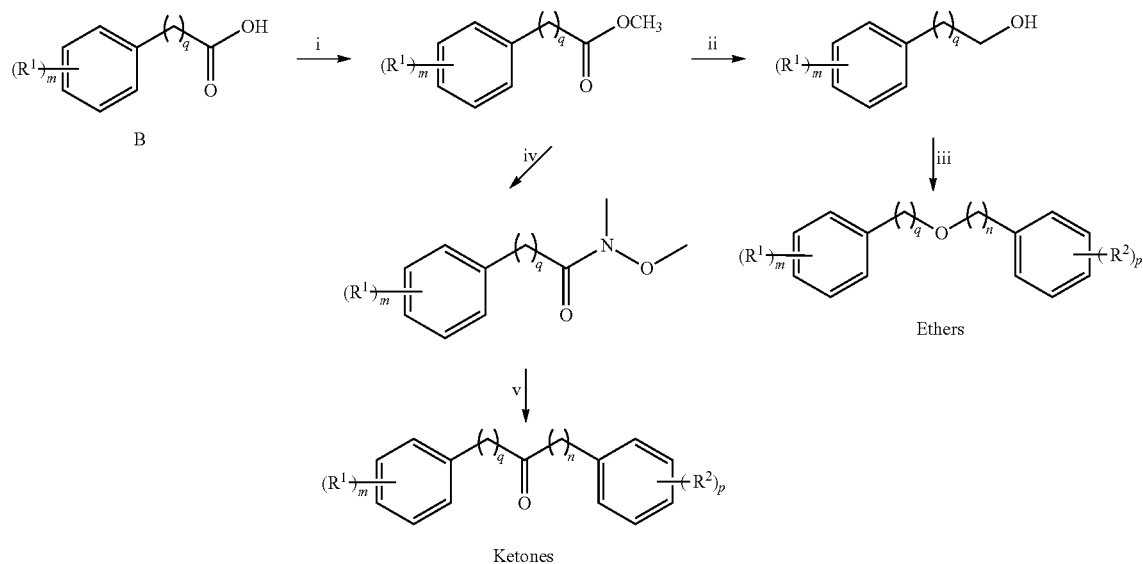

Ethers

Ketones

Reagents and conditions: i) MeOH, acid; ii) DIBAL; iii) base, $(R^2)pPh(CH_2)nBr$; iv) $CH_3NHOCH_3$—HCl, i-PrMgCl,; v) $(R^2)pPh(CH_2)nMgBr$.

understood that active $R^1$ and $R^2$ substituents, such as OH, $NH_2$, COOH, etc., can be protected using common methods known in the art.

Scheme 7.

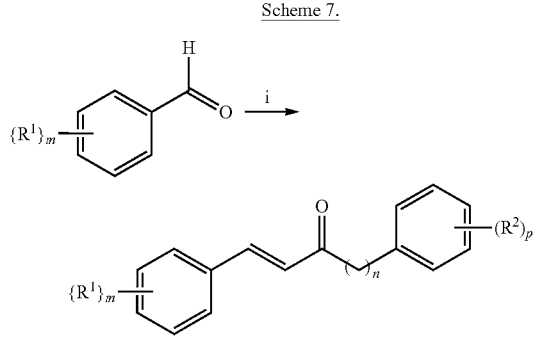

Reagents and conditions: i) Appropriate Methyl Ketone, Pyrrolidine, acetic acid, THF, reflux, 12 h.

Ketones can also be synthesized via an aldol condensation with the appropriate aldehyde and methyl ketone according to the method provided in Scheme 7, wherein $R^1$, $R^2$, m, n, and p are defined herein.

IV. Preparations and Examples

4-Phenylbutyl-3-(3,4-dihydroxyphenyl)propanoate (1)

(E)-4-phenylbutyl 3-(3,4-dihydroxyphenyl)acrylate was dissolved in MeOH (10 mL) and 10% Pd/C (0.1 eq) was added. The flask was sealed with a rubber septum and positive pressure of $H_2$ was maintained by a balloon attached via a syringe needle. The progress of the reactions was monitored by TLC until the complete conversion after 16 h. The reactions mixtures were filtered through celite and the solvent was removed under reduced pressure to give compound 1 (93% yield); $R_f$=0.7 (50% MeOH/$CH_2Cl_2$). $^1$H NMR (400 MHz, MeOD, 25° C.), δ (ppm)=7.28-7.16 (m, 5H, $H_{ar}$), 6.69-6.65 (m, 2H, $H_{ar}$), 6.52 (d, J=8.00 Hz, 1H, $H_{ar}$), 4.08-4.07 (m, 2H, C$\underline{H}_2$(CH$_2$)$_3$Ph), 2.77 (t, J=7.48 Hz, 2H, $C_{ar}$C$\underline{H}_2$CH$_2$C(=O)), 2.61-2.54 (m, 4H, (CH$_2$)$_3$C$\underline{H}_2$Ph, $C_{ar}$CH$_2$C$\underline{H}_2$C(=O)), 1.62-1.61 (m, 4H, CH$_2$(C$\underline{H}_2$)$_2$CH$_2$Ph). $^{13}$C NMR (101 MHz, MeOD, 25° C.), δ (ppm)=173.61, 144.82, 143.27, 142.00, 132.05, 128.03, 127.93, 125.38, 119.12, 115.03, 114.93, 63.98, 35.85, 34.95, 30.09, 27.85, 27.52; HRMS m/z calc. for $C_{19}H_{22}O_4$+($NH_4^+$): 332.1856; found: 332.1866.

5-Phenylpentyl-3-(3,4-dihydroxyphenyl)propanoate (2)

Compound 2 was obtained by hydrogenation of (E)-5-phenylpentyl 3-(3,4-dihydroxyphenyl)acrylate, following the procedure provided above for Compound 1 (78% yield); $R_f$=0.8 (5% MeOH/$CH_2Cl_2$). $^1$H NMR (400 MHz, CDCl$_3$, 25° C.), δ (ppm)=7.32-7.30 (m, 2H, $H_{ar}$), 7.22-7.19 (m, 2H, $H_{ar}$), 6.79 (d, J=8.04 Hz, 1H, $H_{ar}$), 6.73 (d, J=1.60 Hz, 1H, $H_{ar}$), 6.65 (dd, J=8.04 Hz, 1.68 Hz, 1H, $H_{ar}$), 4.08 (t, J=6.68 Hz, 2H, C$\underline{H}_2$(CH$_2$)$_4$Ph), 2.85 (t, J=7.56 Hz, 2H, $C_{ar}$C$\underline{H}_2$CH$_2$C(=O)), 2.61 (quint., J=7.60 Hz, 4H, (CH$_2$)$_4$C$\underline{H}_2$Ph, $C_{ar}$CH$_2$C$\underline{H}_2$C(=O)), 1.69-1.61 (m, 4H, CH$_2$C$\underline{H}_2$CH$_2$C$\underline{H}_2$CH$_2$Ph), 1.41-1.34 (m, 2H, (CH$_2$)$_2$C$\underline{H}_2$(CH$_2$)$_2$Ph)). $^{13}$C NMR (101 MHz, CDCl$_3$, 25° C.), δ (ppm)=173.22, 143.45, 142.44, 141.80, 133.68, 128.40, 128.31, 125.73, 120.72, 115.45, 115.39, 64.55, 36.11, 35.76, 31.04, 30.32, 28.46, 25.54; HRMS m/z calc. for $C_{20}H_{24}O_4$+($NH_4^+$): 346.2013; found: 346.2028.

6-Phenylhexyl-3-(3,4-dihydroxyphenyl)propanoate (3)

Compound 3 was obtained by hydrogenation of (E)-5-phenylhexyl 3-(3,4-dihydroxyphenyl)acrylate, following the procedure provided above for Compound 1 (93% yield; mp=72-74° C.; $R_f$=0.6 (5% MeOH/$CH_2Cl_2$)). $^1$H NMR (400 MHz, MeOD, 25° C.), δ (ppm)=7.32-7.30 (m, 2H, $H_{ar}$), 7.22-7.19 (m, 3H, $H_{ar}$), 6.77 (d, J=8.00 Hz, 1H, $H_{ar}$), 6.73 (s, 1H, $H_{ar}$), 6.64 (dd, J=7.96 Hz, 1.44 Hz, 1H, $H_{ar}$), 5.47 (s large, 1H, OH), 5.36 (s large, 1H, OH), 4.07 (t, J=6.68 Hz, 2H, C$\underline{H}_2$(CH$_2$)$_5$Ph), 2.85 (t, J=7.56 Hz, 2H, $C_{ar}$C$\underline{H}_2$CH$_2$C(=O)), 2.61 (q, J=8.96 Hz, 4H, (CH$_2$)$_5$C$\underline{H}_2$Ph, $C_{ar}$CH$_2$C$\underline{H}_2$C(=O)), 1.65-1.60 (m, 4H, CH$_2$C$\underline{H}_2$(CH$_2$)$_2$C$\underline{H}_2$CH$_2$Ph), 1.38-1.34 (m, 4H, (CH$_2$)$_2$(C$\underline{H}_2$)$_2$(CH$_2$)$_2$Ph). $^{13}$C NMR (101 MHz, MeOD, 25° C.), δ (ppm)=173.52, 143.54, 142.68, 141.92, 133.47, 128.41, 128.28, 125.67, 120.61, 115.41, 115.35, 64.76, 36.15, 35.86, 31.34, 30.33, 28.88, 28.52, 25.80; HRMS m/z calc. for $C_{21}H_{26}O_4$+($H^+$): 343.1904; found: 343.1922.

(2Z)-3-Phenylprop-2-en-1-yl (2E)-3-(3,4-dihydroxyphenyl)prop-2-enoate (4)

Compound 6 was obtained by the esterification of (E)-3-(3,4-dihydroxyphenyl)acrylic acid with (Z)-3-phenylallyl bromide, following the procedure provided above for Compound 4 (52% yield; purification by silica gel flash chromatography (0-40% AcOEt/Hex); $R_f$=0.20 (30% AcOEt/hexanes)). $^1$H NMR (400 MHz, DMSO-d$_6$, 25° C.), δ (ppm)=9.17-9.61 (m, 2H, OH), 7.50 (d, 1H, J=15.9 Hz, CH=CH—CO$_2$R), 7.42 (t, 2H, J=7.5 Hz, $H_{ar}$), 7.32 (m, 3H, $H_{ar}$), 7.06 (d, 1H, J=1.7 Hz, $H_{ar}$), 7.02 (dd, 1H, J=1.7, 8.2 Hz, $H_{ar}$), 6.77 (d, 1H, J=8.2 Hz, $H_{ar}$), 6.70 (d, 1H, J=11.7 Hz, CH$_2$—CH=C$\underline{H}$), 6.30 (d, 1H, J=15.9 Hz, CH=C$\underline{H}$—CO$_2$R), 5.60 (td, 1H, J=6.4, 11.8 Hz, CH$_2$—C$\underline{H}$=CH), 4.91 (dd, 2H, J=1.1, 6.4 Hz, OCH$_2$); $^{13}$C NMR (101 MHz, DMSO-d$_6$, 25° C.), δ (ppm)=166.82, 148.96, 146.04, 145.95, 136.25, 132.52, 129.11, 128.94, 128.04, 127.03, 125.92, 121.95, 116.20, 115.33, 114.08, 61.28; HRMS m/z calc. for $C_{18}H_{16}O_4$+($Na^+$): 319.0941; found: 319.0939.

3-Phenylpropyl (2E)-3-(2-hydroxyphenyl)prop-2-enoate (5)

To a solution of 3-(2-hydroxyphenyl) acrylic acid (500 mg) in 5 mL of HMPA was added Na$_2$CO$_3$ (1.2 eq) and the mixture was stirred for 30 minutes in an ice bath. 2-phenylethyl bromide, dissolved in 1 mL of HMPA, was then added drop by drop over 20 minutes followed by a catalytic amount of KI. The mixture was stirred at room temperature for 12 hours, and then the reaction was poured into 50 mL of ice water and stirred for 30 minute. The resulting mixture was then extracted with ethyl acetate (3×40 mL) and the combined organic phases were washed with water (3×25 mL), brine (3×25 mL), and dried over MgSO$_4$. The solution was then filtered and concentrated, then purified by flash chromatography (0-70% AcOEt/hexanes) to provide Compound 4. mp=94-95° C., $R_f$=0.6 (30% AcOEt/hexanes). $^1$H NMR (400 MHz, DMSO-d6, 25° C.), δ (ppm)=10.24 (s, 1H, OH), 7.88 (d, 1H, J=16.2 Hz, Ar—CH=CH), 7.6 (dd, 1H, J=1.4, 7.8 Hz, $H_{ar}$), 7.24 (m, 6H, $H_{ar}$), 6.92 (d, 1H, J=8.1 Hz, $H_{ar}$), 6.84 (t, 1H, J=7.4 Hz, H$_{ar}$), 6.62 (d, 1H, J=16.2 Hz, CH=CH—CO), 4.13 (t, 2H, J=6.6 Hz, CH$_2$O), 2.69 (t, 2H, J=8.0 Hz, CH$_2$Ph), 1.96 (m, 2H, CH$_2$CH$_2$CH$_2$), $^{13}$C NMR (101 MHz, DMSO-d6, 25° C.), δ (ppm)=167.23, 157.24, 141.64, 140.57, 132.18, 129.38, 128.82, 128.77, 126.34, 121.17, 119.88, 117.57, 116.63, 63.67, 31.93, 30.35; HRMS m/z calc. for C$_{18}$H$_{16}$O$_3$+(H$^+$): 283.1329; found: 283.1340.

3-Phenylpropyl (2E)-3-(4-hydroxy-3,5-dimethoxyphenyl)prop-2-enoate (6)

Compound 5 was obtained by the esterification of 3-(4-hydroxy-3,5-dimethoxyphenyl)acrylic acid with 2-phenylethyl bromide, following the procedure provided above for Compound 4 (48% yield; purification by silica gel flash chromatography (0-15% AcOEt/Hex); mp=94-95° C., R$_f$=0.35 (30% AcOEt/hexanes)). $^1$H NMR (400 MHz, DMSO-d6, 25° C.), δ (ppm)=8.96 (s, 1H, OH), 7.55 (d, 1H, J=15.9 Hz, Ar—CH=CH), 7.30 (m, 2H, H$_{ar}$), 7.22 (m, 3H, H$_{ar}$), 7.04 (s, 2H, H$_{ar}$), 6.55 (d, 1H, J=15.9 Hz, CH=CH—CO), 4.12 (t, 2H, J=6.5 Hz, CH$_2$O), 3.81 (s, 6H, OCH$_3$), 2.7 (t, 2H, J=8.0 Hz, CH$_2$Ph), 1.96 (m, 2H, CH$_2$CH$_2$CH$_2$), $^{13}$C NMR (101 MHz, DMSO-d6, 25° C.), δ (ppm)=167.14, 148.49, 145.82, 141.67, 138.77, 128.83, 128.78, 126.35, 124.87, 115.33, 106.73, 63.60, 56.56, 31.98, 30.37; HRMS m/z calc. for C$_{20}$H$_{22}$O$_5$+(H$^+$): 343.1540; found: 343.1543.

2-Phenylethyl (2E)-3-(3,4-dichlorophenyl)prop-2-enoate (7)

Compound 7 was obtained by the esterification of (E)-3-(3,4-dichlorophenyl)acrylic acid with 2-phenylethyl bromide, following the procedure provided above for Compound 4 (70% yield; purification by silica gel flash chromatography (0-20% AcOEt/Hex); mp=68-69° C., R$_f$=0.3 (10% AcOEt/hexanes)). $^1$H NMR (400 MHz, CDCl$_3$, 25° C.), δ (ppm)=7.62 (d, J=1.89 Hz, 1H, H$_{ar}$), 7.57 (d, J=16.05 Hz, 1H, C$_{ar}$—CH=CH), 7.48 (d, J=8.32 Hz, 1H, H$_{ar}$), 7.37-7.33 (m, 3H, H$_{ar}$), 7.29-7.26 (m, 3H, H$_{ar}$), 6.42 (d, J=16.01 Hz, 1H, CH=CH—CO), 4.46 (t, J=7.04 Hz, 2H, CH$_2$O), 3.04 (t, J=7.00 Hz, 2H, CH$_2$Ph), $^{13}$C NMR (101 MHz, CDCl$_3$, 25° C.), δ=(ppm): 166.27, 142.08, 137.74, 134.44, 134.22, 133.26, 130.90, 129.62, 128.92, 128.56, 127.04, 126.65, 119.95, 65.29, 35.15; HRMS m/z calc. for C$_{17}$H$_{14}$Cl$_2$O$_2$+(H$^+$): 321.0444; found: 321.0441.

2-Phenylethyl (2E)-3-(naphthalen-2-yl)prop-2-enoate (8)

Compound 8 was obtained by the esterification of (E)-3-(naphthalen-2-yl)acrylic acid with 2-phenylethyl bromide, following the procedure provided above for Compound 4 (70% yield; purification by silica gel flash chromatography (0-5% AcOEt/Hex); mp=77-78° C., R$_f$=0.4 (30% AcOEt/hexanes)). $^1$H-NMR (400 MHz, CDCl$_3$, 25° C.), δ (ppm)=7.95-7.85 (m, 5H, H$_{ar}$, C$_{ar}$—CH=CH), 7.69 (dd, J=8.64 Hz, 1.08 Hz, 1H, H$_{ar}$), 7.57-7.52 (m, 2H, H$_{ar}$), 7.39-7.27 (m, 5H, H$_{ar}$), 6.57 (d, J=16.01 Hz, 1H, CH=CH—CO), 4.92 (t, J=7.08 Hz, 2H, CH$_2$O), 3.08 (t, J=7.08 Hz, 2H, CH$_2$Ph); $^{13}$C NMR (101 MHz, CDCl$_3$, 25° C.), δ (ppm)=166.98, 144.92, 137.94, 134.25, 133.3, 131.93, 129.96, 128.97, 128.70, 128.59, 128.56, 127.80, 127.26, 126.74, 126.61, 123.54, 118.22, 65.07, 35.26; HRMS m/z calc. for C$_{21}$H$_{18}$O$_2$+(H$^+$): 303.138; found: 303.1387.

2-Phenethyl (2E)-3-(3,5-dimethoxyphenyl)acrylate (9)

Compound 9 was obtained by the esterification of (E)-3-(3,5-dimethoxyphenyl)acrylic acid with 2-phenylethyl bromide, following the procedure provided above for Compound 4 (72% yield; purification by silica gel flash chromatography (0-40% AcOEt/Hex); mp=55-57° C., R$_f$=0.3 (30% AcOEt/hexanes)). $^1$H NMR (400 MHz, CDCl$_3$), δ (ppm): 7.61 (d, 1H, J=15.97 Hz, ArCH=CH—), 7.37-7.27 (m, 5H, H$_{ar}$), 6.69-6.68 (m, 2H, H$_{ar}$), 6.53-6.52 (m, 1H, H$_{ar}$), 6.42 (d, 1H, J=15.97 Hz, ArCH=CH—), 4.46 (t, 2H, J=7.04 Hz, —COOCH$_2$CH$_2$Ar), 3.84 (s, 6H, 2 ArOCH$_3$), 3.05 (t, 2H, J=7.08 Hz, —COOCH$_2$CH$_2$Ar); $^{13}$C NMR (101 MHz, CDCl$_3$), δ (ppm): 166.79, 161.03, 144.86, 137.87, 136.29, 128.93, 128.54, 126.59, 118.57, 105.99, 102.58, 65.04, 55.44, 35.21; HRMS m/z calc. for C$_{19}$H$_{20}$O$_4$+(H$^+$): 313.1434; found: 313.1440.

3-Phenylpropyl (E)-3-(3,5-dimethoxyphenyl)acrylate (10)

Compound 10 was obtained by the esterification of (E)-3-(3,5-dimethoxyphenyl)acrylic acid with 3-phenylpropyl bromide, following the procedure provided above for Compound 4 (76% yield; purification by silica gel flash chromatography (0-40% AcOEt/Hex); R$_f$=0.2 (30% AcOEt/hexanes)). $^1$H NMR (400 MHz, CDCl$_3$), δ (ppm): 7.62 (d, 1H, J=15.97 Hz, ArCH=CH—), 7.34-7.21 (m, 5H, H$_{ar}$), 6.70-6.69 (m, 2H, H$_{ar}$), 6.53-6.52 (m, 1H, H$_{ar}$), 6.44 (d, 1H, J=15.93 Hz, ArCH=CH—), 4.26 (t, 2H, J=6.52 Hz, —COOCH$_2$CH$_2$CH$_2$Ar), 3.84 (s, 6H, 2 ArOCH$_3$), 2.78 (t, 2H, J=7.40 Hz, —COOCH$_2$CH$_2$Ar), 2.08 (quint, 2H, J=6.60 Hz, —COOCH$_2$CH$_2$CH$_2$Ar); $^{13}$C NMR (101 MHz, CDCl$_3$), δ (ppm): 166.90, 161.03, 144.72, 141.24, 136.32, 128.46, 128.44, 126.02, 118.65, 105.97, 102.60, 63.96, 55.44, 32.27, 30.30; HRMS m/z calc. for C$_{20}$H$_{22}$O$_4$+(H$^+$): 327.1591; found: 327.1581.

3-Phenylpropyl (E)-3-(2,5-dimethoxyphenyl)acrylate (11)

Compound 11 was obtained by the esterification of (E)-3-(2,5-dimethoxyphenyl)acrylic acid with 3-phenylpropyl bromide, following the procedure provided above for Compound 4 (78% yield; purification by silica gel flash chromatography (0-40% AcOEt/Hex); R$_f$=0.2 (30% AcOEt/hexanes)). $^1$H NMR (400 MHz, CDCl$_3$), δ (ppm): 8.02 (d, 1H, J=16.17 Hz, ArCH=CH—), 7.34-7.21 (m, 5H, H$_{ar}$), 7.09-7.08 (m, 1H, H$_{ar}$), 6.96-6.93 (m, 1H, H$_{ar}$), 6.89-6.87 (m, 1H, H$_{ar}$), 6.54 (d, 1H, J=16.17 Hz, ArCH=CH—), 4.26 (t, 2H, J=6.52 Hz, —COOCH$_2$CH$_2$CH$_2$Ar), 3.88 (s, 3H, ArOCH$_3$ ortho), 3.82 (s, 3H, ArOCH$_3$ meta), 2.78 (t, 2H, J=7.44 Hz, —COOCH$_2$CH$_2$CH$_2$Ar), 2.08 (quint, 2H, J=6.72 Hz, —COOCH$_2$CH$_2$CH$_2$Ar); $^{13}$C NMR (101 MHz, CDCl$_3$), δ (ppm): 167.40, 153.52, 152.85, 141.33, 139.92, 128.45, 125.99, 123.99, 118.84, 117.13, 113.29, 112.46, 63.77, 56.10, 55.80, 32.24, 30.37; HRMS m/z calc. for C$_{20}$H$_{22}$O$_4$+(H$^+$): 327.1591; found: 327.1599.

3-Phenylpropyl (E)-3-(2,3-dimethoxyphenyl)acrylate (12)

Compound 12 was obtained by the esterification of (E)-3-(2,3-dimethoxyphenyl)acrylic acid with 3-phenylpropyl bromide, following the procedure provided above for Compound 4 (63% yield; purification by silica gel flash chromatography (0-40% AcOEt/Hex); mp=102-104° C., R$_f$=0.2 (30% AcOEt/hexanes)). $^1$H NMR (400 MHz, CDCl$_3$, 25° C.), δ (ppm): 8.04 (d, 1H, J=16.21 Hz, ArCH=CH—), 7.34-7.22 (m, 5H, H$_{ar}$), 7.20-7.18 (m, 1H, H$_{ar}$), 7.11-7.07 (m, 1H, H$_{ar}$), 6.98-6.96 (m, 1H, H$_{ar}$), 6.53 (d, 1H, J=16.21

Hz, ArCH=CH—), 4.26 (t, 2H, J=6.56 Hz, —COOCH$_2$CH$_2$CH$_2$Ar), 3.91 (s, 3H, ArOCH$_3$ ortho), 3.89 (s, 3H, ArOCH$_3$ meta), 2.78 (t, 2H, J=7.36 Hz, —COOCH$_2$CH$_2$CH$_2$Ar), 2.08 (quint, 2H, J=6.56 Hz, —COOCH$_2$CH$_2$CH$_2$Ar); $^{13}$C NMR (101 MHz, CDCl$_3$), δ (ppm)=167.19, 153.16, 148.48, 141.29, 139.46, 128.65, 128.45, 126.00, 124.18, 119.46, 119.26, 113.95, 63.81, 61.33, 55.89, 32.23, 30.36; HRMS m/z calc. for C$_{20}$H$_{22}$O$_4$+(H$^+$): 327.1591; found: 327.1599.

Phenethyl (E)-3-[3,5-bis(trifluoromethyl)phenyl]acrylate (13)

Compound 13 was obtained by the esterification of (E)-3-[3,5-bis(trifluoromethyl)phenyl]acrylic acid with 2-phenylethyl bromide, following the procedure provided above for Compound 4 (70% yield; purification by silica gel flash chromatography (0-40% AcOEt/Hex); R$_f$=0.25 (30% AcOEt/hexanes)). $^1$H NMR (400 MHz, CDCl$_3$), δ (ppm): 7.95 (s, 2H, H$_{ar}$), 7.90 (s, 1H, H$_{ar}$), 7.72 (d, 1H. J=16.09 Hz, ArCH=CH—), 7.38-7.26 (m, 5H, H$_{ar}$), 6.58 (d, 1H, J=16.05 Hz, ArCH=CH—), 4.49 (t, 2H, J=7.04 Hz, —COOCH$_2$CH$_2$Ar), 3.06 (t, 2H, J=7.00 Hz, —COOCH$_2$CH$_2$Ar); $^{13}$C NMR (101 MHz, CDCl$_3$), δ (ppm): 165.74, 141.17, 137.61, 136.50, 132.98-131.98, 128.89, 128.60, 127.68, 127.65, 127.06, 126.70, 124.35, 123.47-123.32, 122.08, 121.63, 65.47, 35.11; $^{19}$F NMR (376 MHz, CDCl$_3$), δ (ppm) 63.09 (2 ArCF$_3$); HRMS m/z calc. for C$_{19}$H$_{14}$F$_6$O$_2$+(NH$_4^+$): 406.1236; found: 406.1233.

3-Phenylpropyl (E)-3-(2,4-dihydroxyphenyl)acrylate (14)

Compound 14 was obtained by the esterification of (E)-3-(2,4-dihydroxyphenyl)acrylic acid with 3-phenylpropyl bromide, following the procedure provided above for Compound 4 (66% yield; purification by silica gel flash chromatography (0-60% AcOEt/Hex); mp=46-48° C., R$_f$=0.20 (30% AcOEt/hexanes). $^1$H NMR (400 MHz, DMSO), δ (ppm): 10.14 (s, 1H, ArOH ortho), 9.87 (s, 1H, ArOH para), 7.79 (d, 1H, J=16.05 Hz, ArCH=CH—), 7.44-7.42 (m, 1H, H$_{ar}$), 7.31-7.17 (m, 5H, H$_{ar}$), 6.40 (d, 1H, J=16.05 Hz, ArCH=CH—), 6.37-6.36 (m, 1H, H$_{ar}$), 6.29-6.27 (m, 1H, H$_{ar}$), 4.10 (t, 2H, J=6.56 Hz, —COOCH$_2$CH$_2$CH$_2$Ar), 2.68 (t, 2H, J=7.96 Hz, —COOCH$_2$CH$_2$CH$_2$Ar), 1.94 quint, 2H, J=6.64 Hz, —COOCH$_2$CH$_2$CH$_2$Ar); $^{13}$C NMR (101 MHz, DMSO), δ (ppm): 167.69, 161.42, 158.99, 141.68, 140.97, 130.88, 128.81, 128.76, 126.33, 113.38, 113.05, 108.27, 102.93, 63.32, 31.95, 30.43; HRMS m/z calc. for C$_{18}$H$_{18}$O$_4$+(H$^+$): 299.1278; found: 299.1283.

Compounds 60-154 can be synthesized by methods known to those having skill in the art and/or analogously to the methods described herein.

Biological Assays

Isolation of Neutrophils from Peripheral Blood

Neutrophils (PMN) were isolated from heparinized blood obtained from healthy donors as previously described (Boyum, 1968). Briefly, blood was centrifuged at 300×g for 5 min at room temperature, plasma was collected and erythrocytes were removed after dextran sedimentation. Following centrifugation on a lymphocyte separation medium cushion (density, 1.077 g/ml) at 900 g for 20 min at room temperature, PMN (>96%) were obtained from the pellet after hemolysis to remove contaminating erythrocytes.

Stimulation of PMN for 5-LO products

Isolated PMN (1×10$^7$ cells/mL) resuspended in Hank's balanced salt solution (HBSS, Lonza, Walkerville, MD) containing 1.6 mM CaCl$_2$ were pre-incubated with test compounds for 5 min at 37° C. in the presence of 1 U/mL of adenosine deaminase. Cells were then stimulated for 15 min at 37° C. with the addition of 1 µM thapsigargin with or without 10 µM arachidonic acid (Flamand et al., 2002; Boudreau et al, 2012). Reactions were stopped with the addition of 0.5 volume of cold MeOH:CH$_3$CN (1:1) and 50 ng of PGB$_2$ as internal standard, and samples were stored at −20° C. overnight for protein denaturation. Samples were then centrifuged at 12,000×g for 5 min, supernatants were collected and subjected to automated in-line solid phase extraction on Oasis HLB columns prior to reverse-phase high-performance liquid chromatography analysis with diode array detection (Borgeat et al., 1990). Total 5-LO products quantified represents the sum of LTB$_4$, its trans isomers, 20-COOH— and 20-OH-LTB$_4$ and 5-hydroxyeicosatetraenoic acid.

Ex Vivo Whole Blood Stimulation

Zymosan stimulation of whole blood was performed as previously described (Surette et al., 1994) with minor modifications. Each compound or its diluent was added to heparinized blood obtained from healthy donors (1 mL) at the indicated concentration and incubated for 10 min at 37° C. in a water bath. Following incubations, 125 µL of 40 mg/mL opsonised zymosan was added to each sample, gently vortexed and incubated for 30 min at 37° C. Samples were then centrifuged for 10 min at 960×g at 4° C. Plasma, 350 µL, was removed and added to 1.2 ml of methanol:acetonitrile (1:1) and 50 ng of PGB$_2$ as internal standard. Samples were left overnight at −20° C. for protein denaturation. Samples were then centrifuged at 12,000×g for 5 min, supernatants were collected and subjected to automated in-line solid phase extraction on Oasis HLB columns prior to reverse-phase high-performance liquid chromatography analysis with diode array detection (Borgeat et al., 1990). Total 5-LO products quantified represents the sum of LTB$_4$, its trans isomers, 20-COOH— and 20-OH-LTB$_4$ and 5-hydroxyeicosatetraenoic acid.

Stimulation of HEK293 Cells

HEK293 cells that were stably transfected with vectors expressing 5-LO and FLAP were utilized (Boudreau et al., NJC 2009). HEK293 cells were detached by trypsinization and re-suspended in Hank's balanced salt solution containing 1.6 mM CaCl$_2$. Cells (1×10$^6$ cells/mL) were preincubated at 37° C. with the test compounds or their diluent for 5 minutes and were then stimulated at 37° C. with 10 µM ionophore A23187 and 10 µM AA for 15 min. Stimulations were stopped by adding 0.5 volumes of a methanol:acetonitrile (1:1) solution containing 100 ng/mL each of PGB$_2$ and 19-OH-PGB$_2$ as internal standards, and samples were then kept at −20° C. overnight for protein denaturation. Samples were then centrifuged at 12,000×g for 5 min, supernatants were collected and subjected to automated in-line solid phase extraction on Oasis HLB columns prior to reverse-phase high-performance liquid chromatography analysis with diode array detection (Borgeat et al., 1990). Total 5-LO products quantified represents the sum of LTB$_4$, its trans isomers and 5-hydroxyeicosatetraenoic acid.

Results:

TABLE 10a 5-lipoxygenase Inhibitory Activity of Compounds Of The Present Invention

| Molecule/ Cmpd # | HEK293 cells | HEK Dose-response | PMN | PMN + exogenous AA | PMN dose-response | PMN dose-response + exogenous AA | Whole Blood | Whole blood dose-response |
|---|---|---|---|---|---|---|---|---|
| CAPE | ✓ | 0.65-1.2 | ✓ | ✓ | 0.84-1.1 | n/d | ✓ | 3.4 |
| Zileuton | ✓ | 6.6-8.9 | ✓ | ✓ | 2.5-3.2 | n/d | ✓ | 1.7 |
| 1 | | | ✓ | | 0.87 | | ✓ | n/d |
| 2 | | | ✓ | | 0.86 | | ✓ | 2.8 |
| 3 | | | ✓ | | 0.51 | | ✓ | 2.4 |
| 7 | ✓ | | ✓ | | n/d | | n/d | |
| 8 | ✓ | | ✓ | | n/d | | n/d | |
| 6 | ✓ | | ✓ | ✓n = 1 | 0.35 | | ✓ | |
| 4 | ✓ | | ✓ | ✓n = 1 | 0.76 | | ✓ | |
| 9 | ✓ | | n/d | | | | | |
| 13 | ✓ | | n/d | | | | | |
| 14 | ✓ | | n/d | | | | | |
| 12 | ✓ | | n/d | | | | | |
| 10 | ✓ | | n/d | | | | | |
| 15 | | | ✓ | | n/d | | | |
| 16 | | | ✓ | | n/d | | | |
| 17 | | | ✓ | | 0.86 | | ✓ | n/d |
| 18 | | | ✓ | | n/d | | | |
| 19 | | | ✓ | | n/d | | | |
| 20 | | | ✓ | | n/d | | | |
| 21 | | | ✓ | | n/d | | | |
| 22 | | | ✓ | | n/d | | | |
| 23 | | | ✓ | | n/d | | | |
| 24 | | | ✓ | | n/d | | | |
| 25 | ✓ | | ✓ | | 0.59-0.82 | | ✓ | n/d |
| 26 | | | ✓ | | n/d | | | |
| 27 | | | ✓ | | 0.72 | | ✓ | n/d |
| 39 | | | ✓ | | 0.60 | | ✓ | n/d |
| 40 | | | ✓ | | 0.53 | | ✓ | n/d |
| 41 | | | ✓ | | 0.84 | | ✓ | n/d |
| 55 | | | ✓ | | 1.6 | | ✓ | n/d |
| 56 | | | ✓ | | 0.92 | | ✓ | n/d |
| 32 | ✓ | | ✓ | | 1.0 | | ✓ | n/d |
| 33 | | | ✓ | | 0.89 | | ✓ | n/d |
| 34 | ✓ | | ✓ | | n/d | | | |
| 35 | | | ✓ | | 0.79 | | ✓ | n/d |
| 36 | ✓ | | ✓ | | n/d | | | |
| 37 | ✓ | | ✓ | | n/d | | | |
| 44 | ✓ | | ✓ | | n/d | | n/d | |
| 42 | ✓ | | n/d | | n/d | | n/d | |
| 43 | ✓ | | n/d | | n/d | | n/d | |
| 38 | ✓ | | ✓ | | 0.79 | | ✓ | 2.8 |
| 29 | ✓ | | n/d | | n/d | | n/d | |
| 30 | ✓ | | n/d | | n/d | | n/d | |
| 31 | ✓ | | ✓ | | 1.03 | | ✓ | n/d |
| 57 | ✓ | | ✓ | | n/d | | n/d | |
| 59 | ✓ | | ✓ | | 0.84 | | ✓ | n/d |
| 58 | ✓ | | ✓ | | n/d | | n/d | |
| 48 | ✓ | | ✓ | ✓n = 1 | n/d | | n/d | n/d |
| 47 | ✓ | | ✓ | ✓n = 1 | n/d | | n/d | n/d |
| 46 | ✓ | | ✓ | n/d | n/d | | n/d | n/d |
| 45 | ✓ | | ✓ | ✓n = 1 | 0.30 | | ✓ | |
| 49 | ✓ | | ✓ | n/d | n/d | | n/d | n/d |
| 50 | ✓ | | ✓ | n/d | n/d | | n/d | n/d |
| 51 | ✓ | | n/d | | | | | |
| 52 | ✓ | | n/d | | | | | |
| 53 | ✓ | | n/d | | | | | |
| 54 | ✓ | | n/d | | | | | |
| 28 | ✓ | | | | | | | |
| 11 | ✓ | | n/d | | | | | |

✓ = compound screened for inhibition at 1 μM.
n/d: indicates that further testing will not be done because of inadequate inhibition at initial screening. Note, a designation of n/d indicates that the compounds were not better than CAPE at 1 μM. Some of these compounds may inhibit at low μM concentrations but our screen was to identify compounds that performed equal to or better than CAPE.
For dose-response tests, if a value is given the test was performed. All values are IC50 in μM.
Ranges indicate confidence interval.
Empty cell = not yet tested.

TABLE 10b 5-lipoxygenase Inhibitory Activity of Compounds Of The Present Invention

| Compound | HEK293 cells | HEK Dose-response | PMN | PMN + exogenous AA | PMN dose-response | PMN dose-response + exogenous AA | Whole Blood | Whole blood dose-response |
|---|---|---|---|---|---|---|---|---|
| CAPE | ✓ | 0.65-1.2 | ✓ | ✓ | 0.84-1.1 | | ✓ | 3.4 |
| Zileuton | ✓ | 6.6-8.9 | ✓ | ✓ | 2.5-3.2 | | ✓ | 1.7 |
| 60 | ✓ | — | ✓ | | n/d | | n/d | |
| 61 | ✓ | — | ✓ | | n/d | | n/d | |
| 62 | ✓ | n/d | n/d | | n/d | | n/d | |
| 63 | ✓ | n/d | n/d | | n/d | | n/d | |
| 64 | ✓ | — | ✓ | | | | | |
| 65 | ✓ | n/d | n/d | | n/d | | n/d | |
| 66 | ✓ | — | ✓ | | n/d | | n/d | |
| 67 | ✓ | n/d | n/d | | n/d | | n/d | |
| 68 | ✓ | n/d | n/d | | n/d | | n/d | |
| 69 | ✓ | — | ✓ | | n/d | | n/d | |
| 70 | ✓ | n/d | n/d | | n/d | | n/d | |
| 71 | ✓ | n/d | n/d | | n/d | | n/d | |
| 72 | ✓ | n/d | n/d | | n/d | | n/d | |
| 73 | ✓ | n/d | n/d | | n/d | | n/d | |
| 74 | ✓ | n/d | n/d | | n/d | | n/d | |
| 75 | ✓ | n/d | n/d | | n/d | | n/d | |

TABLE 10c 5-lipoxygenase Inhibitory Activity of Compounds Of The Present Invention

| Compound | HEK293 cells | HEK Dose-response | PMN | PMN + exogenous AA | PMN dose-response | PMN dose-response + exogenous AA | Whole Blood | Whole blood dose-response |
|---|---|---|---|---|---|---|---|---|
| CAPE | ✓ | 0.65-1.2 | ✓ | ✓ | 0.84-1.1 | | ✓ | 3.4 |
| Zileuton | ✓ | 6.6-8.9 | ✓ | ✓ | 2.5-3.2 | | ✓ | 1.7 |
| 76 | ✓ | | | | | | | |
| 77 | ✓ | | n/d | | | | | |
| 78 | ✓ | | n/d | | | | | |
| 79 | | | | | | | | |
| 80 | ✓ | | n/d | | | | | |
| 81 | ✓ | | n/d | | | | | |
| 82 | ✓ | | n/d | | | | | |
| 83 | ✓ | | n/d | | | | | |
| 84 | ✓ | | ✓ | | | | | |
| 85 | ✓ | | n/d | | | | | |
| 86 | ✓ | | n/d | | | | | |
| 87 | ✓ | | n/d | | | | | |

TABLE 10d 5-lipoxygenase Inhibitory Activity of Compounds Of The Present Invention

| Compound | HEK293 cells | HEK Dose-response | PMN | PMN + exogenous AA | PMN dose-response | PMN dose-response + exogenous AA | Whole Blood | Whole blood dose-response |
|---|---|---|---|---|---|---|---|---|
| CAPE | ✓ | 0.65-1.2 | ✓ | ✓ | 0.84-1.1 | | ✓ | 3.4 |
| Zileuton | ✓ | 6.6-8.9 | ✓ | ✓ | 2.5-3.2 | | ✓ | 1.7 |
| 88 | ✓ | | n/d | | | | | |
| 89 | ✓ | | n/d | | | | | |
| 90 | ✓ | | n/d | | | | | |
| 91 | ✓ | | n/d | | | | | |
| 92 | ✓ | | n/d | | | | | |
| 93 | ✓ | | n/d | | | | | |
| 94 | ✓ | | n/d | | | | | |
| 95 | ✓ | | n/d | | | | | |
| 96 | ✓ | | n/d | | | | | |
| 97 | ✓ | | n/d | | | | | |
| 98 | ✓ | | n/d | | | | | |
| 99 | ✓ | | n/d | | | | | |
| 100 | ✓ | | n/d | | | | | |
| 101 | ✓ | | n/d | | | | | |
| 102 | ✓ | | n/d | | | | | |

TABLE 10d-continued 5-lipoxygenase Inhibitory Activity of Compounds Of The Present Invention

| Compound | HEK293 cells | HEK Dose-response | PMN | PMN + exogenous AA | PMN dose-response | PMN dose-response + exogenous AA | Whole Blood | Whole blood dose-response |
|---|---|---|---|---|---|---|---|---|
| 103 | ✓ | | n/d | | | | | |
| 104 | ✓ | | n/d | | | | | |
| 105 | ✓ | | n/d | | | | | |

TABLE 10e 5-lipoxygenase Inhibitory Activity of Compounds Of The Present Invention

| Compound | HEK293 cells | HEK Dose-response | PMN | PMN + exogenous AA | PMN dose-response | PMN dose-response + exogenous AA | Whole Blood | Whole blood dose-response |
|---|---|---|---|---|---|---|---|---|
| CAPE | ✓ | 0.65-1.2 | ✓ | ✓ | 0.84-1.1 | n/d | ✓ | 3.4 |
| Zileuton | ✓ | 6.6-8.9 | ✓ | ✓ | 2.5-3.2 | n/d | ✓ | 1.7 |
| 106 | ✓ | | n/d | | | | | |
| 107 | ✓ | | | | | | | |
| 108 | | | | | | | | |
| 109 | | | | | | | | |
| 110 | ✓ | | | | | | | |
| 111 | | | | | | | | |
| 112 | | | | | | | | |
| 113 | ✓ | | | | | | | |
| 114 | | | | | | | | |
| 115 | | | | | | | | |
| 116 | | | | | | | | |
| 117 | | | | | | | | |
| 118 | | | | | | | | |
| 119 | ✓ | | n/d | | | | | |
| 120 | ✓ | | n/d | | | | | |
| 121 | ✓ | | n/d | | | | | |
| 122 | ✓ | | n/d | | | | | |
| 123 | ✓ | | n/d | | | | | |
| 124 | ✓ | | n/d | | | | | |
| 125 | ✓ | | ✓ | | 0.58-0.80 | | | |
| 126 | ✓ | | n/d | | | | | |
| 127 | ✓ | | ✓ | | 0.64-0.83 | | | |
| 128 | ✓ | | ✓ | | 0.30-0.36 | | | |
| 129 | ✓ | | n/d | | | | | |

TABLE 10f 5-lipoxygenase Inhibitory Activity of Compounds Of The Present Invention

| Compound | HEK293 cells | HEK Dose-response | PMN | PMN + exogenous AA | PMN dose-response | PMN dose-response + exogenous AA | Whole Blood | Whole blood dose-response |
|---|---|---|---|---|---|---|---|---|
| CAPE | ✓ | 0.65-1.2 | ✓ | ✓ | 0.84-1.1 | n/d | ✓ | 3.4 |
| Zileuton | ✓ | 6.6-8.9 | ✓ | ✓ | 2.5-3.2 | n/d | ✓ | 1.7 |
| 130 | ✓ | | ✓ | | | | | |
| 131 | ✓ | | ✓ | | | | | |
| 132 | ✓ | | n/d | | | | | |
| 133 | | | | | | | | |
| 134 | ✓ | | | | | | | |
| 135 | ✓ | | n/d | | | | | |
| 136 | | | | | | | | |
| 137 | | | | | | | | |

TABLE 10g 5-lipoxygenase Inhibitory Activity of Compounds Of The Present Invention

| Compound | HEK293 cells | HEK Dose-response | PMN | PMN + exogenous AA | PMN dose-response | PMN dose-response + exogenous AA | Whole Blood | Whole blood dose-response |
|---|---|---|---|---|---|---|---|---|
| CAPE | ✓ | 0.65-1.2 | ✓ | ✓ | 0.84-1.1 | n/d | ✓ | 3.4 |
| Zileuton | ✓ | 6.6-8.9 | ✓ | ✓ | 2.5-3.2 | n/d | ✓ | 1.7 |
| Gallic Acid | | | | | | | | |
| 138 | ✓ | | n/d | | | | | |
| 139 | ✓ | | n/d | | | | | |
| 140 | ✓ | | n/d | | | | | |
| 141 | ✓ | | n/d | | | | | |
| 142 | ✓ | | n/d | | | | | |
| 143 | ✓ | | n/d | | | | | |
| 144 | ✓ | | n/d | | | | | |
| 145 | ✓ | | ✓ | | | | | |
| 146 | ✓ | | n/d | | | | | |

TABLE 10h 5-lipoxygenase Inhibitory Activity of Compounds Of The Present Invention

| Compound | HEK293 cells | HEK Dose-response | PMN | PMN + exogenous AA | PMN dose-response | PMN dose-response + exogenous AA | Whole Blood | Whole blood dose-response |
|---|---|---|---|---|---|---|---|---|
| CAPE | ✓ | 0.65-1.2 | ✓ | ✓ | 0.84-1.1 | n/d | ✓ | 3.4 |
| Zileuton | ✓ | 6.6-8.9 | ✓ | ✓ | 2.5-3.2 | n/d | ✓ | 1.7 |
| 147 | ✓ | | n/d | | | | | |
| 148 | ✓ | | n/d | | | | | |
| 149 | | | | | | | | |
| 150 | | | | | | | | |
| 151 | ✓ | | ✓ | | | | | |
| 152 | ✓ | | ✓ | | | | | |
| 153 | | | | | | | | |
| 154 | | | | | | | | |

Tables 11a and 11b below provide exemplary Cyclooxygenase-2 (COX-2) Inhibitory Activity of compounds of the present invention.

TABLE 11a

% of positive relative to COX-2 inhibitory activity of COX-2 activity in the present of products from LPS-primed human neutrophils. 100% would indicate no inhibition, 0% would indicate complete inhibition.

| | n = 1 | n = 2 | Avg % of control |
|---|---|---|---|
| DMSO LPS A23187 | 100.0 | 100.0 | 100.0 |
| NS398 10 µM (positive control) | 1.5 | 10.2 | 5.8 |
| NS398 1 µM (positive control) | 3.4 | 15.4 | 9.4 |
| CAPE 1 µM | 29.6 | 75.2 | 52.4 |
| 25 1 µM | 34.9 | 81.3 | 58.1 |
| 39 1 µM | 62.9 | 90.2 | 76.6 |
| 32 1 µM | 34.3 | 69.0 | 51.6 |
| 33 1 µM | 7.6 | 45.3 | 26.4 |
| 40 1 µM | 37.8 | 86.4 | 62.1 |
| 55 1 µM | 102.7 | 101.0 | 101.8 |

TABLE 11b exemplary Cyclooxygenase-1 (COX-1) Inhibitory Activity in human platelets of compounds Of The Present Invention.

| Compound | Percent inhibition at 1 µM | IC$_{50}$ |
|---|---|---|
| 25 | | 0.086 |
| 32 | 42% | |
| 40 | | 0.068 |
| 34 | <20% | n/d |
| 36 | <20% | n/d |
| 45 | | 0.52 |
| 21 | 44.6 | |
| 20 | 37.2 | |
| 22 | 39.6 | |

REFERENCES

Borgeat P, Picard S, Vallerand P, Bourgoin S, Odeimat A, et al. (1990) Automated on-line extraction and profiling of lipoxygenase products of arachidonic acid by high-performance liquid chromatography. Methods Enzymol 187: 98-116.

Boudreau L H, Picot N, Doiron J, Villebonet B, Surette M E, et al. (2009) Caffeoyl and cinnamoyl clusters with anti-inflammatory and anti-cancer effects. Synthesis and structure-activity relationship. New J Chem 33: 1932-1940.

Boudreau L H, Maillet J, LeBlanc L M et al. (2012) Caffeic acid phenethyl ester and its amide analogue are potent inhibitors of leukotriene biosynthesis in human polymorphonuclear leukocytes. PLOSONE, 7, e31833.

Boyum A (1968) Isolation of mononuclear cells and granulocytes from human blood. Isolation of monuclear cells by one centrifugation, and of granulocytes by combining centrifugation and sedimentation at 1 g. Scand J Clin Lab Invest Suppl 97: 77-89.

Carter G W1, Young P R, Albert D H, Bouska J, Dyer R, Bell R L, Summers J B, Brooks D W. 1991. 5-lipoxygenase inhibitory activity of zileuton. J Pharmacol Exp Ther. 256:929-37.

Flamand N, Surette M E, Picard S, Bourgoin S, Borgeat P (2002) Cyclic AMPmediated inhibition of 5-lipoxygenase translocation and leukotriene biosynthesis in human neutrophils. Mol Pharmacol 62: 250-256.

Surette M E, Odeimat A, Palmantier R, Marleau S, Poubelle P E, et al. (1994) Reverse-phase high-performance liquid chromatography analysis of arachidonic acid metabolites in plasma after stimulation of whole blood ex vivo. Anal Biochem 216: 392-400.

What is claimed is:

1. A compound selected from:

| Cmp # | Name | Structure |
|---|---|---|
| 7 | (E)-phenethyl 3-(3,4-dichlorophenyl)acrylate | 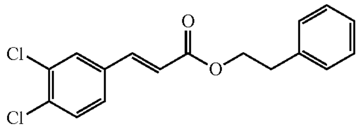 [SMILES: O=C(/C=C/c1ccc(Cl)c(Cl)c1)OCCc1ccccc1] |
| 10 | (E)-3-phenylpropyl 3-(3,5-dimethoxyphenyl)acrylate | 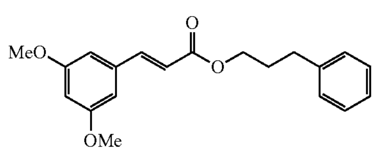 [SMILES: COc1cc(/C=C/C(=O)OCCCc2ccccc2)cc(OC)c1] |
| 13 | (E)-phenethyl 3-(3,5-bis(trifluoromethyl)phenyl)acrylate | 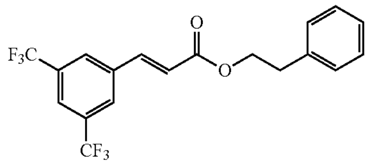 [SMILES: O=C(/C=C/c1cc(C(F)(F)F)cc(C(F)(F)F)c1)OCCc1ccccc1] |
| 136 | (E)-4-(2-(3-benzyl-1,2,4-oxadiazol-5-yl)vinyl)-2,6-dimethoxyphenol | |
| 137 | (E)-2,6-dimethoxy-4-(2-(3-phenethyl-1,2,4-oxadiazol-5-yl)vinyl)phenol | |

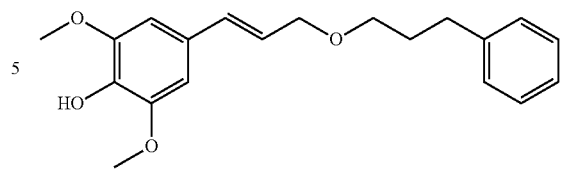

or a pharmaceutically acceptable salt thereof.

2. The compound according to claim 1, wherein the compound is:

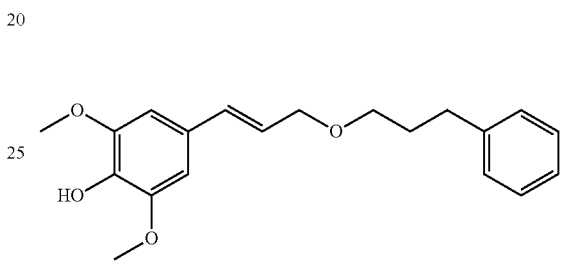

or a pharmaceutically acceptable salt thereof.

3. A pharmaceutical composition comprising a compound according to claim 1, or a pharmaceutically acceptable salt thereof, and a pharmaceutically acceptable carrier.

4. A method of modulating lipoxygenase and/or cyclooxygenase activity, comprising contacting said lipooxygenase and/or cyclooxygenase with a compound according to claim 1.

5. A method of treating or lessoning the severity of a lipoxygenase and/or a cyclooxygenase mediated disease or condition, comprising administering to subject in need thereof a compound selected from the group consisting of

| Cmp # | Name | Structure |
|---|---|---|
| 7 | (E)-phenethyl 3-(3,4-dichlorophenyl)acrylate | 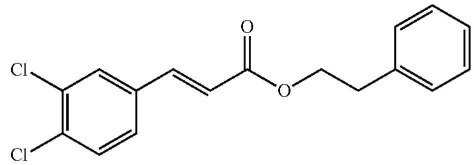 [SMILES: O=C(/C=C/c1ccc(Cl)c(Cl)c1)OCCc1ccccc1] |
| 10 | (E)-3-phenylpropyl 3-(3,5-dimethoxyphenyl)acrylate | 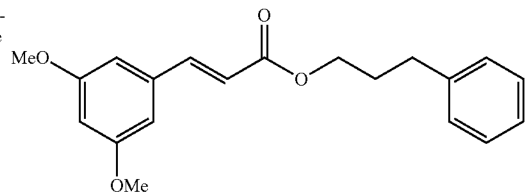 |
| 13 | (E)-phenethyl 3-(3,5-bis(trifluoromethyl)phenyl)acrylate | 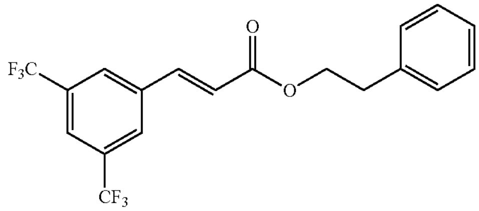 [SMILES: O=C(/C=C/c1cc(C(F)(F)F)cc(C(F)(F)F)c1)OCCc1ccccc1] |

| D |
|---|
| Ethyl |
| n-propyl |
| $CH_2CCH$ |
| Isopropyl |
| $CH_2CH{=}C(CH_3)_2$ |

128

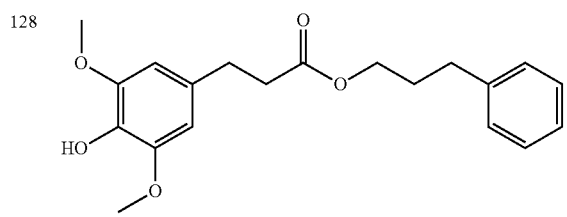

131

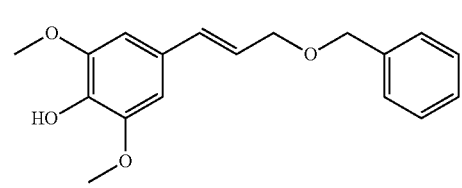

133

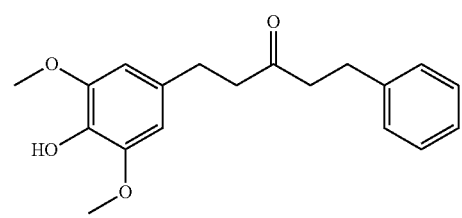

134

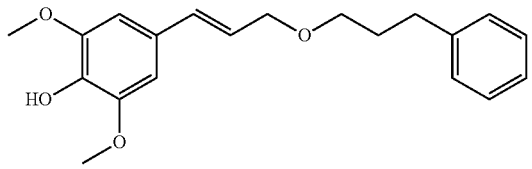

136

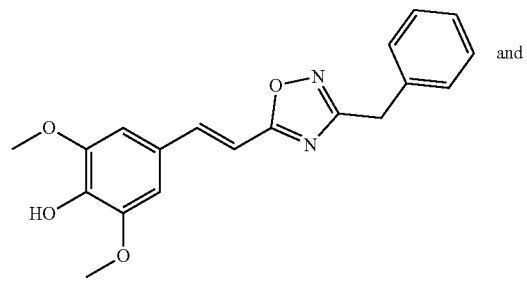

and

137

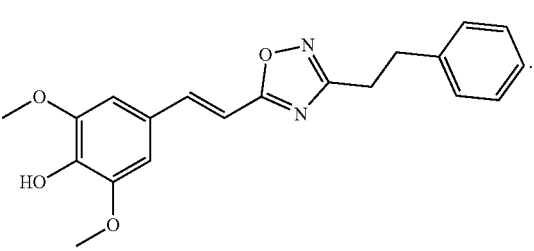

.

6. The method according to claim 5, wherein the compound is selected from the group consisting of Compound 131, Compound 133, Compound 134, Compound 136, or Compound 137.

7. The method according to claim 5, wherein the disease or condition is selected from the group consisting of inflammation, chronic inflammation, inflammation-associated disorder, metabolic syndrome, pain, headache, fever, arthritis, rheumatoid arthritis, spondyloarthopathies, gouty arthritis, osteoarthritis, systemic lupus erythematosus, juvenile arthritis, asthma, bronchitis, menstrual cramps, tendinitis, bursitis, psoriasis, eczema, burns, dermatitis, inflammatory bowel disease, Crohn's disease, gastritis, irritable bowel syndrome, ulcerative colitis, colorectal cancer, prostate cancer, lung cancer, breast cancer, vascular disease, migraine headache, periarteritis nodosa, thyroiditis, aplastic anemia, Hodgkin's disease, sclerodoma, rheumatic fever, type I diabetes, myasthenia gravis, sarcoidosis, nephrotic syndrome, Behcet's syndrome, polymyositis, gingivitis, hypersensitivity, conjunctivitis, swelling occurring after injury, myocardial ischemia, allergic rhinitis, respiratory distress syndrome, endotoxic shock syndrome, atherosclerosis, and stroke.

8. The method according to claim 4, wherein lipoxygenase and/or cyclooxygenase activity is modulated in a subject having a lipoxygenase and/or a cyclooxygenase mediated disease or condition, and the method further comprises treating or lessoning the severity of the disease or condition.

9. The method according to claim 8, wherein the disease or condition is selected from the group consisting of inflammation, chronic inflammation, inflammation-associated disorder, metabolic syndrome, pain, headache, fever, arthritis, rheumatoid arthritis, spondyloarthopathies, gouty arthritis, osteoarthritis, systemic lupus erythematosus, juvenile arthritis, asthma, bronchitis, menstrual cramps, tendinitis, bursitis, psoriasis, eczema, burns, dermatitis, inflammatory bowel disease, Crohn's disease, gastritis, irritable bowel syndrome, ulcerative colitis, colorectal cancer, prostate cancer, lung cancer, breast cancer, vascular disease, migraine headache, periarteritis nodosa, thyroiditis, aplastic anemia, Hodgkin's disease, sclerodoma, rheumatic fever, type I diabetes, myasthenia gravis, sarcoidosis, nephrotic syndrome, Behcet's syndrome, polymyositis, gingivitis, hypersensitivity, conjunctivitis, swelling occurring after injury, myocardial ischemia, allergic rhinitis, respiratory distress syndrome, endotoxic shock syndrome, atherosclerosis, and stroke.

\* \* \* \* \*